(12) United States Patent
Yamazaki et al.

(10) Patent No.: US 10,202,446 B2
(45) Date of Patent: Feb. 12, 2019

(54) ANTI FGF23 ANTIBODY AND A PHARMACEUTICAL COMPOSITION COMPRISING THE SAME

(71) Applicant: KYOWA HAKKO KIRIN CO., LTD., Chiyodo-ku, Tokyo (JP)

(72) Inventors: Yuji Yamazaki, Gunma (JP); Itaru Urakawa, Gunma (JP); Hitoshi Yoshida, Gunma (JP); Yukiko Aono, Gunma (JP); Takeyoshi Yamashita, Tokyo (JP); Takashi Shimada, Gunma (JP); Hisashi Hasegawa, Gunma (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 140 days.

(21) Appl. No.: 15/040,103

(22) Filed: Feb. 10, 2016

(65) Prior Publication Data

US 2016/0159895 A1 Jun. 9, 2016

Related U.S. Application Data

(60) Division of application No. 13/019,557, filed on Feb. 2, 2011, now Pat. No. 9,290,569, which is a continuation of application No. 12/030,593, filed on Feb. 13, 2008, now Pat. No. 7,883,705.

(30) Foreign Application Priority Data

Feb. 14, 2007 (JP) .................................. 2007-034018

(51) Int. Cl.
| | | |
|---|---|---|
| *C07K 16/22* | (2006.01) | |
| *C07K 16/24* | (2006.01) | |
| *A61K 39/00* | (2006.01) | |

(52) U.S. Cl.
CPC ............ *C07K 16/22* (2013.01); *C07K 16/244* (2013.01); *A61K 2039/505* (2013.01); *C07K 2317/24* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,585,089 A | 12/1996 | Queen et al. | |
| 5,859,205 A | 1/1999 | Adair et al. | |
| 5,958,879 A | 9/1999 | Kopchick et al. | |
| 6,001,358 A | 12/1999 | Black et al. | |
| 6,617,118 B2 | 9/2003 | Roffler et al. | |
| 7,094,551 B2 | 8/2006 | Zahradnik et al. | |
| 7,223,563 B2 | 5/2007 | Econs et al. | |
| 7,314,618 B2 | 1/2008 | Econs et al. | |
| 7,883,705 B2 | 2/2011 | Yamazaki et al. | |
| 2004/0082506 A1 | 4/2004 | Yamashita et al. | |
| 2004/0120948 A1 | 6/2004 | Mitayama et al. | |
| 2004/0171825 A1 | 9/2004 | Bougueleret et al. | |
| 2005/0048058 A1 | 3/2005 | Yamazaki et al. | |
| 2006/0160181 A1 | 7/2006 | Luethy et al. | |
| 2007/0036734 A1 | 2/2007 | Tahara et al. | |
| 2007/0141054 A1 | 6/2007 | Kataoka et al. | |
| 2009/0110677 A1 | 4/2009 | Yamashita et al. | |

FOREIGN PATENT DOCUMENTS

| | | |
|---|---|---|
| CA | 2418215 | 1/2002 |
| CN | 1446227 A | 10/2003 |
| EP | 120694 | 10/1984 |
| EP | 125023 | 11/1984 |
| EP | 0314161 A1 | 10/1988 |
| EP | 1466925 A1 | 10/2004 |
| GB | 2188638 A | 10/1987 |
| JP | S-61-178926 | 11/1986 |
| JP | H-02-117920 | 2/1990 |
| WO | WO 99/60017 | 11/1999 |
| WO | WO 00/10383 | 3/2000 |
| WO | WO 00/60085 A1 | 10/2000 |
| WO | WO 00/73454 A1 | 12/2000 |
| WO | WO 01/40466 A2 | 6/2001 |
| WO | WO 01/42451 A2 | 6/2001 |
| WO | WO 2001/49740 | 7/2001 |
| WO | WO 01/60850 A1 | 8/2001 |
| WO | WO 01/061007 A2 | 8/2001 |
| WO | WO 02/08271 A1 | 8/2001 |
| WO | WO 01/66595 A2 | 9/2001 |
| WO | WO 01/66596 A2 | 9/2001 |
| WO | WO 02/14504 A1 | 2/2002 |
| WO | WO 02/076467 A1 | 3/2002 |
| WO | WO 02/088358 A2 | 11/2002 |
| WO | WO 03/057733 A1 | 1/2003 |
| WO | WO 2002/43478 | 5/2004 |

(Continued)

OTHER PUBLICATIONS

Berndt et al. (Am J Physiol Renal Physiol 289:1170-1182, 2005) (Year: 2005).*
Kobayashi et al. (Life Sciences 78 (2006) 2295-2301) (Year: 2006).*
Kobayashi et al., Eur J. of Endocrinol. 2006 Ian;154(1):93-9. (Year: 2006).*
El-Kishawi et al., Saudi J Kidney Dis Transplant 2006;17(3):373-382. (Year: 2006).*
Olgaard et al., Clin J Am Soc Nephrol 1: 367-373, 2006. (Year: 2006).*

(Continued)

*Primary Examiner* — Zachary S Skelding
(74) *Attorney, Agent, or Firm* — Foley & Lardner LLP

(57) ABSTRACT

To provide an antibody against FGF23 and a pharmaceutical composition such as a preventive or therapeutic agent which can prevent or treat by suppressing an action of FGF23 by using the antibody. An antibody or its functional fragment against human FGF23 produced by hybridoma C10 (Accession No. FERM BP-10772).

4 Claims, 19 Drawing Sheets
Specification includes a Sequence Listing.

(56) References Cited

FOREIGN PATENT DOCUMENTS

| WO | WO 2004/083425 A1 | 9/2004 |
|---|---|---|
| WO | WO 2006/028197 A1 | 3/2006 |
| WO | WO 2006/78072 A1 | 7/2006 |
| WO | WO 2008/057683 | 5/2008 |
| WO | WO 2008092019 A1 | 7/2008 |

OTHER PUBLICATIONS

Seiji Fukumoto (Calcif Tissue Int (2016) 98:334-340). (Year: 2016).*
Ando, et al., *Tan-Clone-Kotai-Jikken-Manual* ("Experimental Manual for Monoclonal Antibody") (written by and published by Kodansha Scientific, Ltd., Tokyo, Japan (1991).
Antibody Engineering, A Practical Approach, IRL Press, 1996.
Antibody Engineering, A Practical Guide, W.H. Freeman and Company, 1992.
Baker and Worthley, "The Essentials of Calcium, Magnesium and Phosphate Metabolism: Part II. Disorders," *Critical Care & Resuscitation.*, 2000, vol. 4, pp. 307-315.
Better, et al., "*Escherichia coil* Secretion of an Active Chimeric Antibody Fragment," *Science*, May 20, 1998 (nti), vol. 240, pp. 1041-1043.
Bruggemann, et al., "The Immunogenicity of Chimeric Antibodies", *J. Exp. Med.*, Dec. 1989, vol. 170, No. 6, pp. 2153-2157.
Carter, et al., "High Level *Escherichia coli* Expression and Production of a Bivalent Humanized Antibody Fragment," *Bio/Technology*, 1992, vol. 10, pp. 163-167.
Delves, P. J., "Antibody Production Essential Techniques", *Monoclonal Antibodies*, Ed. Shepherd and Dean, Oxford University Press, 2000.
Fishwild, et al., "High-avidity Human IgGx Monoclonal Antibodies from a Novel Strain of Minilocus Transgenic Mice," *Nat Biotechnol.*, Jul. 1996, vol. 14, No. 7, pp. 845-851.
Goding, J. W., *Monoclonal Antibodies: Principles and Practice*, Academic Press, 1993 and 1995.
Gupta, et al., "FGF-23 is Elevated by Chronic Hyperphosphatemia," *J. Clin. Endocrinol.& Metab.*, 2004. vol. 89, No. 9, pp. 4489-4492.
Harlow et al., Using Antibodies: A Laboratory Manual, Cold Spring Harbor Laboratory Press, 1999, p. 4.
Horibata and Harris, *Nature*, 1975, No. 256, pp. 495-497.
Ishida & Lonberg, IBC's 11th Antibody Engineering, Abstract 2000.
Jonsson, et al., "Fibroblast Growth Factor 23 in Oncogenic Osteomalacia and X-Linked Hypophosphatemia,"*N. Engl. J. Med.*, Apr. 24, 2003, vol. 348, No. 17, pp. 1656-1663.
Karlsson, et al., "Kinetic Analysis of Monoclonal Antibody-Antigen Interactions with a New Biosensor Based Analytical System," *Journal of Immunological Methods*, 1991, vol. 145, pp. 229-240.
Kearney, et al., "A New Mouce Myeloma Cell Line that has Lost Immunoglobulin Expression but Permits the Construction of Antibody-Secreting Hybrid Cell Lines", *J. Immunology*, Sep. 1979, vol. 123, No. 3, pp. 1548-1550.
King, D.J., *Applications and Engineering of Monoclonal Antibodies*, T. J. International Ltd, 1998.
Kitamura, et al., "A B Cell-deficient Mouse by Targeted Distribution of the Membrane Exon of the Immunoglobulin μ Chain Gene," *Nature*, 1991, vol. 350, No. 4, pp. 423-426.
Kohler, et al., "Derivation of Specific Antibody-producing Tissue Culture and Tumor Lines by Cell Fusion", *European J. Immunology*, 1966, vol. 6, pp. 511-519.
Lah, et al., "Phage Surface Presentation and Secretion of Antibody Fragments using an Adaptable Phagemid Vector," *Human Antibodies & Hybridomas*, 1994, vol. 5, Nos. 1 and 2, pp. 48-56.
Larsson, et al., "Circulating Concentration of FGF-23 Increases as Renal Function Declines in Patients with Chronic Kidney Disease, but does not Change in Response to Variation in Phosphate Intake in Healthy Volueners," *Kidney International*, 2003, vol. 64, pp. 2272-2279.

Lonberg et al., Nature, 1994, 368, 6474, 856-859.
Lorenz-Depiereux, et al., "DMP1 Mutations in Autosomal Recessive Hypophosphatemia Implicate a Bone Matrix Protein in the Regulation of Phosphate Homeostasis," *Nature Genetics*, Nov. 2006, vol. 38, No. 11, pp. 1248-1250.
Mark, et al., "Site-specific Mutagenesis of the Human Fibroblast Interferon Gene", *Proc Natl Aced Sci U.S.A.*, Sep. 1984, vol. 81, No. 18, pp. 5662-5666.
Ornitz, et al., "Fibroblast Growth Factors," *Genome Biology*, 2001, vol. 2, No. 3, pp. 3005.1-3005.12.
Reiter, et al., "Engineering Interchain Disulfide Bonds into Conserved Framework Regions of Fv Fragments: Improved Biochemical Characteristics of Recombinant Immunotoxins Containing Disulfide-stabilized Fv", *Protein Engineering*, 1994, vol. 7, No. 5, pp. 697-704.
Riechmann, et al., "Reshaping Human Antibodies for Therapy", *Nature*, Mar. 1988, vol. 332, No. 6162, pp. 323-327.
Riminucci, et al., "FGF-23 in Fibrous Dysplasia of Bone and its Relationship to Renal Phosphate Wasting," *J. Clin. Invest.*, 2003, vol. 112, No. 5, pp. 683-692.
Shimada, et al., "Cloning and Characterization of FGF23 as a Causative Factor of Tumor-induced Osteomalacia", *Proc. Natl. Acad. Sci.*, May 2, 2001, vol. 98, No. 11, pp. 6500-6505.
Shinichi Aizawa, "Biotechnology Manual Series 8, Gene Targeting," Yodosha, 1995.
Shulman, et al., "A Better Cell Line for Making Hybridomas Secreting Specific Antibodies", *Nature*, Nov. 1978, vol. 276, No. 5685, pp. 269-270.
Sunaga, et al., "Efficient Removal of IoxP-Flanked DNA Sequences in a Gene-Targeted Locus by Transient Expression of Cre Recombinanse in Fertilized Eggs," *Molecular Reproduction and Development*, 1997, vol. 46, pp. 109-113.
Tomizuka, et al., "Double Trans-Chromosomic Mice: Maintenance of Two Individual Human Chromosome Fragments Containing Ig Heavy and Antibodies", *Proc Nati Arad Sci U.S.A.*, 2000, vol. 97, No. 2, pp. 722-727.
Urakawa, et al., "Klotho Converts Canonical FGF Receptor into a Specific Receptor for FGF23," *Nature*, Dec. 2006, vol. 444, pp. 770-774.
Van Kroonenbergh, et al., "Human Immunological Response to Mouse Monoclonal Antibodies in the Treatment or Diagnosis of Malignant Diseases," *Nuclear Medicine Communications.*, 1988, vol. 9, pp. 919-930.
White, et al., "Autosomal Dominant Hypophosphataemic Rickets is Associated with Mutations in FGF23", *Nature Genetics*, Nov. 2000, vol. 26, pp. 345-348.
Wright, et al., "High Level Expression of Active Human Alpha-1-Antitrypsin in the Milk of Transgenic Sheep", *Bio/Technology*, Sep. 1991, vol. 9, No. 9, pp. 830-834.
Yamamoto, et al., "The Role of Fibroblast Growth Factor 23 in Hypophosphatemia and Abnormal Regulation of Vitamin D Metabolism in Patients with McCune-Albright Syndrome," *J. Bone Miner. Metab.*, 2005, vol. 23, pp. 231-237.
Yamashita, et al., "Identification of a Novel Fibroblast Growth Factor, FGF-23, Preferentially Expressed in the Ventrolateral Thalamic Nucleus of the Brain," *Biochemical and Biphysical Research Communications*, 2000, vol. 277, pp. 494-498.
Portolano et al., J. Immunol., Feb. 1, 1993, 150(3):880-887.
Padlan, Edurado, Mol. Immunol., Feb. 1994, 31(3):169-217.
Vaidos et al., J. Mol. Biol, Jul. 5, 2002, 320(2):415-428.
Yamazaki, et al., "Increased Circulatory Level of Biologically Active Full Length FGF-23 in Patients with Hypophosphatemic Rickets/Osteomalacia," *J. Clin. Endocrinol. Metab.*, 2002, vol. 87, pp. 4957-4960.
Yelton, et al. , "Fusion of Mouse Myeloma and Spleen Cells", *Current Topics in Microbiology and Immunology*, 1978, vol. 81, pp. 1-7.
International Search Report of PCT Patent Application No. PCT/JP2008/052918 dated Mar. 13, 2008—international, counterpart to U.S. Appl. No. 12/030,593.
Non-Final Office Action for U.S. Appl. No. 10/344,339 dated Jan. 18, 2008.

(56) References Cited

OTHER PUBLICATIONS

Advisory Action for U.S. Appl. No. 10/344,339 dated Dec. 7, 2007.
Final Office Action for U.S. Appl. No. 10/344,339 dated Jun. 22, 2007.
Non-Final Office Action for U.S. Appl. No. 10/344,339 dated Sep. 27, 2006.
Notice of Allowance for Korean Patent Application No. 10-2003-7001931 dated Nov. 26, 2008—international, counterpart to U.S. Appl. No. 10/344,339. (No English-language Translation Available).
Office Action for Canadian Patent Application No. 2,418,802 dated Feb. 13, 2009—international, counterpart to U.S. Appl. No. 10/344,339.
Supplementary European Search Report of European Patent Application No. EP 01 95 8379 dated May 27, 2005—international, counterpart to U.S. Appl. No. 10/344,339.
Final Office Action for U.S. Appl. No. 10/500,296 dated Apr. 10, 2009.
Non-Final Office Action for U.S. Appl. No. 10/500,296 dated Jul. 24, 2008.
Advisory Action for U.S. Appl. No. 10/500,296 dated Mar. 28, 2008.
Final Office Action for U.S. Appl. No. 10/500,296 dated Oct. 19, 2007.
Non-Final Office Action for U.S. Appl. No. 10/500,296 dated Jan. 30, 2007.
Non-Final Office Action for U.S. Appl. No. 10/500,296 dated Jan. 13, 2006.
International Search Report of PCT Patent Application No. PCT/JP03/00017 dated Feb. 5, 2003—international, counterpart to U.S. Appl. No. 10/500,296.
Aono et al., "The improving effect of anti FGF23 neutralizing antibody on hypophosphatemia and rickets of Hyp mice", The Japanese Society for Bone and Mineral Research (JSBMR), Annual Meeting of the JSBMR, 22$^{nd}$ Program, Aug. 2004, vol. 22, pp. 137. (English translation provided).
Aschinberg et al., "Vitamin D-resistant rickets associated with epidermal nevus syndrome: Demonstration of a phosphaturic substance in the dermal lesions," The Journal of Pediatrics, vol. 91, No. 1, Jul. 1997, pp. 56-60, The C.V. Mosby Company, St. Louis, Mo.
Benjannet et al., "α1-Antitrypsin Portland Inhibits Processing of Precursors Mediated by Proprotein Convertases Primarily within the constitutive Secretory Pathway," The Journal of Biological Chemistry, vol. 272, No. 42, Oct. 17, 1997, pp. 2610-2618, The American Society for Biochemistry and Molecular Biology, Inc.
Bost, et al., "Antibodies Against a Peptide Sequence within the HIV Envelope Protein Crossreacts with Human Interleukin-2", Immunol. Invest., 1988, vol. 17, Nos. 577-586.
Briand et al., "Application and limitations of the multiple antigen peptide (MAP) system in the production and evaluation of anti-peptide and anti-protein antibodies", Journal of Immonnological Methods, vol. 156, No. 2, 1992, pp. 255-265, Elsevier Science Publishers B.V.
Cai et al., "Brief Report: Inhibition of Renal Phosphate Transport by a Tumor Product in a Patient with Oncogenic Osteomalacia", The New England Journal of Medicine, vol. 330, No. 23, Jun. 9, 1994, pp. 1645-1649, The Massachusetts Medical Society.
Campbell, A.M., Monoclonal Antibody Technology, Elsevier Science Publishers, Inc., 1984, pp. 1-32.
Drezner, "PHEX gene and hypophosphatemia", Kidney International, vol. 57, No. 1, Jan. 2000, pp. 9-18, The International Society of Nephrology.
Ecarot et al., "Defective Bone Formation by Hyp Mouse Bone cells Transplanted into Normal Mice: Evidence in Favor of an Intrinsic Osteoblast Defect", Journal of Bone and Mineral Research, vol. 7, No. 2, Feb. 1992, pp. 215-220, Mary Ann Liebert, Inc.
Econs et al., "Autosomal Dominant Hypophosphatemic Rickets Is Linked to Chromosome 12p13", The Journal of Clinical Investigation, vol. 100, No. 11, Dec. 1, 1997, pp. 2653-2657, The Rockefeller University Press.

Econs et al., "Tumor-Induced Osteomalacia—Unveiling a New Hormone", The New England Journal of Medicine, vol. 330, No. 23, Jun. 9, 1994, pp. 1679-1681, The Massachusetts Medical Society.
Econs, "New Insights Into The Pathogenesis of Inherited Phosphate Wasting Disorders" Bone, vol. 25, No. 1, Jul. 1999, pp. 131-135 Pergamon Press, Oxford, GB.
Fukagawa, et al., "FGF23: its Role in Renal Bone Disease", Pediat. Nephrol, 2006, vol. 21, pp. 1802-1806.
Fukumoto et al., "Diagnostic Utility of Magnetic Resonance Imaging Skeletal Survey in a Patient With Oncogenic Osteomalacia", Bone, vol. 25, No. 3, Sep. 1999, pp. 375-377, Elsevier.
Han et al., "Epinephrine translocates GLUT-4 but inhibits insulin-stimulated glucose transport in rat muscle", American Journal of Physiology, vol. 272, No. 4, Apr. 1998, p. E700-7, The American Physiology Society.
Imel, et al., "FGF23 Concentrations Vary with Disease Status in Autosomal Dominant Hypophosphatemic Rickets,", J. of Bone and Mineral Research, 2007, vol. 22, pp. 520-526.
Kessler et al., "A Modified Procedure For The Rapid Preperation of Efficiently Transporin Vesicles From Small Intestinal Brush Border Membranes", Biochimica et Biophysica Acta, vol. 506, No. 1, Jan. 4, 1978, pp. 136-155, Elsevier/North-Holland Biomedical Press.
Lajeunesse et al., "Direct demonstration of a humorally-mediated inhibition of renal phosphate transport in the Hyp mouse", Kidney International, vol. 50, No. 5, Nov. 1996, pp. 1531-1538, The International Society of Nephrology.
Lau et al., "Evidence for a Humoral Phosphaturic Factor in Oncogenic Hypophospatemic Osteomalacia", Clinical Research, vol. 27, No. 2, Apr. 1979, p. 421A.
Lorenz-Depiereux et al., "Autosomal Dominant Hypophosphatemic Rickets (ADHR) Is Caused by Mutations in A Gene Encoding A Novel Member of the Fibroblast Growth Factor Family(FGF-21)" American Journal of Human Genetics, vol. 67, No. 4, suppl. 2, Oct. 2000, p. 12.
Lorenz-Depiereux, et al., The Autosomal Dominant Hypophosphatemic Rickets (ADHR) Gene is a Secreted Fibroblast Growth Factor (FGF23), Eur. J. Human Genetics, 2001, vol. 9, Supplement 1, P0772, 10$^{th}$ International Congress of Human Genetics, Vienna Austria, May 15-19, 2001.
Lu et al., "Chemically Unambiguous Peptide Immunogen: Preparation, Orientation and Antigenicity of Purified Peptide Conjugated to the Multiple Antigen Peptide System", Molecular Immunology, vol. 28, No. 6, Jun. 1991, pp. 623-630, Pergamon Press, Great Britain.
Meyer et al., "Parabiosis Suggests a Humoral Factor Is Involved inX-Linked Hypophosphatemia in Mice", Journal of Bone and Mineral Research, vol. 4, No. 4, Aug. 1989, pp. 493-500, Mary Ann Seibert, Inc.
Miyauchi et al, Hemanglopericytoma-Induced Osteomalacia: Tumor Transplantation in Nude Mice Causes Hypophosphatemia and Tumor Extracts Inhibit Renal 25-Hydroxyvitamin D 1-Hydroxylase Activity, Journal of Clinical Endocrinology and Metabolism, vol. 67, No. 1, Jul. 1988, pp. 46-53, The Endocrine Society.
Mohammadi, et al., "Structual Basis for Fibroblast Growth Factor Receptor Activation," Cytokine & Growth Factor Reviews, Apr. 2005, vol. 16, No. 2, pp. 107-137.
NCBI GenBank Accession No. NP_065689 (Mar. 25, 2007).
NCBI GenBank Accession No. NM_020638 (Mar. 25, 2007).
NCBI GenBank Accession No. AY566236 (Mar. 16, 2004).
Nelson et al., "Oncogenic osteomalacia: is there a new phosphate regulating hormone?", Clinical Endocrinology, vol. 47, No. 6, Dec. 1997, pp. 635-642, Blackwell Science Ltd.
Nykjaer et al., "An Endocytic Pathway Essential for Renal Uptake and Activation of the Steroid 25-(OH) Vitamin $D_3$", Cell, vol. 96, No. 4, Feb. 19, 1999, pp. 507-515,Cell Press.
Popovtzer et al., "Tumor-Induced Hypophosphatemic Osteomalacia (TUO): Evidence for a Phosphaturic Cyclic AMP-Independent Action of Tumor Extract", Clinical Research, vol. 29, No. 2, Apr. 1981, p. 418A.
Posnett et al., "A Novel Method for Producing Anti-peptide Antibodies", The Journal of Biological Chemistry, vol. 263, No. 4, Feb. 5, 1988, pp. 1719-1725, The American Society for Biochemistry and Molecular Biology, Inc.

(56) References Cited

OTHER PUBLICATIONS

Rowe et al., "Candidate 56 and 58 kDa Protein(s) Responsible for Mediating the Renal Defects in Oncogenic Hypophosphatemic Osteomalacia", Bone, vol. 18, No. 2, Feb. 1996, pp. 159-169, Elsevier.
Rowe et al., "MEPE, a New Gene Expressed in Bone Marrow and Tumors Causing Osteomalacia", Genomics, vol. 67, No. 1, Jul. 1, 2000, pp. 54-68, Academic Press.
Shibata et al., "Monoclonal Antibodies Against Recombinant Human FGF-23", J. Am. Soc. Nephrol., Sep. 2002, vol. 13, p. 499A (SU-P0151).
Shimada et al., "Mutant FGF-23 responsible for autosomal dominant hypophosphatemic rickets is resistant to proteolytic-cleavage and causes hypophosphatemia in vivo", Endocrinology, Aug. 2002, vol. 143, No. 8 pp. 3179-3182.
Shimada et al, "FGF-23 Is a Novel Humoral Factor Regulating Vitamin D Metabolism", Journal of the American Society of Nephrology, Sep. 2002, vol. 13, (Program & Abstract Issue), p. 28A.
Shimada, T, "Targeted Ablation of FGF23 Demonstrates an Essential Physiological Role of FGF23 in Phosphate and Vitamin D Metabolism ", J. Clin. Invest., Feb. 2004, vol. 113, No. 4, pp. 561-568.
Shimada, T. "FGF23 and Phosphorus metabolism", The Japanese Society for Bone and Mineral Research (JSBMR), Annual Meeting of the JSBMR, 23$^{rd}$ Program, Jun. 20, 2005, vol. 23, pp. 121. (English translation provided).
Shirahata et al., "E1A and ras Oncogenes Synergistically Enhance Recombiant Protei Production under Control of the Cytomegalovirus Promoter in BHK-21 Cells", Biosci. Biotech. Biochem., vol. 59, No. 2, Feb. 1995, pp. 345-347, Japan Society for Bioscience, Biotechnology, and Agrochemistry.
Strom et al., "Pex gene deletions in Gy and Hyp mice provide mouse models for X-linked hypophosphatemia", Human Molecular Genetics, vol. 6, No. 2, Feb. 1997, pp. 165-171, The Oxford University Press.
Superti-Furga, et al., "Molecular-Pathogenetic Classification of Genetic Disorders of the Skeleton," American Journal of Medical Genetics, Siminar Medical Genetics, 2001, vol. 106, pp. 282-293.
Tatsumi et al., "Identification of Three Isoforms for the NA$^+$-dependent Phosphate Cotransporter (NaPi-2) in Rat Kidney", The Journal of Biological Chemlsty, vol. 273, No. 44, Oct. 30, 1998, pp. 28568-28575, The Society for Biochemistry and Molecular Biology, Inc.
Wen, et al., "PTEN Controls Tumor-Induced Angiogenesis," Proc. Natl. Acad. Sci. USA, Apr. 14, 2001, vol. 98, No. 6, pp. 4622-4627.
White, et al., "Autosomal-dominant Hypophosphatemic Rickets (ADHR) Mutations Stabilize FGF-23", Kidney International, 2001, vol. 60, pp. 2079-2086.
White et al., "Molecular cloning of a novel human UDP-GalNAc: polypeptide N-acetylgalactosaminyltransferase, GalNAc-T8, and analysis as a candidate autosomal dominant hypophosphatemic rickets (ADHR) gene", Gene, Elsevier Biomedical Press, Amsterdam NL, vol. 246, No. 1-2, Apr. 2000, pp. 347-356.
Wilkins et al., "Oncogenic Osteomalacia: Evidence for a Humoral Phosphaturic Factor", Journal of Clinical Endocrinology and Metabolism, vol. 80, No. 5, Oct. 22, 2000, pp. 1628-1634, The Endocrine Society.
Yamazaki et al, "Development of the ELISA System Using Monoclonal Antibodies against FGF-23 and Demonstration of Increased Plasma Concentration of FGF-23 in Tumor-Induced Osteomalacia", ENDO, 2002, The Endocrine Society's 84$^{th}$ Annual Meeting, Program & Abstract, p. 66.
Yamazaki et al., "FGF-23 Protein is Present in Normal Plasma and Is increased in Patients with Tumor-Induced Osteomalacia", (Sep. 2002), The Journal of Bone and Mineral Research, vol. 17, suppl. 1, p. 159.
Yamazaki, et al., "Detection of Circulating FGF-23 by Monoclonal Antibodies Against Recombinant Human FGF-23", Journal of the American Society of Nephrology, vol. 13 (Program and Abstracts Issue), Sep. 2002, p. 499A.
Yamazaki, et al., "Anti-FGF23 neutralizing antibodies show the physiological role and structural features of FGF23", Journal of Bone and Mineral Research, vol. 23, No. 9, Sep. 2008, pp. 1509-1518.
Yu, et al., "Analysis of the Biochemical Mechanisms for the Endocrine Actions of Fibroblast Growth Factor-23", Endocrinology, Nov. 2005, vol. 146, No. 11, pp. 4647-4656.
Japanese Office Action 2003-5580417 dated Aug. 20, 2009.
Yukihiro Hasegawa et al., "Vitamin D-Resistant Hypophosphatemic Rickets", The Bone, vol. 15, No. 6, Nov. 2001, pp. 1-9.
Ann E. Bowe et al., "FGF-23 Inhibits Renal Tubular Phosphate Transport and Is a PHEX Substrate", Biochemical and Biophysical Research Communications 284, 977-981 (2001).
Non-Final Office Action dated Dec. 29, 2009, Issued in related U.S. Appl. No. 10/500,296.
Preissner et al., "Evaluation of the Immutopics Human FGF-23 (C-term) ELISA Kit", Clinical Chemistry, vol. 52, No. 6, Suppl. S, Jun. 2006, p. A179.
Supplementary European Search Report EP 08 71 1707 dated Feb. 9, 2010.
Japanese Office Action Application No. JP 2003-558047 dated Jan. 26, 2010.
Takashi Shimada et al., "Possible Roles of Fibroblast Growth Factor 23 in Developing X-Linked Hypophosphatemia", Clin. Pediatr. Endocrinol. 2005; 14(Supp123) 33-37.
Satoshi Toyoshima, "Experiment Techniques II", Hirokawa Publishing Co., 1995, first edition, pp. 110-113.
First Office Action Chinese Application No. 200810086683.1 dated Mar. 8, 2010.
Human Fibroblast Growth Factor-23 (FGF-23) Elisa Kit 96-Well Plate, EZHEGF23-32K, Millipore, Feb. 3, 2009 (17 pgs.).
Human Intact FGF-23 Elisa Kit, Enzyme-Linked ImmunoSorbent Assay (ELISA) for the Determination of Human Fibroblas Growth Factor 23 Levels in Plasma or Cell Culture, 96 Test Kit, Cat. No. 60-6500, Immutopcs, Inc., Oct. 2008 (4 pgs.).
Monoclonal Anti-Human FCG-23 Antibody, R&D Systems, Cat. No. MAB2604, Apr. 18, 2005.
Monoclonal Anti-human/mouse FGF-23 Antibody, R&D Systems, Cat. No. MAB2629, Sep. 13, 2007.
Monoclonal Anti-mouse FGF-23 Antibody, R&D Systems, Cat. No. MAB26291, Mar. 20, 2007.
Non-Final Office Action U.S. Appl. No. 12/030,593 dated Apr. 6, 2010.
Marc Drezner, Reviews in Endocine & Metabolic Disorders 2001; 2: 175-186.
Razzaque et al., Nephrol Dial Transplant. Oct. 2005; 20(10):2032-2035.
Inaba et al., Osteoporos Int. Oct. 2006; 17(10):1506-1513.
Vajdos et al., J. Mol. Biol. Jul. 5, 2002; 320(2)415-428.
Webster's New World Dictionary, Third College Edition, 1988, pp. 1067-1068.
Kobayashi et al., Eur J. Endocrinol. Jan. 2006; 154(1):93-99.
Notice of Allowance U.S. Appl. No. 12/030,593 dated Sep. 17, 2010.

\* cited by examiner

```
     BglII
  1  AGATCTCTCACC ATG GAC ATG AGG GTC CCC GCT CAG CTC CTG GGG CTT CTG CTG CTC TGG CTC
              1▶ [ M   D   M   R   V   P   A   Q   L   L   G   L   L   L   L   W   L ]
 64  CCA GGT GCC AGA TGT GCC ATC CAG TTG ACC CAG TCT CCA TCC TCC CTG TCT GCA TCT GTA GGA
 18▶ [ P   G   A   R   C ] A   I   Q   L   T   Q   S   P   S   S   L   S   A   S   V   G
127  GAC AGA GTC ACC ATC ACT TGC CGG GCA AGT CAG GGC ATT AGC AGT GCT TTA GTC TGG TAT CAG
 39▶   D   R   V   T   I   T   C   R   A   S   Q   G   I   S   S   A   L   V   W   Y   Q
190  CAG AAA CCA GGG AAA GCT CCT AAG CTC CTG ATC TAT GAT GCC TCC AGT TTG GAA AGT GGG GTC
 60▶   Q   K   P   G   K   A   P   K   L   L   I   Y   D   A   S   S   L   E   S   G   V
253  CCA TCA AGG TTC AGC GGC AGT GGA TCT GGG ACA GAT TTC ACT CTC ACC ATC AGC AGC CTG CAG
 81▶   P   S   R   F   S   G   S   G   S   G   T   D   F   T   L   T   I   S   S   L   Q
316  CCT GAA GAT TTT GCA ACT TAT TAC TGT CAA CAG TTT AAT GAT TAC TTC ACT TTC GGC CCT GGG
102▶   P   E   D   F   A   T   Y   Y   C   Q   Q   F   N   D   Y   F   T   F   G   P   G
                               BsiWI
379  ACC AAA GTG GAT ATC AAA CGT ACG GTG GCT GCA CCA TCT GTC TTC ATC TTC CCG CCA TCT GAT
123▶   T   K   V   D   I   K   R   T   V   A   A   P   S   V   F   I   F   P   P   S   D
442  GAG CAG TTG AAA TCT GGA ACT GCC TCT GTT GTG TGC CTG CTG AAT AAC TTC TAT CCC AGA GAG
144▶   E   Q   L   K   S   G   T   A   S   V   V   C   L   L   N   N   F   Y   P   R   E
505  GCC AAA GTA CAG TGG AAG GTG GAT AAC GCC CTC CAA TCG GGT AAC TCC CAG GAG AGT GTC ACA
165▶   A   K   V   Q   W   K   V   D   N   A   L   Q   S   G   N   S   Q   E   S   V   T
568  GAG CAG GAC AGC AAG GAC AGC ACC TAC AGC CTC AGC AGC ACC CTG ACG CTG AGC AAA GCA GAC
186▶   E   Q   D   S   K   D   S   T   Y   S   L   S   S   T   L   T   L   S   K   A   D
631  TAC GAG AAA CAC AAA GTC TAC GCC TGC GAA GTC ACC CAT CAG GGC CTG AGC TCG CCC GTC ACA
207▶   Y   E   K   H   K   V   Y   A   C   E   V   T   H   Q   G   L   S   S   P   V   T
                                                EcoRI
694  AAG AGC TTC AAC AGG GGA GAG TGT TGA ATTC
228▶   K   S   F   N   R   G   E   C
```

Fig. 4

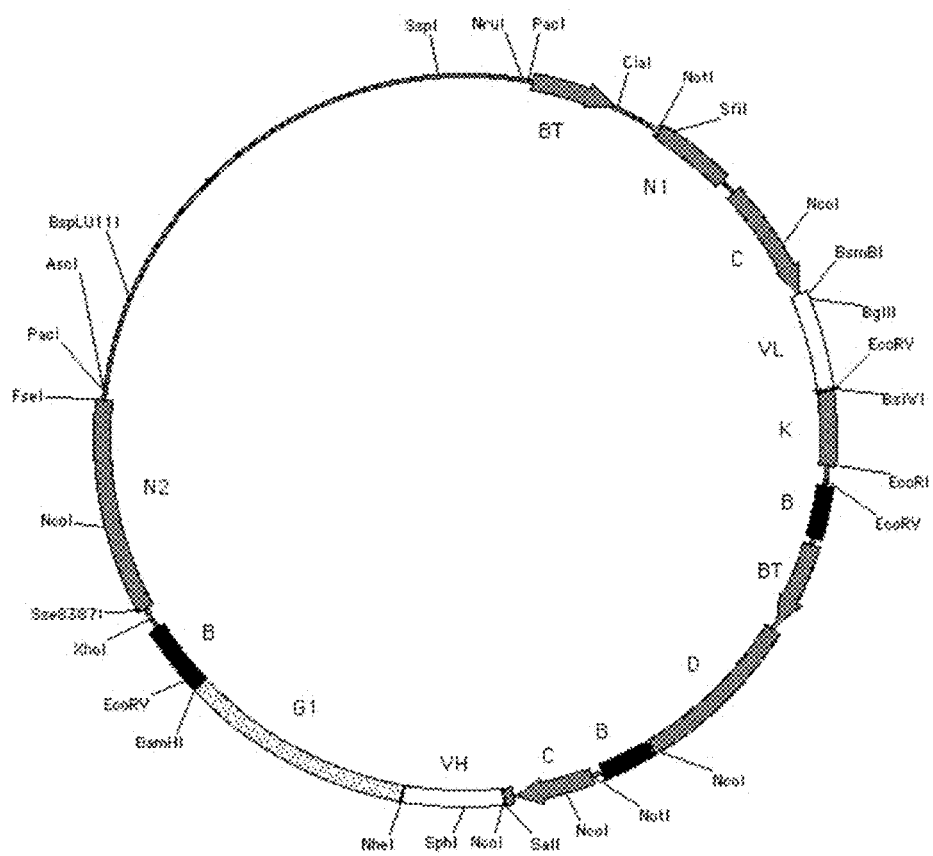

BT: Mouse beta globulin major promoter
N1: Neomycin phosphotransferase exon 1
C: Cytomegalovirus promoter/enhancer
B: Bovine growth hormone polyadenylation
VL: C10 light chain variable region
K: Human immunoglobulin kappa constant region
D: Dihydrofolate reductase
VH: C10 heavy chain variable region
G1: Human immunoglobulin gamma 1 constant region
N2: Neomycin phosphotransferase exon 2

* $p<0.05$
** $p<0.01$
*** $p<0.005$
**** $p<0.001$
student-t

ANTI FGF23 ANTIBODY AND A PHARMACEUTICAL COMPOSITION COMPRISING THE SAME

CROSS-REFERENCE TO RELATED APPLICATIONS

This application is a divisional application of U.S. application Ser. No. 13/019,557, filed Feb. 2, 2011, which is a continuation application of U.S. application Ser. No. 12/030,593, filed Feb. 13, 2008, which claims priority from Japanese Application No. 2007-034018 filed Feb. 14, 2007. The subject matter of each of the above-referenced applications is incorporated in entirety by reference.

The instant application contains a Sequence Listing which has been submitted in ASCII format via EFS-WEB and is hereby incorporated by reference in its entirety. Said ASCII copy, created on Jan. 30, 2016, is named sequence.txt and is 30 KB.

BACKGROUND OF THE INVENTION

1. Field of the Invention

The present invention relates to an anti-FGF23 antibody which specifically binds to an FGF23 antigen. Furthermore, the present invention relates to an agent for prevention or treatment of mineral metabolic disorders due to excessive production of FGF23 or other causes comprising as an active ingredient the anti-FGF23 antibody. In particular, the present invention relates to an agent for treatment of hypophosphatemic rickets and osteomalachia treatment agent.

2. Background Art

Fibroblast growth factor was first purified from a bovine pituitary gland as a substance that stimulates an increase in fibroblast cell line NIH3T3. Since then, similar proteins have been identified various tissues, and a group of the substances compose a polypeptide family (FGF family). Up until now, 22 proteins have been identified in vertebrates as belonging to the FGF family. With regard to the biological activity of these proteins, not only do they have fibroblast growth activity, but these proteins are also known to have divergent actions such as growth of the mesoblast and the neuroectoderm, and angiogenesis action, and limb bud formation in the developmental stage. FGF is also varied in the gene expression site and expression time. They are often expressed only at certain sites only in the developmental stage or in adults. At least 4 genes encoding the FGF receptor are known, FGFR1, FGFR2, FGFR3, and FGFR4. In addition, with regards to FGFR1, FGFR2, and FGFR3, it is known that there are receptor proteins for each with differing extracellular domains due to differences in splicing. In addition, heparin and heparan sulfate proteoglycan are known to control the action by interaction with FGF and FGF receptors. In addition, there are many, which, due to structural similarities, belong to the FGF family, but whose biological activities and receptor binding properties and the like have not been known. The characteristics of this FGF family have been summarized in a review (see Ornitz, D. et al., Genome biology, 2: 3005.1-3005.12, 2001).

FGF23 (in general, may also be represented as FGF-23) was cloned initially from a mouse by a database search using homology with FGF15 and the PCR method. Further, human FGF23 was cloned by using the sequence homology with mouse FGF23. Human FGF23 is a polypeptide with 251 amino acid residues. In addition, as the secretory signal sequence, an amino acid sequence at amino terminal side up to 24 amino acids is predicted to be cleaved at the time of secretion (see Yamashita, T. et al., Biochem. Biophy. Res. Commun., 277: 494-498, 2000). Next, in research on autosomal dominant hypophosphatemic rickets/osteomalachia (henceforth referred to as ADHR), the mutated gene region in ADHR patients was narrowed down and with advancement in the identification of the responsible gene, a missense mutation in the FGF23 gene was discovered characteristically in ADHR patients (see White, K. E. et al., Nature Genet., 26: 345-348, 2000). With this discovery, there was a strong suggestion that FGF23 was physiologically important in the body. On the other hand, what determined the biological activity of FGF23 was research into neoplastic osteomalachia which is one of the hypophosphatemia rickets and osteomalachia diseases. In this disease, the culprit neoplasm of the disease produces and secretes a liquid disease initiating factor, and it is thought that pathologies such as hypophosphatemia, osteomalachia and the like are caused by the disease initiating factor.

In the search for the disease initiating factor produced by this culprit neoplasm, FGF23 was cloned as a gene which is overexpressed in the tumor. Furthermore, by administering this factor, it was shown that hypophosphatemia and osteomalachia were reproduced (see Shimada, T. et al., Proc. Natl. Acad. Sci., 98: 6500-6505, 2001 and International Publication Number WO02/14504 pamphlet). Based on this research, FGF23 has been shown to be related in the metabolic control related to phosphorus and calcium in the body. In addition, it was suggested that this acts as a systemic factor which expresses its action by circulating in the body. Furthermore, later research also showed that the blood of actual neoplastic osteomalachia patients had a higher value of FGF23 concentration as compared to healthy subjects (see Yamazaki, Y. et al., J. Clin. Endocrinol. Metab., 87: 4957-4960, 2002 and Jonsson, K. B., et al., N. Engl. J. Med., 348: 1656-1663, 2003).

In addition, X-linked hypophosphatemic rickets (henceforth referred to as XLH) is a disease which is known to have a similar presentation as ADHR and neoplastic osteomalachia in terms of clinical findings. In this disease as well, the FGF23 concentration in the blood was shown to be at a high value (see Yamazaki, Y. et al., J. Clin. Endocrinol. Metab., 87: 4957-4960, 2002 and Jonsson, K. B., et al., N. Engl. J. Med., 348: 1656-1663, 2003).

In other words, the cause for vitamin D resistant rickets and osteomalachia which were observed in neoplastic osteomalachia, XLH, and the like had been previously unknown, but the secreted disease causing factor was shown to be FGF23. Furthermore, with regard to other mineral metabolic diseases such as fibrous dysplasia, McCune-Albright syndrome, autosomal recessive hypophosphatemia rickets, and the like, high concentrations of FGF23 in the blood have been reported to be associated with hypophosphatemia and rickets and osteomalachia (See Riminucci, M. et al., J. Clin. Invest., 112: 683-692, 2003; Yamamoto, T. et al., J. Bone Miner. Metab., 23: 231-237, 2005; Lorenz-Depiereux, B. et al., Nat. Genet., 38: 1248-1250, 2006).

From the above report, the condition of having excessive FGF23 in the body has been shown to induce hypophosphatemia and the accompanying rickets and osteomalachia and the like. Furthermore, for chronic renal insufficiency hyperphosphatemia, abnormally high serum FGF23 values have been reported. Excessive FGF23 has been suggested to be possibly related to a portion of the mineral metabolic diseases during renal insufficiency (see Gupta, A. et al., J. Clin. Endocrinol. Metab., 89: 4489-4492, 2004 and Larsson, T. et al., Kidney Int., 64: 2272-2279, 2003). With regard to these diseases induced due to excessive FGF23, suppressing the action of FGF23 or removing FGF23 is thought to be a possible way to treat the diseases. Up to now, anti-FGF23 mouse monoclonal antibody has been reported to be a way to suppress the action of FGF23 (see Yamashita, T. et al., Biochem. Biophy. Res. Commun., 277: 494-498, 2000). When the anti-FGF23 mouse monoclonal antibody 2C3B and 3C1E used in this report were administered to normal mice, the function of the endogenous mouse FGF23 was inhibited, and the phosphorus excretion from the kidney was suppressed. By fluctuating the expression of vitamin D-metabolizing enzyme in the kidney, this was shown to result in increased concentrations for phosphorus and 1α, 25 dihydroxy vitamin D (henceforth referred to as 1,25D) in the serum. Furthermore, repeated administration of anti-FGF23 mouse monoclonal antibody was conducted on Hyp mouse which is a model mouse for XLH which has a high serum concentration of FGF23 and has hypophosphatemia and has bone elongation dysfunction and calcification dysfunction. As a result, in the Hyp mice, a rise in the phosphorus concentration in the blood was seen, and in addition, there were improvements in bone elongation dysfunction and calcification dysfunction. From these results, the use of FGF23 action suppressing antibody was thought to be appropriate as a medicine for FGF23 excess diseases. However, the 2C3B and 3C1E antibodies used in this report are mouse-derived antibodies. Mouse antibodies which are recognized as foreign by human host initiates a so-called "human anti-mouse antibody" (in other words HAMA) response, and there may be situations where serious side-effects are seen (see Van Kroonenbergh, M. J. et al., Nucl. Med. Commun.9: 919-930, 1988).

In order to avoid this type of problem, one approach was to develop a chimera antibody (see European Patent Application Publication Number 120694 Specification and European Patent Application Publication Number 125023 Specification). Chimera antibodies include a portion of antibody derived from 2 or more species (for example, variable region of the mouse antibody and the constant region of the human antibody and the like). The advantage of this type of chimera antibody is that the binding to the antibody which was the characteristic of the original mouse antibody is maintained, but on the other hand, "a human-anti chimera antibody" (in other words "HACA") response is still induced (see Bruggemann, M. et al., J. Exp. Med., 170: 2153-2157, 1989).

Furthermore, a recombinant antibody has been developed where only a portion of the substituted antibody is a complementarity determining region (CDR) (see British Patent Number GB2188638A specification and U.S. Pat. No. 5585089 specification). Using CDR transplant technology, an antibody consisting of mouse CDR, the framework of the human variable region and constant region (in other words "humanized antibody") was produced (see Riechmann, L. et al., Nature, 332: 323-327, 1988). It has been known that using this method, anti-FGF23 mouse antibody such as 2C3B antibody can be humanized by substituting mouse antibody with a human antibody sequence. However, when humanized, there is the possibility that the affinity to the antigen may be reduced. In addition, for the current treatment of hypophosphatemia rickets in XLH and the like, the main method is periodic oral administration of Vitamin D formulation and phosphoric acid. However, there is the problem that the patients are forced to have a substantial burden due to the size of each dose and the dosage frequency per day. Therefore, in order to lessen the burden on the patients and their families, a hypophosphatemia treatment drug which shows a sustained raising action for serum phosphate concentration and serum 1,25D concentration is desired in order to extend the time between doses.

SUMMARY OF THE INVENTION

The object of the present invention is to provide human antibody against FGF23 and to provide a pharmaceutical composition such as an agent for prevention or treatment or the like with few side effects by using the antibody to suppress the action of FGF23 and thereby preventing or treating disease.

Furthermore, the object of the present invention is to provide an antibody which is an anti-FGF23 antibody which can be used as a hypophosphatemia treatment medicine having a more sustained raising action for serum phosphate concentration and serum 1,25D concentration with a single dose as compared to existing anti-FGF23 antibodies. Another object of the present invention is to provide a pharmaceutical composition such as an agent for prevention or treatment of a disease related to FGF23 using this antibody.

Currently, the mainstream treatment method for hypophosphatemia rickets is oral administration of vitamin D formulation together with phosphate periodically several times a day. However, because of the large amount of each dose and the frequency of doses per day, there is the problem that the patients are forced to have a large burden. The anti-FGF23 human monoclonal antibody, the C10 antibody, obtained by the present invention is shown to have a more sustained raising action for the blood phosphate concentration and 1,25D concentration, in other words, a stronger FGF23 neutralizing activity. With a single administration of the C10 antibody in the present research, there was observed a sustained raising action for serum phosphate concentration and serum 1,25D concentration. This suggests that as compared to the current treatment for hypophosphatemia, the C10 antibody has the potential for being a dramatically superior treatment.

The present invention is as follows.

[1] An antibody against human FGF23 or a functional fragment thereof, comprising a heavy chain variable region and/or a light chain variable region of an antibody produced by hybridoma C10 (Accession No. FERM BP-10772)

[2] An antibody against human FGF23 or a functional fragment thereof, comprising a heavy chain amino acid sequence shown by an amino acid sequence from Q at position 20 to S at position 136 of SEQ ID NO: 12 and/or a light chain amino acid sequence shown by an amino acid sequence from A at position 23 to K at position 128 of SEQ ID NO: 14.

[3] An antibody against human FGF23 or a functional fragment thereof, wherein: the antibody against human FGF23 or the functional fragment thereof contains a heavy chain variable region and/or a light chain variable region amino acid sequence; and the heavy chain variable region amino acid sequence is shown by an amino acid sequence from Q at position 20 to S at position 136 of SEQ ID NO: 12; and the light chain variable region amino acid sequence is shown by an amino acid sequence from A at position 23 to K at position 128 of SEQ ID NO: 14.

[4] An antibody against human FGF23 produced by hybridoma C10 (Accession No. FERM BP-10772) or a functional fragment thereof.

[5] An antibody or a functional fragment thereof binding to all or part of epitope on human FGF23, to which an antibody produced by hybridoma C10 (Accession No. FERM BP-10772) binds.

[6] The antibody against human FGF23 or a functional fragment thereof, comprising a heavy chain variable region of the above [3] having any one of complementarity determining region (CDR) 1 shown by the amino acid sequence of SEQ ID NO: 40, CDR2 shown by the amino acid sequence of SEQ ID NO: 41 and CDR3 shown by the amino acid sequence of SEQ ID NO: 42, or a heavy chain variable region of the above [3] having all of the above.

[7] The antibody against human FGF23 or a functional fragment thereof, comprising a light chain variable region of the above [3] having any one of CDR 1 shown by the amino acid sequence of SEQ ID NO: 43, CDR2 shown by the amino acid sequence of SEQ ID NO: 44 and CDR3 shown by the amino acid sequence of SEQ ID NO: 45, or a light chain variable region of the above [3] having all of the above.

[8] An antibody against human FGF23 or a functional fragment thereof, wherein the antibody against human FGF23 or the functional fragment thereof contains a heavy chain variable region having any one of complementarity determining region (CDR) 1 shown by the amino acid sequence of SEQ ID NO: 40, CDR2 shown by the amino acid sequence of SEQ ID NO: 41 and CDR3 shown by the amino acid sequence of SEQ ID NO: 42, or a heavy chain variable region having all of the above; and a light chain variable region having any one of complementarity determining region (CDR) 1 shown by the amino acid sequence of SEQ ID NO: 43, CDR2 shown by the amino acid sequence of SEQ ID NO: 44 and CDR3 shown by the amino acid sequence of SEQ ID NO: 45, or a light chain variable region having all of the above.

[9] The antibody against human FGF23 or a functional fragment thereof as described in any one of [1]-[8], wherein the functional fragment is a peptide fragment selected from the group consisting of Fab, Fab', F (ab')2, disulfide stabilized Fv (dsFv), dimerized V region (diabody), single chain Fv (scFv) and CDR.

[10] The antibody against human FGF23 or a functional fragment thereof, as described in any one of [1]-[8], comprising: a heavy chain and/or light chain having an amino acid sequence in which one or several amino acids are deleted, substituted or added.

[11] The antibody against human FGF23 as described in any one of [1]-[10], wherein the class of the antibody is IgG, IgA, IgE, or IgM.

[12] The antibody against human FGF23 as described in [11], wherein the subclass of the antibody is IgG1, IgG2, IgG3, or IgG4.

[13] A pharmaceutical composition, comprising as an active ingredient, the antibody against human FGF23 or a functional fragment thereof as described in any one of [1]-[12].

[14] A pharmaceutical composition which can control phosphorus metabolism and/or vitamin D metabolism by FGF23 and comprises, as an active ingredient, the antibody against human FGF23 or a functional fragment thereof as described in any one of [1]-[12].

[15] A pharmaceutical composition for prevention or treatment of diseases that are associated with mineral metabolism disorders comprising as an active ingredient, the antibody against human FGF23 or a functional fragment thereof as described in any one of [1]-[12].

[16] The pharmaceutical composition as described in [15], wherein the disease which is associated with mineral metabolism abnormalities is selected from the group consisting of neoplastic osteomalachia, ADHR, XLH, fibrous dysplasia, McCune-Albright syndrome, and autosomal recessive hypophosphatemia.

[17] A pharmaceutical composition for prevention or treatment of a disease selected from the group consisting of osteoporosis, rickets, hypocalcaemia, hypocalcaemia, heterotrophic calcification, osteosclerosis, Paget's disease, hyperparathyroidism, hypoparathyroidism, and pruritis, comprising as an active ingredient, the antibody against human FGF23 or a functional fragment thereof as described in any one of [1]-[12].

[18] A hybridoma C10 (Accession No. FERM BP-10772).

[19] Nucleic acids which encode an amino acid sequence of a heavy chain variable region encoded by a base sequence from C at position 58 to A at position 408 represented by SEQ ID NO: 11.

[20] Nucleic acids which encode an amino acid sequence of a light chain variable region encoded by a base sequence from G at position 67 to A at position 384 represented by SEQ ID NO: 13.

[21] A vector containing the nucleic acid described in [19] or [20].

[22] A host cell containing the vector described in [21].

[23] A method for producing an antibody against human FGF23 or a functional fragment thereof, comprising the step of culturing the host cell described in [22] to express an antibody against human FGF23 or a functional fragment thereof.

BRIEF DESCRIPTION OF THE DRAWINGS

FIG. 2 shows the nucleotide sequence (SEQ ID NO: 30) and amino acid sequence (SEQ ID NO: 31) of the antibody heavy chain gene in N5KG1_C10_LH. The amino acid sequence surrounded by a rectangular line represents the secretion signal sequence (leader sequence).

FIG. 3 shows the nucleotide sequence (SEQ ID NO: 32) and amino acid sequence (SEQ ID NO: 33) of the antibody light chain gene in N5KG1_C10_LH. The amino acid sequence surrounded by a rectangular line represents the secretion signal sequence (leader sequence).

FIG. 4 shows the structure of C10 expression vector.

hFGF23 (−SP): Human FGF23 gene having no specific signal peptide code region,
Ck: constant region of mouse Igκ gene,
loxpv-puro: puromycin resistance gene having loxPV sequence which is a partially mutated loxP sequence at both ends thereof,
loxp-neor: neomycin resistance gene having loxP sequence at both ends thereof,
Ck3' probe: Southern blotting analysis probe for selection of clones having hFGF23 (−SP) + loxpv-puror gene introduced and having loxpv-puror gene deleted,
3'KO-probe: Southern blotting analysis probe for selection of clones having loxp-neor gene introduced and deleted, and
E: EcoRI restriction enzyme site.

Figure 13:
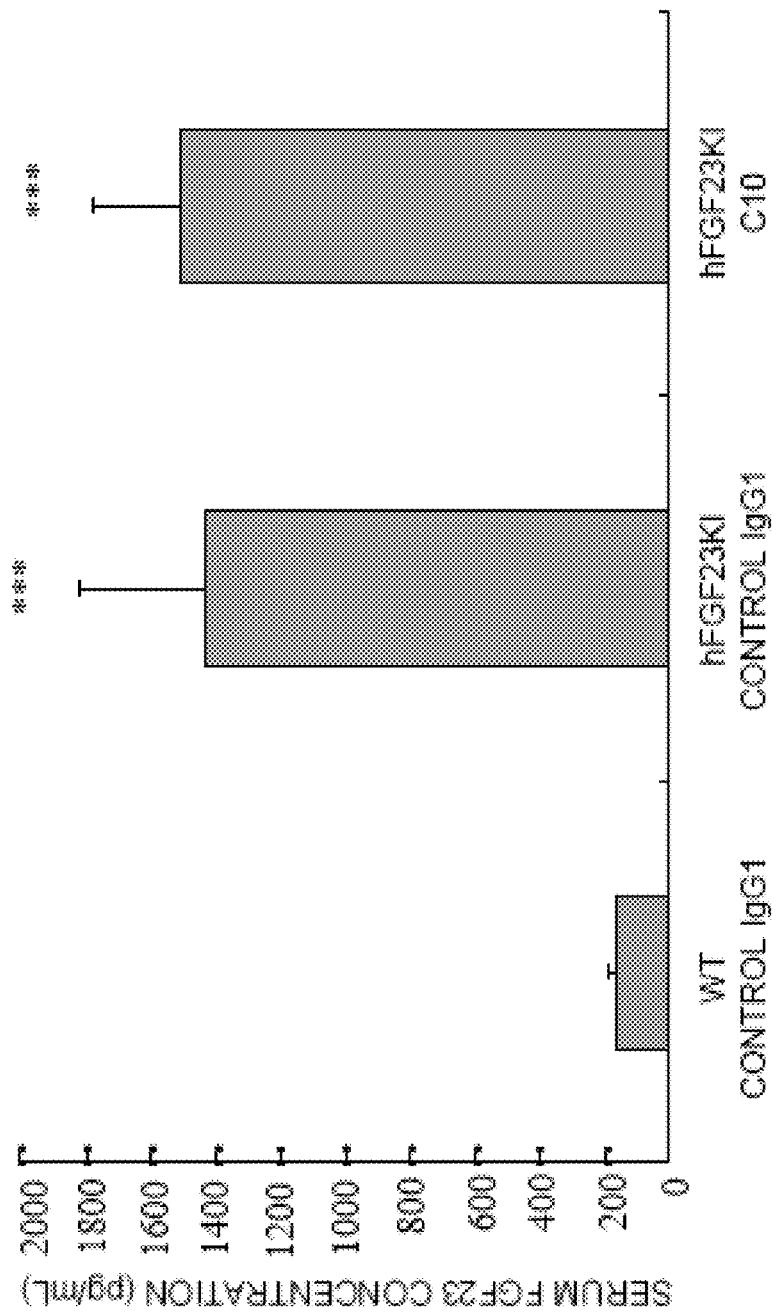

FIG. 13 is a graph showing the serum FGF23 concentration 7 days before the control antibody or C10 antibody administration. Measured values are shown in average +/− standard error. Further, when significant difference test between the WT mice group and the test groups was conducted using Student's t-test, groups found to be significant difference (p<0.001) are marked with *** on the graph.

Figure 14:
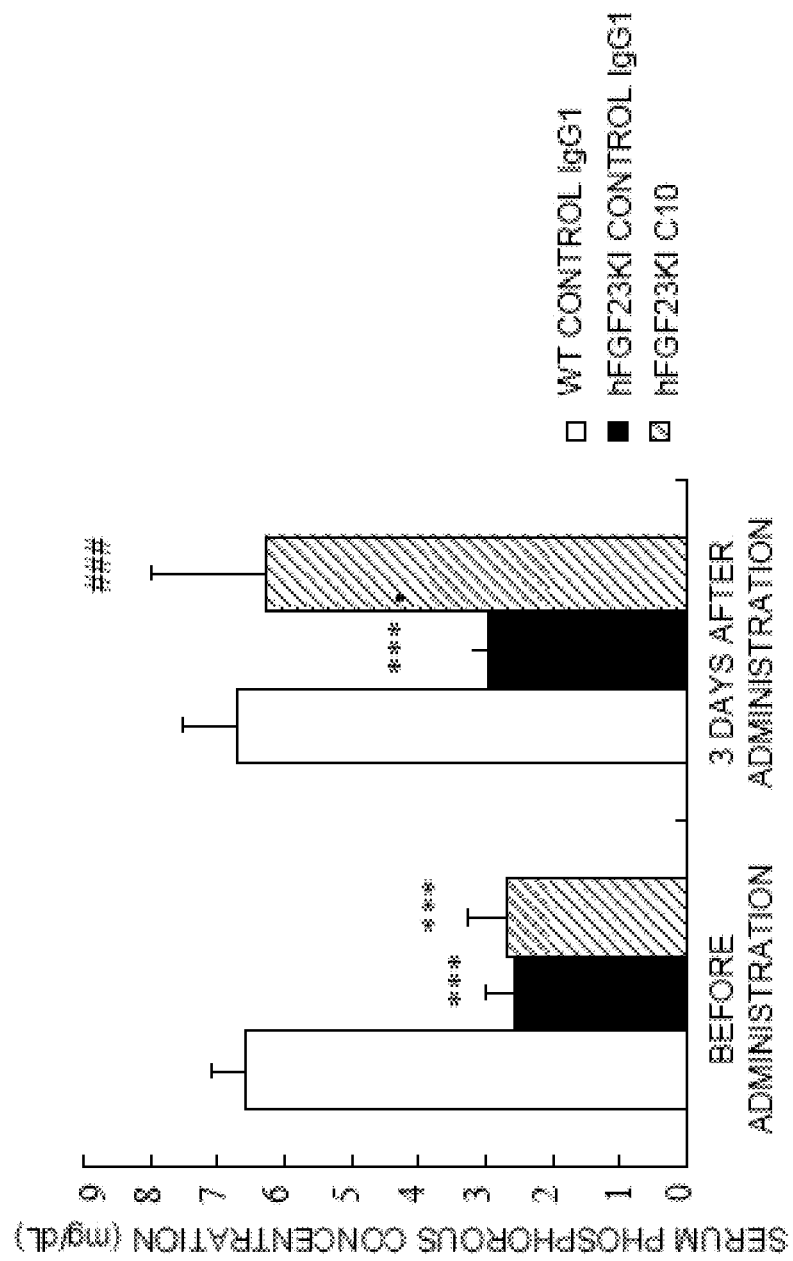

FIG. 14 is a graph showing the serum phosphorous concentration 7 days before the control antibody or C10 antibody administration and 3 days after the first administration of control antibody or C10 antibody. Measured values are shown in average +/− standard error. Further, when significant difference test between the WT mice group and the test groups was conducted in one day using Student's t-test, groups found to be significant difference (p<0.001) are marked with *** on the graph. In addition, when significant difference test between the hFGF23KI mouse control antibody administered group and the test groups was conducted in one day, hFGF23KI mouse C10 antibody administered groups found to be significant difference (p<0.001) are marked with ### on the graph.

Figure 15:
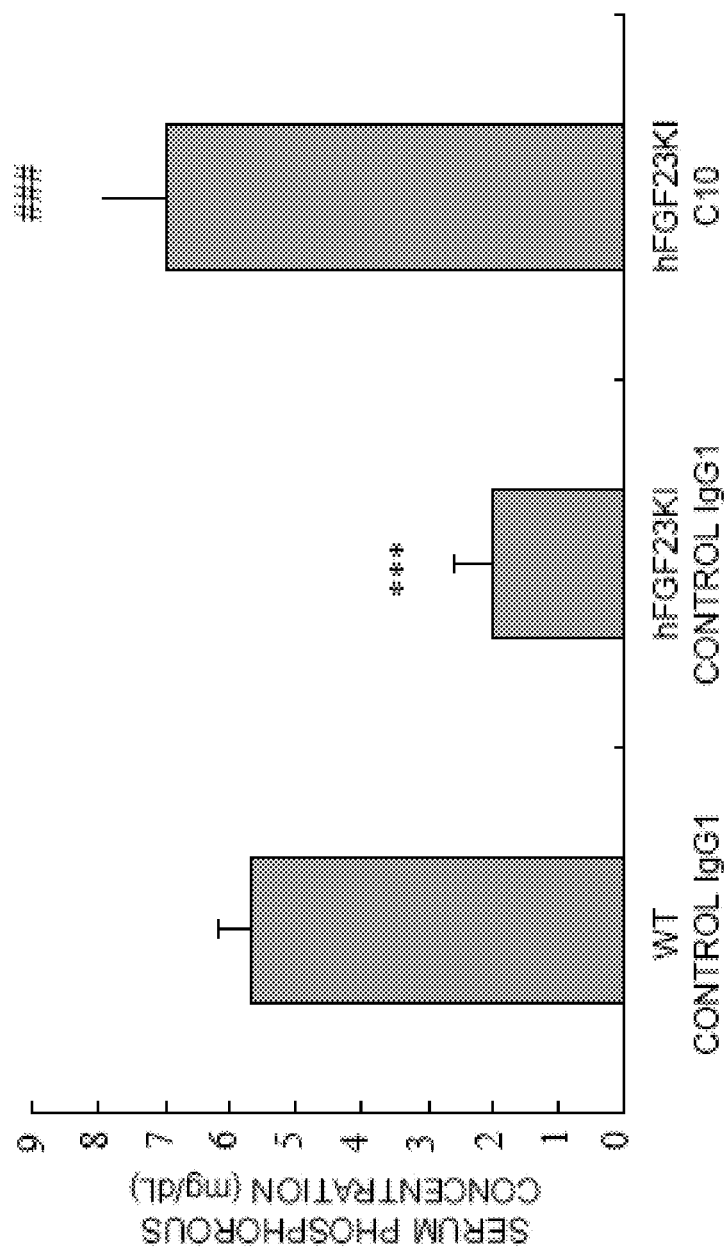

FIG. 15 is a graph showing the serum phosphorous concentration 1 day after the fifth administration of control antibody or C10 antibody. Measured values are shown in average +/− standard error. Further, when significant difference test between the WT mice group and the test groups was conducted using Student's t-test, groups found to be significant difference (p<0.001) are marked with *** on the graph. In addition, when significant difference test between the hFGF23KI mouse control antibody administered group and the test groups was conducted, hFGF23KI mouse C10 antibody administered groups found to be significant difference (p<0.001) are marked with ### on the graph.

Figure 16:
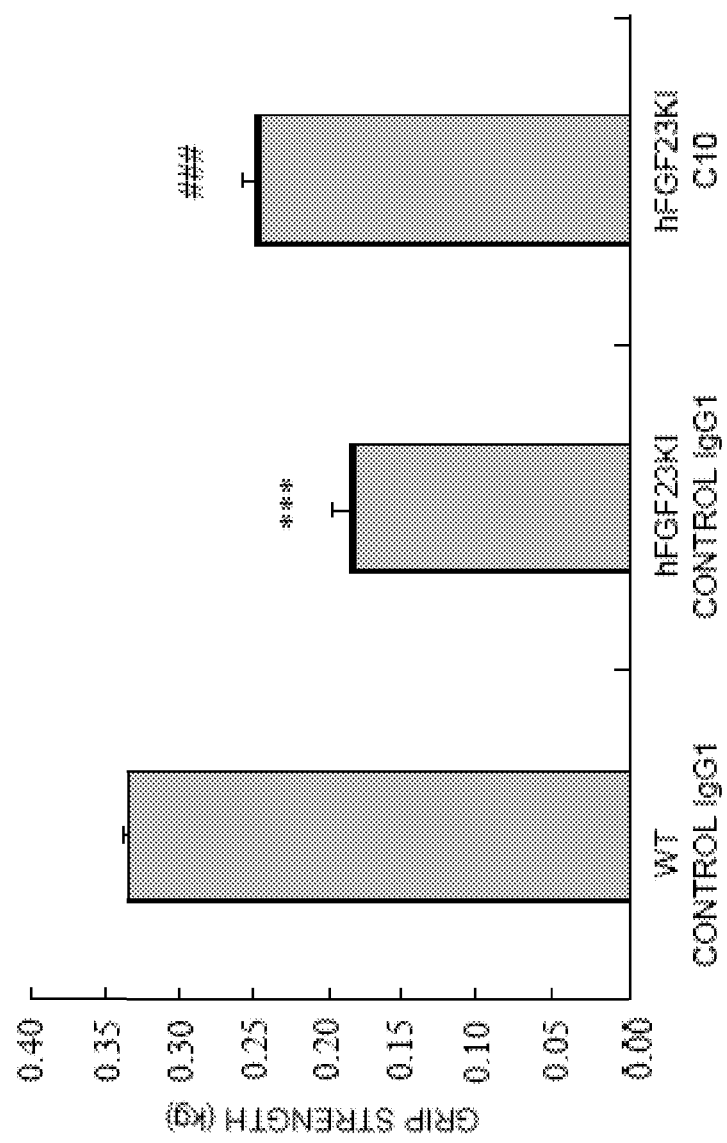

FIG. 16 is a graph showing the grip strength 1 day after the fourth administration of control antibody or C10 antibody. Measured values are shown in average +/− standard error. Further, when significant difference test between the WT mice group and the test groups was conducted using Student's t-test, groups found to be significant difference (p<0.001) are marked with *** on the graph. In addition, when significant difference test between the hFGF23KI mouse control antibody administered group and the test groups was conducted, hFGF23KI mouse C10 antibody administered groups found to be significant difference (p<0.001) are marked with ### on the graph.

Figure 17:
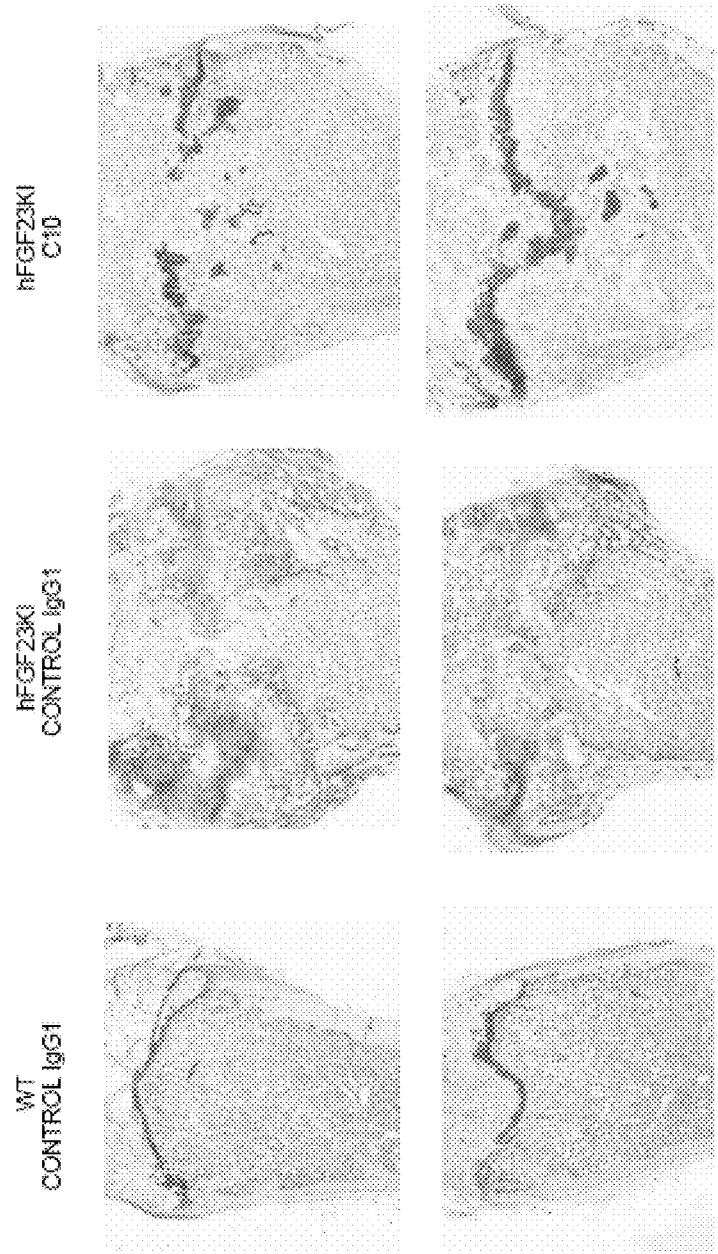

FIG. 17 is a picture showing the histological staining image of femur collected from mice 1 day after the fifth administration of control antibody or C10 antibody, wherein the staining was performed by Villanueva-Goldner method.

Figure 18:
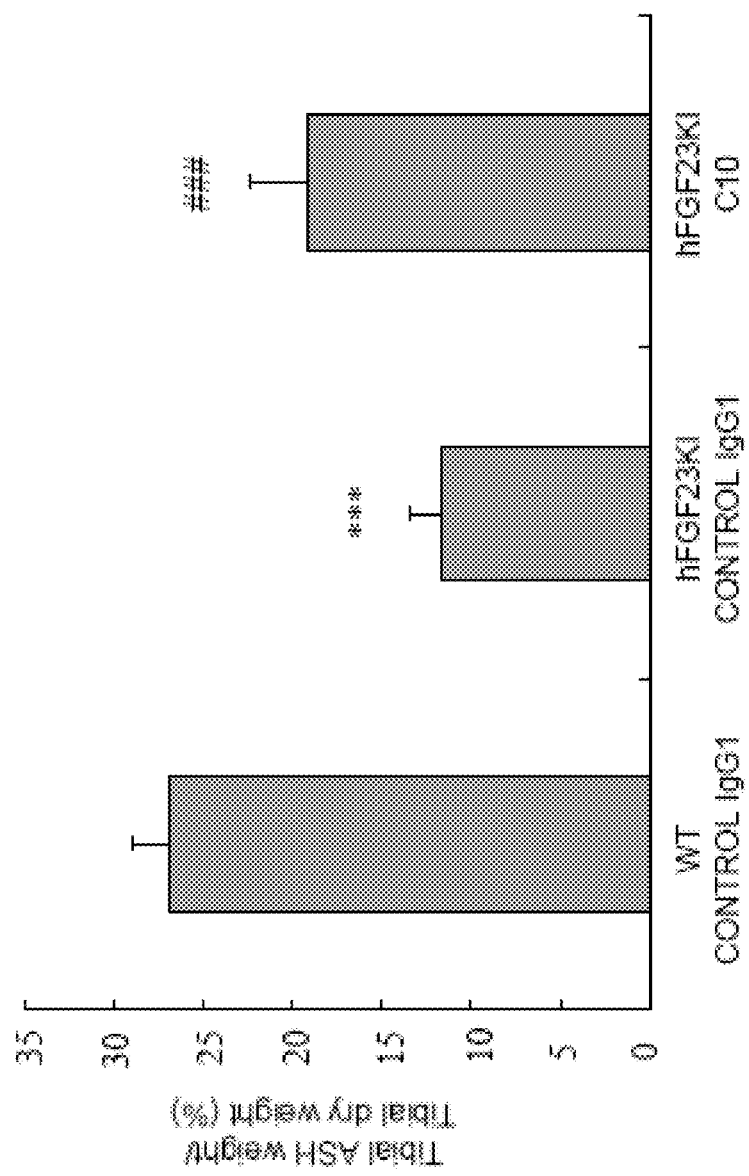

FIG. 18 is a graph showing the ratio of ash weight to dry weight of tibia collected from mice 1 day after the fifth administration of control antibody or C10 antibody. Measured values are shown in average +/− standard error. Further, when significant difference test between the WT mice group and the test groups was conducted using Student's t-test, groups found to be significant difference (p<0.001) are marked with *** on the graph. In addition, when significant difference test between the hFGF23KI mouse control antibody administered group and the test groups was conducted, hFGF23KI mouse C10 antibody administered groups found to be significant difference (p<0.001) are marked with ### on the graph.

DETAILED DESCRIPTION OF THE PREFERRED EMBODIMENTS

Below, by clarifying the definitions for the terms used in the present invention, we will describe the present invention in detail.

I. Antibody of the Present Invention

1. Anti-FGF23 Antibody and its Functional Fragment

The antibody of the present invention is an antibody against FGF23 which is a member of the fibroblast growth factor (FGF) family.

In the present invention, "antibody against FGF23" is an antibody which binds to FGF23 or a portion thereof, an antibody which is reactive to FGF23 or a portion thereof, or an antibody which recognizes FGF23 or a portion thereof. Antibody against FGF23 is also termed an anti-FGF23 antibody. In the present invention, an antibody is an immunoglobulin in which all of the regions which construct the immunoglobulin of the heavy chain variable region and heavy chain constant region and the light chain variable region and light chain constant region are derived from a gene which encodes the immunoglobulin. The antibody is preferably a monoclonal antibody. Here, a portion of FGF23 signifies a partial amino acid sequence of a full-length amino acid sequence of FGF23 represented by SEQ ID NO: 4 and is a fragment peptide of FGF 23 comprising a continuous amino acid sequence. Preferably, the antibody contains the amino acid sequence from Q at position 20 to S at position 136 of SEQ ID NO: 12 and/or the amino acid sequence from A at position 23 to K at position 128 of SEQ ID NO: 14.

More preferably, the antibody is an antibody produced by hybridoma C10. SEQ ID NO: 12 is the amino acid sequence that comprises the leader sequence of the heavy chain variable region of the antibody against FGF23. The amino acid sequence from Q at position 20 to S of number 136 of SEQ ID NO: 12 is the mature portion of the amino acid sequence with the leader sequence portion removed. In addition, SEQ ID NO: 14 is the amino acid sequence that comprises the leader sequence of the light chain variable region of the antibody against FGF23. The amino acid sequence from A at position 23 to K at position 128 of SEQ ID NO: 14 is the mature portion of the amino acid sequence with the leader sequence removed. With regard to the class of antibody, immunoglobulin G (IgG), immunoglobulin A (IgA), immunoglobulin E (IgE), and immunoglobulin M (IgM) are used. Preferably, it is IgG. Furthermore, for the IgG subclass, IgG1, IgG2, IgG3, IgG4 are used. It is preferably IgG1, IgG2, and IgG4. More preferably, it is IgG1.

The antibody of the present invention also includes an anti-FGF23 antibody which comprises an amino acid sequence of a novel complementarity determining region (CDR).

A CDR is present in the variable region of an antibody, and the part is responsible for the specificity of antigen recognition. The part other than the CDR in the variable region has a role in maintaining the structure of the CDR, and is referred to as the framework region (FR). A constant region is present in the C terminal side of a heavy chain and a light chain, and is referred to as the heavy chain constant region (CH) and the light chain constant region (CL), respectively.

Three complementarity determining regions are present in the heavy chain variable region, which are a first complementarity determining region (CDR1), a second complementarity determining region (CDR2), and a third complementarity determining region (CDR3). The three complementarity determining regions in the heavy chain variable region are collectively referred to as the heavy chain complementarity determining region. Similarly, three complementarity determining regions are present in the light chain variable region, which are a first complementarity determining region (CDR1), a second complementarity determining region (CDR2), and a third complementarity determining region (CDR3). The three complementarity determining regions in the light chain variable region are collectively referred to as the light chain complementarity determining region. The sequences of these CDRs can be determined by using the methods described in Sequences of Proteins of Immunological Interest, US Dept. Health and Human Services (1991) and the like.

The antibody of the present invention preferably has at least any one or all of CDR1 shown by SEQ ID NO: 40, CDR2 shown by SEQ ID NO: 41, and CDR3 shown by SEQ ID NO: 42 as the heavy chain complementarity determining region. In addition, the antibody of the present invention preferably has at least any one or all of CDR1 shown by SEQ ID NO: 43, CDR2 shown by SEQ ID NO: 44, and CDR3 shown by SEQ ID NO: 45 as the light chain complementarity determining region. More preferably, the antibody of the present invention is an antibody which binds to FGF23 and has CDR1 shown by SEQ ID NO: 40, CDR2 shown by SEQ ID NO: 41, and CDR3 shown by SEQ ID NO: 42 as the heavy chain complementarity determining region, and CDR1 shown by SEQ ID NO: 43, CDR2 shown by SEQ ID NO: 44, and CDR3 shown by SEQ ID NO: 45 as the light chain complementarity determining region.

The CDR sequence of the antibody of the present invention is not specifically limited. However, the antibody of the present invention is an antibody preferably comprising any one or more CDRs, more preferably three CDRs of the heavy chain, and even more preferably six CDRs of the CDR sequences represented by SEQ ID NO: 40 through 45. The amino acid sequence other than the CDR is not specifically limited. The antibody of the present invention includes so called CDR transplantation antibodies, wherein the amino acid sequence other than the CDR is derived from other antibodies, and particularly antibodies in other species. Among these, a humanized antibody or human antibody, wherein the amino acid sequence other than the CDR is derived from human, is preferred. An addition, deletion, substitution and/or insertion of 1 amino acid residue or more can be introduced into the FR according to need. A publicly known method can be applied as the method for producing a humanized antibody or human antibody.

"Functional fragment" is a portion of an antibody (partial fragment) and has one or more of the actions of the antibody to the antigen. In other words, it refers to a fragment which retains binding ability to the antigen, reactivity to the antigen, or recognition capability to the antigen. Examples include Fv, disulfide stabilized Fv (dsFv), single chain Fv (scFv), and polymers of these and the like. Stated more specifically, examples include peptides which contain Fab, Fab', F (ab')2, scFv, diabody, dsFv, and CDR [D. J. King., Applications and Engineering of Monoclonal Antibodies., 1998 T. J. International Ltd].

Of the fragments which are obtained by treating an antibody which binds to FGF23 with the protease papain, Fab is the antibody fragment of molecular weight approximately 50,000 with antigen binding activity, in which approximately half of the amino-terminal side of the H chain with all of the L chain by a disulfide bond.

The Fab of the present invention can be obtained by treating the antibody which binds to FGF23 with the protease papain. Alternatively, Fab can be produced by inserting DNA which encodes Fab of the antibody into an expression vector for prokaryotic organisms or an expression vector for eukaryotic organisms and expressing this vector by introducing into a prokaryotic organism or eukaryotic organism.

Of the fragments obtained by treating IgG with the protease pepsin, F (ab')2 is the antibody fragment of molecular weight approximately 100,000 with antigen binding activity and which is larger than that of Fab bonded via disulfide bonds of the hinge region.

The F (ab')2 of the present invention can be obtained by treating antibody that binds with FGF23 with the protease pepsin. Alternatively, it can be produced through a thioether bond or disulfide bond of Fab' described below.

Fab' is an antibody fragment of a molecular weight of approximately 50,000 having antigen binding activity and in which the disulfide bond of the hinge region of the above F (ab')2 is cleaved.

Fab' of the present invention is obtained by treating F (ab')2 of the present invention, which binds to FGF23, with a reducing agent dithiothreitol. Alternatively, DNA which encodes the Fab' fragment of this antibody is inserted into an expression vector for prokaryotic organisms or into an expression vector for eukaryotic organisms, and this vector is introduced into prokaryotic organisms or eukaryotic organisms and thereby is expressed to produce Fab'.

scFv is an antibody fragment having antibody binding activity with a single heavy chain variable region (hereinafter referred to as VH) and a single light chain variable region (henceforth written as VL) which are linked using a suitable peptide linker (henceforth written as P) and is a VH-P-VL or VL-P-VH polypeptide.

The scFv of the present invention can be produced by obtaining the cDNA which encodes VH and VL of the antibody of the present invention which binds with FGF23 and constructing the DNA which encodes scFV and inserting the DNA into the expression vector for prokaryotic organisms or the expression vector for eukaryotic organisms and introducing and expressing the expression vector in prokaryotic organisms or eukaryotic organisms.

A diabody is an antibody fragment in which scFv is dimerized and is an antibody fragment having a bivalent antibody binding activity. Each binding activity of the bivalent antibody can be the same or different.

The diabody of the present invention can be produced by obtaining the cDNA which encodes the VH and VL of the antibody of the present invention which binds to FGF23, constructing the DNA which encodes scFV such that the length of the amino acid sequence for the peptide linker is 8 residues or less, inserting this DNA into an expression vector for prokaryotic organism or expression vector for eukaryotic organism, and expressing this expression vector by introducing into a prokaryotic organism or eukaryotic organism.

In dsFv, 1 amino acid residue in each of VH and VL is substituted with a cystine residue, and the polypeptides are bonded through a disulfide bond between these cysteine residues. The amino acid residue which is substituted with the cysteine residue can be selected based on the predicted tertiary structure of the antibody according to the method indicated by Reiter et al (Protein Engineering, 7: 697-704, 1994).

The dsFv of the present invention can be produced by obtaining the cDNA which encodes VH and VL of the antibody of the present invention which binds to FGF23, constructing the DNA which encodes the dsFv, inserting this DNA into an expression vector for a prokaryotic organism or an expression vector for a eukaryotic organism, and introducing and expressing this expression vector in a prokaryotic organism or eukaryotic organism.

The peptide which comprises CDR is constructed comprising at least 1 region or more of CDR of VH or VL. Peptides which comprise multiple CDR's can be linked together directly or through a suitable peptide linker.

The peptide which comprises the CDR of the present invention can be produced by constructing a DNA which encodes the CDR of the VH and VL of the antibody of the present invention which binds to FGF23, inserting this DNA into an expression vector for prokaryotic organisms or expression vector for eukaryotic organisms, and introducing and expressing this expression vector in prokaryotic organisms or eukaryotic organisms.

In addition, the peptide which contains CDR can be produce by a chemical synthesis method such as Fmoc method (fluorenylmethyloxycarbonyl method) and tBoc method (t-butyloxycarbonyl method) and the like.

Furthermore, "functional fragment" is a fragment of the antibody which can bind to the antigen (FGF23). Preferably, the "functional fragment" is a fragment which can bind to FGF23 and comprises an amino acid sequence from Q at position 20 to S at position 136 of SEQ ID NO: 12, and/or an amino acid sequence from A at position 23 to K at position 128 of SEQ ID NO: 14. Preferably, the "functional fragment" is a fragment which comprises at least one or all of CDRs represented by SEQ ID NO: 40 through 45 and can bind to FGF23. More preferably, the "functional fragment" is derived from the variable region of an antibody produced by hybridoma C10 and is a fragment which can bind to FGF23.

The antibody of the present invention includes derivatives of the antibody in which radioisotopes, low molecular weight drugs, macromolecular drugs, proteins, and the like is bound chemically or through genetic engineering to the antibody against FGF23 of the present invention or functional fragments of the antibody.

The derivatives of the antibody of the present invention can be produced by bonding radioisotopes, low molecular weight drugs, macromolecular drugs, proteins and the like to the amino terminal side or carboxy terminal side of the H chain (heavy chain) or L chain (light chain) of the antibody against FGF23 of the present invention or the functional fragment of the antibody, to a suitable substituted group or side chain in the antibody or functional fragment of the antibody, and further, to a sugar chain in the antibody or functional fragment of the antibody and the like by chemical methods (Koutai Kogaku Nyuumon, Osamu Kanamitsu, Chijin Shokan, 1994) and the like.

In addition, the derivative of the antibody bonded with protein is produced by linking the DNA which encodes the antibody against FGF23 of the present invention and the functional fragment of the antibody and the DNA which encodes the protein to be bonded, inserting this DNA into an expression vector, and introducing and expressing the expression vector in a suitable host cell.

For the radioisotope, examples include 131I, 125I. For example, the radioisotope can be bonded to the antibody by the chloramine T method and the like.

Low molecular weight drugs include alkylating agents including nitrogen mustard, cyclophosphamide; antimetabolites such as 5-fluorouracil and methotrexate; antibiotics such as daunomycin, bleomycin, mitomycin C, daunorubicin and doxorubicin; plant alkaloids, such as vincristine, vinblastine and vindesine; anti cancer agents such as hormone agents such as tamoxifen and dexamethasone (Clinical oncology; Japanese Clinical Oncology Research Meeting, Japanese Journal of Cancer and Chemotherapy Co., 1996); steroids such as hydrocortisone, prednisone, and the like; non-steroid agents including aspirin and indomethacin; immunomodulators such as gold thiomalate, penicillamine, and the like; immunosuppressors such as cyclophosphamide, azathioprine, and the like; anti-inflammatories such as anti-histamines such as chlorpheniramine maleate, clemastine, and the like (Inflammation and anti-inflammatory treatment method, Ishiyaku Publishing Corp. Ltd., 1982). The bonding of the antibody with these low molecular weight drugs is conducted by known methods. Examples of methods for bonding daunomycin with antibody include a method for bonding between amino groups of the daunomycin and antibody via glutaraldehyde, and a method for bonding the amino group of daunomycin and carboxyl group of the antibody via water-soluble carbodiimide. By bonding these low molecular weight drugs with the antibody, a derivative of an antibody having the function of the low molecular weight drug is obtained.

For the macromolecular drug, examples include polyethylene glycol (hereinafter referred to as PEG), albumin, dextran, polyoxyethylene, styrene maleate copolymer, polyvinyl pyrrolidone, pyran copolymer, hydroxypropyl methacrylamide, and the like. By bonding these macromolecular compounds with antibody or a functional fragment of an antibody, the following effects are anticipated (1) the stability with respect to various chemical, physical, and biological factors is improved (2) half life in blood is dramatically extended, (3) immunogenicity is lost, antibody production is suppressed, and the like (Bioconjugate Pharmaceutical, Hirokawa Shoten, 1993). An example of a method for bonding PEG to an antibody is a method of reacting with PEG-modifying reagent (Bioconjugate Pharmaceutical, Hirokawa Shoten, 1993). Examples of PEG-modifying reagent include ε-amino group modifier of lysine (Laid-Open Patent Publication Number S61-178926), carboxyl group modifier of aspartic acid and glutamic acid (Laid-Open Patent Publication Number S56-23587), guanidino group modifier of arginine (Laid-Open Patent Publication Number H2-117920), and the like.

The antibody which has bonded to the protein can be obtained as a fusion antibody. In other words, the cDNA which encodes the antibody or a functional fragment of the antibody is linked with the cDNA which encodes a specific protein, and DNA which encodes the fused protein of the specific protein and antibody is constructed. This DNA is inserted into an expression vector for a prokaryotic organism or eukaryotic organism. This expression vector can be introduced and expressed in the prokaryotic organism or eukaryotic organism in order to produce the fused antibody which is bonded with the specific protein.

With regard to the antibody against FGF23 of the present invention or the functional fragment of the antibody, by taking measurements through immunological methods such as ELISA (Antibodies: A Laboratory Manual, Cold Spring Harbor Laboratory, Chapter 14, 1988; Monoclonal Antibodies: Principles and Practice, Academic Press Limited, 1996) or measuring the binding dissociation constant by biosensor Biacore (Journal of Immunological Methods, 145: 229-240, 1991), and measuring the inhibition activity (Nature, 444: 770-774, 2006) of the promoter activity of the Early growth response gene-1 by human FGF23 stimulation using klotho expression cells, human FGF23 binding activity and the activity of inhibiting the function of human FGF23 can be evaluated.

In the present invention, "human antibody" is defined as an antibody which is an expression product of an antibody gene derived from humans. Human antibody, as will be described later, can be obtained by introducing the human antibody gene locus and by administering antigen to transgenic animals having the ability to produce human antibody. Examples of these transgenic animals include mice. The method of creation of mice which can produce human antibody is described, for example, in International Publication Number WO02/43478 pamphlet.

For the antibody of the present invention, examples include an antibody (C10 antibody) produced by C10 hybridoma as will be described in Examples later. C10 hybridoma has had an international deposition based on the Budapest treaty with accession No. FERM ABP-10772 (a display for identification: C10) at the Patent Organism Depository Center (Central 6, 1-1 Higashi 1-chome, Tsukuba-shi, Ibaraki-ken, Japan) on Feb. 2, 2007 at the independent administrative institution of the Advanced Industrial Science and Technology.

The antibody or functional fragment of the present invention also included monoclonal antibodies or functional fragments thereof comprising the heavy chain and/or light chain consisting of amino acid sequences with 1 or several amino acid deletions, substitutions, and additions in each of the amino acid sequences for the heavy chain and/or light chain which constructs the antibody or functional fragment. Here, of the "1 or several", "several" is 9 or less, preferably 5 or less, and more preferably 3 or less. Having 2 is especially preferred. A partial modification (deletion, substitution, insertion, addition) of the amino acid as described previously can be introduced into the amino acid sequence of the antibody of the present invention or functional fragment by partially modifying the nucleotide sequence which encodes the amino acid sequence. Partial modification of this nucleotide sequence can be introduced using the conventional method of known site specific mutagenesis [Proc Natl Acad Sci USA., 81: 5662-5666, 1984]. The antibody of the present invention includes antibodies of all immunoglobulin classes and isotypes.

The antibody against FGF23 of the present invention can be produced by the following production method. For example, FGF23 or a portion of FGF23 or a conjugate of a portion of FGF23 and a suitable carrier substance for increasing antigenicity (for example, bovine serum albumin and the like) are immunized together with an adjuvant (Freund's complete or incomplete adjuvant and the like) as necessary into non-human mammals such as human antibody producing transgenic mice. For FGF23, natural FGF23 or recombinant FGF23 can be used. Alternatively, immune sensitization can be conducted by introducing the gene encoding FGF23 into an expression vector and expressing the FGF23 protein inside the animal. The monoclonal antibody is obtained by culturing the hybridoma obtained by fusing antibody producing cells obtained from immune sensitized animals and myeloma cells which do not have antibody production ability, and by selecting the clones which produce the monoclonal antibodies showing specific affinity for the antigen used for immunization.

The antibody of the present invention includes those that have been converted to a different subclass by genetic engineering modification that is known to those skilled in the art (for example, see European Patent Application EP314161). In other words, using DNA which encodes the variable region of the antibody of the present invention, an antibody which is of a subclass that is different from the original subclass can be obtained using genetic engineering methods.

2. Producing the Antibody of the Present Invention

Producing a monoclonal antibody includes the following steps. In other words, (1) the antigen protein which is to be used as the immunogen or the antigen protein expression vector is prepared, (2) after immunization by injecting the antigen inside the animal or by expressing the antigen inside the animal, blood is sampled and its antibody titer is assayed, and after determining the time for spleen isolation, antibody production cells are prepared, (3) Myeloma cells are prepared, (4) the antibody production cell and myeloma are fused, (5) the hybridoma group which produces the target antibody is selected, (6) the hibridomas are divided into a single cell clone (cloning), (7) optionally, the hybridoma is cultured to produce large amounts of monoclonal antibody, or animals in which the hybridoma has been transplanted are raised, and (8) the biological activity and the recognition specificity of the monoclonal antibody produced in this way is assayed, or the property as a labeling reagent are assayed.

Hereinafter, the production method for the anti-FGF23 monoclonal antibody is described in detail following the above process. However, the production method for this antibody is not limited to this method. For example, antibody producing cells and myeloma from other than spleen cells can also be used.

(1) Purification of the Antibody

Using genetic recombination technique, the DNA sequence which encodes FGF23 is integrated into a suitable expression plasmid. After FGF23 is produced in a host such as *E. coli* or an animal cell or the like, the purified FGF23 protein can be used. Because the primary structure of human FGF23 protein is known [GenBank accession No. AAG09917, SEQ ID NO: 4], a partial peptide from the amino acid sequence of FGF23 is chemically synthesized by methods known to those skilled in the art, and this can also be used as the antigen.

(2) Preparation Step of Antibody Producing Cell

The antigen obtained as mentioned in (1) is mixed with a adjuvant such as complete or incomplete Freund's adjuvant or aluminum potassium, and the mixture is immunized into experimental animals as an immunogen. For the experimental animals, transgenic mice having the ability to produce human derived antibodies are most suitably used. This type of mice is described by the reference by Tomizuka et al [Tomizuka. et al., Proc Natl Acad Sci USA., 97: 722-727, 2000].

The immunogen administration method when immunizing mice can be any of subcutaneous injection, intraperitoneal injection, intravenous injection, intradermal injection, intramuscular injection, foot pad injection, and the like. Intraperitoneal injection, foot pad injection or intravenous injection is preferred.

The immunization can be conducted once or repeated several times at a suitable interval. Afterwards, the antibody titer against the antigen in the serum of the immunized animal is measured. When animals with a sufficiently high antibody titer are used as a supply source for antibody producing cells, the efficiency of later operations is increased. In general, it is preferable to use antibody producing cells derived from animals 3-5 days after the final immunization for the following cell fusion.

Examples of the method used here for measuring antibody titer include known techniques such as radioimmunoassay (hereinafter referred to as "RIA method"), enzyme linked immunoabsorbent assay (hereinafter referred to as "ELISA method"), fluorescent antibody method, passive hemagglutination method, and the like. From the standpoint of detection sensitivity, rapidity, accuracy, and the possibility of automated operation, RIA method or ELISA method is suitable.

According to the ELISA method for example, the measurement of antibody titer of the present invention can be conducted by the following procedure. First, antigen against human antibody is absorbed onto the solid phase surface of an ELISA 96 well plate for example. Furthermore, the solid phase surface which has not absorbed antigen is covered with a protein unrelated to the antigen, such as bovine serum albumin (BSA). After rinsing the surface, it is allowed to contact with a serially diluted reagent as a primary antibody (for example, serum from transgenic mice having the ability to produce human antibodies) to make the antigen described above which binds to the anti-FGF23 antibody in the sample. Furthermore, an enzyme-labeled antibody against human antibody is added as the secondary antibody to be allowed to bind to the human antibody. After washing, a substrate for the enzyme is added. Then, change in the light absorption caused by the color resulted from the substrate breakdown is measured to calculate the antibody titer.

(3) Preparation Step for Myeloma

For the myeloma, cells which do not have antibody production ability by themselves and which are derived from mammals such as mouse, rat, guinea pig, hamster, rabbit, or humans, and the like can be used. In general, cell lines obtained from mice, for example 8-azaguanine resistant mice (BALB/c derived) myeloma line P3X63Ag8U.1 (P3-U1) [Yelton, D. E. et al., Current Topics in Microbiology and Immunology, 81: 1-7, 1978], P3/NSI/1-Ag4-1 (NS-1) [Kohler, G. et al., European J. Immunology, 6: 511-519, 1976], Sp2/O-Ag14 (SP2/O) [Shulman, M. et al., Nature, 276: 269-270, 1978], P3X63Ag8.653 (653) [Kearney, J. F. et al., J. Immunology, 123: 1548-1550, 1979], P3X63Ag8 (X63) [Horibata, K. and Harris, A. W., Nature, 256: 495-497, 1975] and the like are preferably used. These cell lines are subcultured in a suitable medium, for example 8-azaguanine medium [an RPMI-1640 medium supplemented which glutamine, 2-mercaptoethanol, gentamycin, and fetal calf serum (FCS) as well as 8-azaguanine], Iscove's Modified Dulbecco's Medium (IMDM), or Dulbecco's Modified Eagle Medium (DMEM). However, 3-4 days prior to cell fusion, the cell lines are subcututed in a normal medium (for example DMEM medium containing 10% FCS), and on the day of fusion, a cell number of 2×107 or greater is prepared.

(4) Cell Fusion

The antibody producing cells are plasma cells and lymphocytes which are their precursor cells. These can be obtained from any site from the individuals. In general, the spleen, lymph node, bone marrow, tonsils, peripheral blood, or any of these can be combined. In general, splenic cells are used most often.

After the final immunization, the site where the antibody producing cells is present, for example the spleen, is removed from mice which have achieved a prescribed antibody titer, and the splenic cells which are the antibody producing cells are prepared. Next, splenic cells and myeloma are fused. For the means for fusing the splenic cell and the myeloma obtained in step (3), the method that is used most generally is a method using polyethylene glycol. This method has relatively low cell toxicity and the fusion operation is also easy. This method has the following procedure, for example.

The splenic cell and myeloma is washed well with serum-free medium (for example DMEM) or a phosphate buffered saline (PBS). The splenic cell and myeloma are mixed at a cell number ratio of around 5:1-10:1 and are centrifuged. The supernatant is removed, and after loosening the precipitated cell group, 1 mL of a serum-free medium containing 50% polyethylene glycol (molecular weight 1000-4000) (w/v) is instilled into the cells while stirring. Afterwards, 10 mL of serum-free medium is slowly added, and afterwards, this is centrifuged. The supernatant is again discarded, and the precipitated cells is suspended in a suitable amount of normal medium (referred to as HAT medium) which contains suitable amount of hypoxanthine/aminopterine/thymidine (HAT) solution and human interleukin-6 (IL-6). The cells are aliquoted onto each well of a culturing plate (henceforth referred to as "plate"), and cultured for approximately 2 weeks at 37 degrees C. under 5% carbon dioxide gas. During this time, HAT medium is supplemented as needed.

(5) Selection of Hybridoma Group

When the myeloma cells described above is a 8-azaguanine resistant strain, in other words, if it is a hypoxanthine/guanine/phosphoribosyltransferase (HGPRT) deficient strain, the myeloma cells which were not fused and fused cells of only myeloma cells will not survive in HAT containing medium. On the other hand, fused cells of only antibody producing cells and hybridomas of antibody producing cell and myeloma cell can survive, but for the fused cells of only antibody producing cells have a limited lifespan. Therefore, by continuing to culture in a HAT-containing medium, only the hybridomas which are fused cells between antibody producing cells and myeloma cells will survive. As a result, hybridomas can be selected.

For the hybridoma which is growing in colonies, medium exchange to a medium in which aminopterin is removed from HAT medium (henceforth referred to as HT medium) is conducted. Afterwards, a portion of the medium supernatant is collected, and the anti-FGF23 antibody titer is measured by the ELISA method, for example.

Above, we showed an example of a method using an 8-azaguanine resistant cell line, but other cell lines can also be used according to the selection method for hybridomas. In these cases, the medium composition to be used also changes.

(6) Cloning Step

By measuring the antibody titer with the same method as the antibody titer measuring method as in (2), the hybridoma which has been determined to produce the specific antibody is transferred to another plate, and cloning is conducted. Examples of cloning methods include the limiting dilution method in which the hybridoma are diluted so that there is one hybridoma contained per 1 well of a plate and this is cultured; soft agar method in which the hybridomas are cultured in a soft agar medium and the colonies are collected; a method in which one cell at a time is removed with a micromanipulator and this is cultured; "sorter cloning" in which a single cell is separated by a cell sorter, and the like. The limiting dilution method is simple and is often used.

With regard to the wells in which antibody titer has been seen, for example, cloning is repeated 2-4 times by the limiting dilution method, and cells having a stable antibody titer, these are selected as anti-FGF23 monoclonal antibody producing hybridoma lines.

(7) Preparation of Monoclonal Antibody by Hybridoma Culturing

The hybridomas in which cloning has been completed are cultured by exchanging the medium from HT medium to normal medium. For large-scale culturing, there are rotation culturing using a large-scale culture bottle, spinner culturing, or culturing using a hollow fiber system, and the like. By purifying the supernatant in large-scale culturing using a method known to those skilled in the art such as gel filtration and the like, anti-FGF23 monoclonal antibody can be obtained. In addition, by growing this hybridoma intraperitoneally in the same strain of mouse (for example BALB/c) or nu/nu mouse, rat, guinea pig, hamster, or rabbit or the like, peritoneal fluid containing large amounts of anti-FGF23 monoclonal antibody can be obtained. A simple method for purification uses commercial monoclonal antibody purification kits (for example, MAbTrap GII kit; GE Healthcare Bioscience Co.) and the like.

The monoclonal antibodies obtained in this way have high antigen specificity against FGF23.

In addition, recombinant antibody can be prepared by cloning the gene which encodes human monoclonal antibody from the antibody producing cells of the hybridoma and the like, incorporating the gene into a suitable vector and introducing into a host (for example, mammalian cell line, *E. coli*, yeast cell, insect cell, plant cell, and the like), and using genetic recombination technology (Delves, P. J., ANTIBODY PRODUCTION ESSENTIAL TECHNIQUES., 1997 WILEY, Shepherd, P. and Dean C., Monoclonal Antibodies., 2000 OXFORD UNIVERSITY PRESS, Goding, J. W., Monoclonal Antibodies: principles and practice., 1993 ACADEMIC PRESS).

The present invention includes the nucleic acids which contain the genetic sequence for the antibody of the hybridoma which produces the antibody of the present invention, in particular the nucleic acid for the heavy chain variable region and light chain variable region of the antibody produced by the hybridoma of the present invention that will be described later. Here, nucleic acid includes DNA and RNA. Furthermore, the present invention includes the nucleic acid of the mature portion in which the region encoding the signal sequence from the nucleic acid of the heavy chain variable region and light chain variable region of the present invention has been removed. Furthermore, in addition to the nucleic acids described above, the nucleic acid of the present invention includes the nucleic acids having the codons corresponding to the amino acids of the amino acid sequence of the antibody of the present invention and to the amino acids of the antibody heavy chain variable region and/or light chain variable region of this antibody.

In order to prepare the gene which encodes the monoclonal antibody from the hybridoma, a method is used in which DNA encoding each of the L chain V region, L chain C region, H chain V region and H chain C region of the monoclonal antibody is prepared by PCR method or the like. For this, oligoDNA designed from the anti-FGF23 antibody gene or the amino acid sequence is used as the primer. For the template, DNA prepared from the hybridoma can be used. These DNAs are incorporated into one suitable vector and this is introduced into a host and is expressed, or else these DNAs are each incorporated into a suitable vector, and co-expressed.

For the vector, phages or plasmids which can grow autonomously in the host microorganisms are used. For the plasmid DNA, examples include plasmids from *E. coli*, *Bacillus subtilis*, or yeast, and the like. For the phage DNA, examples include λ phage.

The host used in transformation is not limited as long as it is one which can express the target gene. Examples include bacteria (*E. coli*, *Bacillus subtilis*, and the like), yeast, animal cells (COS cells, CHO cells and the like), and insect cells and the like.

Methods for introducing genes into a host are known, and there are many examples of methods (for example, a method which uses calcium ion, electroporation method, spheroplast method, lithium acetate method, calcium phosphate method, lipofection method, and the like). In addition, examples of methods for introducing the gene into animals which will be described later include microinjection method, method of introducing genes into ES cells using electroporation method and lipofection method, nuclear transplantation, and the like.

In the present invention, the transformant is cultured, and the anti-FGF23 antibody is obtained by collecting from the culture product. Here, "culture product" signifies any of (a) culture supernatant, (b) cultured cells or cultured bacteria or their homogenate, (c) secretions of the transformant. In order to culture the transformant, a medium suitable for the host is used, and stationary culture method, culture method by roller bottle and the like are used.

After culturing, when the target antibody is produced inside the bacteria or inside the cell, the antibody is collected by homogenizing the bacteria or cell. In addition, when the target antibody is produced outside the bacteria or outside the cell, the culture solution can be used directly, alternatively the bacteria or cells are removed by centrifugation or the like. Afterwards, the target antibody can be isolated and purified from the culture product by general biochemical methods using, singly or in combination, various chromatographies used for isolation and purification of proteins.

Furthermore, using transgenic animal creation techniques, animal hosts in which the gene of the target antibody is incorporated into endogenous genes, for example transgenic cattle, transgenic goat, transgenic sheep, or transgenic pig are created. A large amount of monoclonal antibody derived from the antibody gene can be obtained from the milk secreted from these transgenic animals (Wright, G., et al., Bio/Technology 9: 830-834, 1991). When culturing the hybridoma in vitro, the hybridoma is grown, maintained and stored according to the various conditions of the properties of the cultured cell the experimental research and culture methods and the like. Known nutrition medium or various nutrition medium derived and prepared from known basic medium can be used to produce the monoclonal antibody in the culture supernatant.

(8) Assay of the Monoclonal Antibody

Determining the isotype and subclass of the monoclonal antibody obtained in this manner can be conducted in the following manner. First, examples of the identification method include Ouchterlony method, ELISA method, or RIA method, and the like. The Ouchterlony method is simple, but when the concentration of the monoclonal antibody is low, a concentrating procedure is necessary. On the other hand, when ELISA method or RIA method is used, the culture supernatant is reacted directly with the antigen absorbed solid phase, and as a secondary antibody, antibodies responding to various immunoglobulin isotypes, and subclasses can be used to identify the isotype and subclass for the monoclonal antibody.

Furthermore, the quantification of the protein can be conducted by Folin/Lowry method and by a method which calculates light absorption at 280 nm [1.4 (OD280)=immunoglobulin 1 mg/mL].

Identification of recognition epitopes of the monoclonal antibody (epitope mapping) is conducted as follows. First, the partial structures of various molecules that monoclonal antibodies recognize are created. For the creation of partial structures, there is a method in which known oligopeptide synthesis techniques are used to create various partial peptides of the molecule, and a method in which, using genetic recombination techniques, the DNA sequence which encodes the target partial peptide is incorporated in a suitable expression plasmid, and the peptides are produced inside or outside of the host such as $E.\ coli$ or the like. However, in general, both methods are combined for the above objective. For example, a series of polypeptides in which the antigen protein has been sequentially shortened at random lengths from the carboxy terminal or amino terminal is created using genetic recombination techniques known to those skilled in the art. Afterwards, the reactivity of the monoclonal antibody to these polypeptides is studied, and recognition sites are roughly determined.

Afterwards, for further detail, the oligopeptide of the corresponding portion, or variants and the like of these peptides are synthesized by oligopeptide synthesis techniques known to those skilled in the art. In order to define the epitopes, the binding of the monoclonal antibodies contained as an active ingredient in the agent for prevention or treatment of the present invention to these peptides is studied, alternatively the competitive inhibition activity of the peptides to the binding of the monoclonal antibodies to the antigen is studied. As a simple method for obtaining various oligopeptides, commercial kits (for example, SPOTs kit (Genosis Biotechnologies), a series of multipin peptide synthesis kits which uses multipin synthesis method (Chiron Co,) and the like) can be used.

(9) Producing the Antibody Fragment

The antibody fragment is produced by genetic engineering methods or proteochemical methods based on the antibody described in (7) of the above.

For the genetic engineering method, the gene which encodes the target antibody fragment is constructed and expressed using a suitable host such as animal cell, plant cell, insect cell, $E.\ coli$ and the like, and the antibody fragment is purified.

For the proteochemical method, proteases such as pepsin, papain, and the like are used for site specific cleavage, and purification is conducted.

For the antibody fragment, examples include peptides comprising Fab, F (ab')2, Fab', scFv, diabody, dsFv, CDR and the like. The production method for each of the antibody fragments is described in detail below.

(i) Production of Fab

Proteochemically, Fab can be created by treating IgG with protease papain. After treatment with papain, if the original antibody is an IgG subclass having protein A binding ability, by passing through a protein A column, IgG molecules and Fc fragments are separated, and a uniform Fab can be recovered (Monoclonal Antibodies: Principles and Practice, third edition, 1995). If the antibody is an IgG subclass with no protein A binding ability, with ion exchange chromatography, Fab is recovered from the fraction which is eluted at low salt concentrations (Monoclonal Antibodies: Principles and Practice, third edition, 1995). In addition, for genetic engineering of Fab, $E.\ coli$ is used in most cases, or insect cells and animal cells and the like are used to produce Fab. For example, DNA which encodes the V region of the antibody described in 2 (7) above is cloned into a Fab expression vector to construct a Fab expression vector. For the Fab expression vector, anything can be used as long as DNA for Fab can be incorporated and expressed. An example is pIT106 (Science, 240: 1041-1043, 1988) and the like. The Fab expression vector is introduced into a suitable $E.\ coli$, and Fab can be generated and stored in an inclusion body or periplasma layer. From the inclusion body, the Fab can be activated by a refolding method normally used with proteins. In addition, when expression is in the periplasma layer, active Fab is discharged into the culture supernatant. After refolding or from the culture supernatant, by using a column with bound antigen, a uniform Fab can be purified (Antibody Engineering, A Practical Guide, W. H. Freeman and Company, 1992).

(ii) Production of F (ab')2

Proteochemically, F (ab')2 is produced by treating IgG with protease pepsin. After treating with pepsin, a uniform F (ab')2 is recovered through the same purification operation as with Fab (Monoclonal Antibodies: Principles and Practice, third edition, Academic Press, 1995). In addition, it can be created by a method in which Fab' described in the following (iii) is treated with a maleimide such as o-PDM or bis maleimide hexane and the like, and thioether bonds are formed or it can be created by a method in which it is treated with DTNB [5,5'-dithiobis(2-nitrobenzoic acid)], and S—S bonds are formed (Antibody Engineering, A Practical Approach, IRL PRESS, 1996).

(iii) Production of Fab'

Fab' can be obtained by treating F (ab')2 described in the above (ii) with a reducing agent such as dithiothreitol, and the like. In addition, with genetic engineering, Fab' can be created by using $E.\ coli$ in most cases or insect cells or animal cells and the like. For example, DNA which encodes the V region of the antibody described in the above 2 (7) is cloned into a Fab' expression vector and a Fab' expression vector can be constructed. For the Fab' expression vector, anything can be used as long as DNA for Fab' can be incorporated and expressed. An example is pAK19 (BIO/TECHNOLOGY, 10: 163-167, 1992) and the like. Fab' expression vector is introduced into a suitable *E. coli*. Fab' can be generated and accumulated in an inclusion body or in the periplasma layer. From the inclusion body, Fab' is activated by the refolding method used normally in proteins. In addition, when expressed in the periplasma layer, bacteria is homogenized by treatment with partial digestion by lisozyme, osmotic shock, sonication, and the like, and this can be recovered from outside the bacteria. After refolding or from the bacterial homogenate, a uniform Fab' can be purified by using a protein G column and the like (Antibody Engineering, A Practical Approach, IRL PRESS, 1996).

(iv) Production of scFv

By genetic engineering, scFv can be produced by using a phage or *E. coli* or insect cells or animal cells and the like. For example, DNA which encodes the V region of the antibody described in 2 (7) can be cloned into a scFv expression vector to construct a scFv expression vector. For the scFv expression vector, anything can be used as long as DNA for scFv can be incorporated and expressed. Examples include pCANTAB5E (GE Healthcare Bioscience Co.), pHFA (Human Antibodies & Hybridomas, 5: 48-56, 1994) and the like. scFv expression vector is introduced into a suitable *E. coli*. By infecting with a helper phage, a phage in which scFv is expressed on the phage surface as fused with a phage surface protein can be obtained. In addition, scFv can be generated and accumulated in the inclusion body or in the periplasma layer of the *E. coli* in which the scFv expression vector has been introduced. From the inclusion body, activated scFv can be obtained by the refolding method normally used for proteins. In addition, when expressed in the periplasma layer, bacteria are homogenized by treatment with partial digestion by lisozyme, osmotic shock, sonication, and the like, and this is recovered from outside the bacteria. After refolding or from the bacterial homogenate, a uniform scFv can be purified by using positive ion exchange chromatography and the like (Antibody Engineering, A Practical Approach, IRL PRESS, 1996).

(v) Production of Diabody

By genetic engineering, diabody can be produced mainly using *E. coli* as well as insect cells and animal cells. For example, DNA is produced in which VH and VL of the antibody described in above 2 (7) are linked so that the amino acid residues encoded by the linker are 8 residues or less and cloned in a diabody expression vector to construct the expression vector for diabody. Any vector can be used as a diabody expression vector as long as it can be integrated with diabody DNA and express diabody DNA. Examples include pCANTAB5E (GE Healthcare Bioscience), pHFA (Human Antibodies Hybridomas, 5, 48, 1994) and the like, diabody can be generated and accumulated in the inclusion body or in the periplasma layer of the *E. coli* in which the diabody expression vector has been introduced. From the inclusion body, activated diabody can be obtained by the refolding method normally used for proteins. In addition, when expressed in the periplasma layer, bacteria are homogenized by treatment with partial digestion by lisozyme, osmotic shock, sonication, and the like, and this is recovered from outside the bacteria. After refolding or from the bacterial homogenate, a uniform diabody can be purified by using positive ion exchange chromatography and the like (Antibody Engineering, A Practical Approach, IRL PRESS, 1996).

(vi) Production of dsFv dsFv can be created mainly using *E. coli* as well as insect cells and animal cells by genetic engineering. First, mutations are introduced at appropriate sites of DNA which encodes VH and VL of antibody described in (ii), (iv) and (v), and DNA in which the coded amino acid residues are replaced with cysteine is produced. Each DNA produced can be cloned in dsFv expression vector to construct expression vectors for VH and VL. Any vector can be used as an dsFv expression vector as long as it can be integrated with and express dsFv DNA. For example, pUL19 (Protein Engineering, 7: 697-704, 1994) and the like can be used. The expression vector for VH and VL can be introduced into an appropriate *E. coli* and generated products can be accumulated in inclusion body or periplasma layer. VH and VL are obtained from inclusion body and periplasma layer, mixed and converted to dsFv with activity by the refolding method which is employed in normal protein processing. After refolding, further purification by ion-exchange chromatography and gel-filtration can be carried out (Protein Engineering, 7: 697-704, 1994).

(vii) Production of CDR Peptide

Peptides containing CDR can be produced by the chemical synthesis method such as Fmoc method or tBoc method and the like. Also, CDR peptide expression vector can be produced by producing DNA which encodes a peptide containing CDR and by cloning the DNA produced in an appropriate expression vector. Any vector can be used as an expression vector as long as it can be integrated with and express DNA that encodes CDR peptide. For example, pLEX (Invitrogen) and pAX4a+ (Invitrogen) may be used. The expression vector can be introduced into an appropriate *E. coli* and generated products can be accumulated in inclusion body or periplasma layer. CDR peptide is obtained from inclusion body or periplasma layer and can be purified by ion exchange chromatography and gel-filtration (Protein Engineering, 7: 697-704, 1994).

3. Characteristic of the Antibody of the Present Invention and the Functional Fragment Thereof The antibody of the present invention and the functional fragment thereof possesses any of the characteristic below.

(a) FGF23 binding test; binds to the full length protein having amino acid residues from 25th to 251st of SEQ ID NO: 4 of FGF protein.

(b) In vitro test; inhibits the action of FGF23 in an assay, by which the action of FGF23 can be detected. An example of the method for detecting the action of FGF23 in vitro is the activation of the promoter of the early growth response gene-1 by human FGF23 stimulation (Nature, 444: 770-774, 2006).

(c) In vivo test; inhibits the activity of endogenous FGF23 and increases serum phosphorous concentration and serum 1,25D concentration when administered to human. The extent of the increase of the serum phosphorous concentration and serum 1,25D concentration is greater compared to conventional antibody, 2C3B antibody (the mouse monoclonal antibody against FGF23 protein disclosed in WO03/057733, anti-FGF23 antibody produced by hybridoma of Accession No. FERM BP-7838) and also the duration of increased level of serum phosphorous concentration and serum 1,25D concentration is long. For example, the duration of elevated serum phosphorous concentration is about 3 times or longer, preferably about 5 times as that of 2C3B antibody, and the duration of elevated serum 1,25D concentration is about 1.5 times or longer, preferably about 2.5 times as that of 2C3B antibody when administered to cynomolgus monkey.

The present invention also includes a nucleic acid which encodes an amino acid sequence of the antibody to FGF23 of the present invention. The nucleic acid may be DNA or RNA. The nucleic acid of the present invention is, preferably, a nucleic acid which encodes an amino acid sequence of antibody produced by hybridoma C10. An example is a nucleic acid encoding the amino acid sequence of the heavy chain variable region (heavy chain nucleotide sequence of C10 antibody), which is coded by the nucleotide sequence from at position 58 C to at position 408 A shown in SEQ ID NO: 11. In addition, another example is a nucleic acid encoding the amino acid sequence of the light chain variable region, which is coded by the nucleotide sequence from G at position 67 to A at position 384 shown in SEQ ID NO: 13.

II. Pharmaceutical Compositions

A formulation which is a pharmaceutical composition comprising the human anti-FGF23 antibody of the present invention or the functional fragment thereof is included in the scope of the present invention. Such a formulation, preferably, includes in addition to the antibody and the functional fragment thereof, a physiologically acceptable diluents or carriers and may be a mixture with other drugs such as other antibody or antibiotics. Appropriate carriers include physiological saline, phosphate buffered saline, phosphate buffered saline glucose solution, and buffered physiological saline, but not limited to these. Further, the antibody may be freeze-dried and may be re-constituted by adding above buffer solution when needed, and then used. Administration routes include oral administration, or parenteral administration such as intraoral, tracheobronchial, endorectal, subcutaneous, intramuscular and intravenous administration, and preferred administration route is intravenous administration. Administration can be conducted in various formulations and the formulations include, aerosol, capsules, tablets, granules, syrup, emulsion, suppositories, injections, ointments and tapes.

Liquid preparations such as emulsion and syrup can be produced using additives for example: water; saccharides such as sucrose, sorbitol and fructose; glycols such as polyethylene glycol, propylene glycol; oils such as sesame oil, olive oil and soy bean oil; preservatives such as p-hydroxybenzoate esters; flavors such as strawberry flavor and peppermint.

Capsules, tablets, powder and granules can be produced using additives for example: excipients such as lactose, glucose, sucrose and mannitol; disintegrators such as starch and sodium alginate; lubricants such as magnesium stearate and talc; binders such as polyvinyl alcohol, hydroxypropyl cellulose and gelatin; surface active agents such as fatty acid ester; plasticizers such as glycerin.

In the injections, additives can be used include; water; saccharides such as sucrose, sorbitol, xylose, trehalose, fructose and the like; sugar alcohols such as mannitol, xylitol and sorbitol; buffers such as phosphate buffer, citrate buffer and glutamate buffer; surface active agents such as fatty acid ester.

An appropriate formulation for parenteral administration includes injections, suppositories, aerosol and the like. In case of injections, it is normally provided in the form of unit dosage ampules or multiple dosage containers. It may be powder which is re-dissolved, when in use, in an appropriate carrier, for example pyrogen-free sterile water. These formulations contain additives such as emulsifier, suspending agent and the like, which are generally used for formulating in these compositions. Methods for injection include, for example intravenous infusion, intravenous injection, intramuscular injection, intraperitoneal injection, subcutaneous injection, intradermal injection and the like. Also, the dosage is different according to the age of the administration subject, administration route, frequency of administration, and can be changed widely.

A suppository is prepared using a carrier such as cacao butter, hydrogenated fat or carboxylic acid. Aerosol can be prepared using the antibody of the present invention of the functional fragment thereof itself, or using a carrier which does not irritate oral and respiratory tract mucosa of a recipient (patient) and can disperse the aforementioned antibody and the functional fragment thereof as fine particles to facilitate absorption.

In particular, examples of a carrier include lactose, glycerin and the like. Depending on the characteristic of the aforementioned antibody or the functional fragment thereof and the characteristic of the carrier to be used, formulation such as aerosol, dry powder and the like can be chosen. Also, the components shown as examples of additives for oral formulation can be added to these parenteral formulations.

The dosage may vary according to symptoms, age, body weight but normally in oral administration, about 0.01 mg-1000 mg per day for an adult is administered. This can be administered once or divided into several batches. In parenteral administration, about 0.01 mg -1000 mg can be administered by subcutaneous, intramuscular or intravenous injection per administration.

The present invention includes the antibody of the present invention, or the functional fragment thereof, or a preventive or therapeutic method for diseases described below using a pharmaceutical composition containing thereof, and furthermore, the present invention include a use of the antibody of the present invention or the functional fragment thereof for manufacturing an agent for preventive or therapeutic of the diseases described below.

Diseases that can be prevented or treated by the antibody of the present invention or the functional fragment thereof include diseases having excessive activity of FGF23 such as tumor-induced osteomalachia, ADHR, XLH, fibrous dysplasia, McCune-Albright syndrome, and a disease accompanying abnormal mineral metabolism such as autosomal recessive hypophosphataemia. Further, improving effects can be expected for syndromes associated with these diseases such as, hypophosphataemia, bone mineralization failure, bone pain, muscle weakness, skeletal deformity, growth disorder, low blood 1,25D and the like. Since FGF23 plays an important role under the physiological condition, the calcium metabolism control activity of FGF23, which is mediated by the control of phosphorous metabolism and vitamin D metabolism, can be regulated by the antibody of the present invention and the functional fragment thereof, and thus, they can be used preventively and therapeutically for diseases caused by abnormality in mineral metabolism and vitamin D metabolism, such as osteoporosis, rickets (including hypophosphatemic rickets and vitamin D-resistant rickets), hypercalcaemia, hypocalcaemia, ectopic calcification, osteosclerosis, Paget's disease, hyperparathyroidism, hypoparathyroidism, pruritus and the like. Further, the antibody of the present invention and the functional fragment thereof can also be used preventively or therapeutically for diseases caused by the complication of kidney failure and dialysis for kidney failure, represented by renal osteodystrophy, dialysis osteopathy, renal tubular dysfunction. On the other hand, 1,25D has been reported to have activities not only on mineral metabolism such as calcium metabolism as described above but also cell growth inhibitory effect, cell differentiation promotion activity and the like. Thus the antibody of the present invention and the functional fragment thereof can be used therapeutically and preventively against diseases caused by the cells whose growth and differentiation are regulated by 1,25D.

Also, it is known that, in tumor-induced osteomalachia, overproduction of FGF23 by the tumor causes pathology. Therefore it may be conceivable that retraction of the tumor may be induced by using the antibody of the present invention linked with a radioactive substance such as radioactive isotope and the like, or with therapeutic reagent of various toxins such as low molecular weight drugs and by accumulating the present antibody in the FGF23 overproducing tumor.

III. Formulation Example

The formulation containing the antibody of the present invention or the functional fragment thereof, is provided as an ampule of sterile solution dissolved in water or pharmacologically acceptable solution or suspension. Also, a sterile powder formulation (it is preferable to freeze dry the molecule of the present invention) may be placed in an ampule and may be diluted in use with a pharmacologically acceptable solution.

EXAMPLES

Following is the detailed description of the present invention by Examples, but it does not mean that the present invention is limited to these descriptions of Examples only.

Example 1

Preparation of an Expression Vector for Recombinant Human FGF23

(1) Construction of an Expression Vector for Human FGF23H Protein cDNA encoding human FGF23 was amplified by using the human cDNA library of the responsible tumor for tumor-induced osteomalachia as a template, a F1EcoRI primer (SEQ ID NO: 1) and a LHisNot primer (SEQ ID NO: 2) and LA-Taq DNA polymerase and by conducting 35 cycles of a PCR step consisting of heating at 96° C. for 1 min, then at 96° C. for 30 sec, at 55° C. for 30 sec and at 72° C. for 30 sec. The F1EcoRI primer was annealed to a sequence present at further upstream of the 5' side of the nucleotide sequence encoding human FGF23 and adds an EcoRI restriction site at the 5' side of the nucleotide sequence encoding human FGF23 in the amplified fragment. The LHisNot primer comprises a sequence which anneals to the sequence at the 5' side of the stop codon of the nucleotide sequence encoding human FGF23, a sequence encoding the terminal codon which follows the sequence encoding the His6-tag sequence (His-His-His-His-His-His) and a NotI restriction site. As a result, the amplified fragment encodes human FGF 23 protein in which the His6-tag sequence is added at the carboxy terminal and has a NotI restriction site at the downstream thereof. This amplified fragment was digested with EcoRI and Not I, and ligated to an animal cell expression vector, pcDNA3.IZeo (Invitrogen) which was similarly digested with EcoRI and NotI. The expression vector constructed in such a way was cloned and the nucleotide sequence was determined to confirm that the expression vector encodes the target, human FGF23 protein to which the His6-tag sequence was added. This vector is called pcDNA/hFGF23H.

F1EcoRI:

(SEQ ID NO: 1)
CCGGAATTCAGCCACTCAGAGCAGGGCACG

LHisNot:

(SEQ ID NO: 2)
ATAAGAATGCGGCCGCTCAATGGTGATGGTGATGATGGATGAACTTGGC
GAA (2) Construction of an Expression Vector for Human FGF23 Protein A fragment was amplified by using pcDNA/hFGF23H as a template, the F1EcoRI primer and a LNot primer (SEQ ID NO: 3) and LA-Taq DNA polymerase and by conducting 25 cycles of a PCR step consisting of heating at 94° C. for 1 min, then at 94° C. for 30 sec, at 55° C. for 30 sec and at 72° C. for 1 min. After terminating the reaction, the fragment encoding human FGF23 was digested with EcoRI and NotI, and then purified. This was cloned by inserting at the EcoRI and NotI restriction sites of pEAK8/IRES/EGFP vector, an animal cell expression vector, pEAKS (Edge Biosystem), to which the intramolecular ribosomal entry sequence (IRES) and enhanced green fluorescent protein (EGFP) were ligated. The nucleotide sequence of thus obtained plasmid was determined to confirm that it encodes human FGF23 protein. This vector was called pEAK8/IRES/EGFP/hFGF23.

LNot:

(SEQ ID NO: 3)
ATAAGAATGCGGCCGCTCAGATGAACTTGGCGAA

Example 2

Expression of Recombinant Human FGF23 and Recombinant Mutant Human FGF23H Protein (1) pcDNA/hFGF23H was Linearized By Cleaving the FspI Restriction Site pcDNA/hFGF23H was linearized by cleaving the FspI restriction site in the ampicillin resistant gene in the vector and purified, and then mixed with CHO Ras clone-1 cells (Shirahata, S., et al., Biosci Biotech Biochem, 59: 345-347, 1995) and transfected to the cells by electroporation using Gene Pulser II (Bio Rad). After culturing these cells in MEM a medium (Gibco BRL) containing 10% FCS for 24 h, Zeocin (Invitrogen) was added to a final concentration of 0.5 mg/ml and then the cells were cultured for a week. Cells attached and grown were released by trypsinization and cloned by the limited dilution method in the presence of Zeocin at the final concentration of 0.3 mg/ml to obtain a multiplicity of cloned cells. The cell expressing human FGF23H most efficiently was identified by the Western blotting method. Culture supernatants of each cloned cell were collected and were subjected to SDS-polyacrylamide gel electrophoresis, and then proteins were transferred to a PVDF membrane (Millipore). A signal derived from FGF-23H protein was detected at about 32 kDa by using anti-His-tag (carboxy terminal) antibody (Invitrogen) and ECL photo-luminescent system (GE Healthcare Bioscience). As the result, the highest expression was found in a clone called #20, which was named as CHO-OST311H and deposited at International Patent Organism Depositary (IPOD) National Institute of Advanced Industrial Science and Technology (AIST) Tsukuba Central 6, 1-1-1 Higashi, Tsukuba, Ibaraki, Japan on Aug. 11, 2000 (Deposition No.: FERM BP-7273). In the present description, CHO-OST311H is called CHO-hFGF23H.

(2) Obtaining of Human FGF23 Expressing Cells

Transfection of pEAK8/IRES/EGFP/hFGF23 vector to CHO Ras clone-1 cells was carried out by the gene transfection method using a membrane fusion lipid. CHO Ras clone-1 cells were cultured in 6 well plates until about 60% of the bottom of the well was covered by the cells, and then the culture medium was removed and 1 ml of MEMα medium without serum was added. Each of 2.5 µg of the vector to be introduced and 10 µl of Transfectam (Registered Trademark) (Promega) was mixed with 50 µl of MEMα medium without serum, and then both solutions were mixed and left standing for 10 min. The mixtures were added to wells of 6 well plates prepared beforehand. After incubating for 2 hours, the culture medium containing DNA was removed, replaced with a medium containing 10% FCS, and the culture was incubated overnight. Next day, Puromycin (Sigma) was added to a final concentration of 5 µg/ml to select drug resistant cells. The drug resistant cells thus obtained were cloned by the limited dilution method. Further, the cell line expressing the target protein most efficiently was obtained by Western blotting method. This cell line was called CHO-hFGF23.

(3) Expression and Detection of Recombinant Human FGF23 Protein in Animal Cells

Western blotting of the recombinant in the culture supernatant of CHO-hFGF23H using the antibodies against the carboxy terminal anti-His6 tag sequence detected bands of about 32 kDa and about 10 kDa. These 2 bands were excised out of the gel, and the amino acid sequences of the amino terminals were determined. In the larger molecular weight band (about 32 kDa), the sequence from amino acid 25 of SEQ ID NO: 4 was detected and it appeared to be human FGF23 protein from which the signal sequence was removed during the process of excretion. On the other hand, in the band having a smaller molecular weight, the sequence from amino acid 180 of SEQ ID NO: 4 was confirmed and it turned out that this fragment was the carboxy terminal fragment produced by the cleavage between amino acid 179 and 180. Also, the presence of a polypeptide having the sequence from amino acid 179 to the amino terminal (amino terminal fragment) was recognized by detecting it using polyclonal antibody which recognizes the amino terminal side of human FGF23 (International Publication No. WO02/14504 Pamphlet).

Similarly, in the culture supernatant of CHO-hFGF23 having no His6-tag sequence, the cleavage between amino acid residue 179 and 180 was confirmed (International Publication No. WO02/14504 Pamphlet). Therefore, following operations were carried out to separate and purify the full length human FGF23 protein, which appears not to be cut, having the sequence from amino acid 25 to amino acid 251 of SEQ ID NO: 4 (sometimes referred to as full length FGF23) from the amino terminal or carboxy terminal fragments.

(4) Purification of recombinant full length human FGF23 protein

The culture supernatant of CHO-hFGF23 was filtered through SuperCap (Registered Trade Mark) (Pall Gelman Laboratory) which is a membrane filter having 0.2 µm pore size, and the filtrate was passed through SP-Sepharose FF (GE Healthcare Bioscience). Substances having weak affinity to the column was washed and eluted with 50 mM sodium phosphate buffer, pH 6.7. This fraction contained the carboxy terminal fragment generated by the cleavage between amino acid 179 and 180. Protein held by the column was eluted with NaCl concentration gradient from 0 to 0.7 M, and full length human FGF23 protein was observed in the fraction eluted with about 0.3 M NaCl. Next, full length human FGF23 protein was absorbed to Talon Superflow (Registered Trade Mark) (Clonetech), which is a metal affinity column, washed with 50 mM sodium phosphate buffer, pH 6.7 and then eluted by adding imidazole at different concentrations. The fraction containing the target protein was absorbed to a SP sepharose FF column and eluted for further purification.

```
Human FGF23 amino acid sequence
                                      (SEQ ID NO: 4)
MLGARLRLWV CALCSVCSMS VLRAYPNASP LLGSSWGGLI

HLYTATARNS YHLQIHKNGH VDGAPHQTIY SALMIRSEDA

GFVVITGVMS RRYLCMDFRG NIFGSHYFDP ENCRFQHQTL

ENGYDVYHSP QYHFLVSLGR AKRAFLPGMN PPPYSQFLSR

RNEIPLIHFN TPIPRRHTRS AEDDSERDPL NVLKPRARMT

PAPASCSQEL PSAEDNSPMA SDPLGVVRGG RVNTHAGGTG

PEGCRPFAKF I
```

Example 3

Production of Mice Producing Human Antibody (KM Mice)

Mice producing complete human antibody for preparation of human monoclonal antibody have the homozygous genetic background for destructed endogenous both Ig heavy chain and kappa-light chain and also for having the chromosome 14 fragment (SC20) containing the human Ig heavy chain gene loci and the human Ig kappa chain trans gene (KCo5) at the same time. These mice were produced by cross-breeding the strain A mouse which has the human Ig heavy chain gene loci and the strain B mouse which has the human Ig kappa chain trans gene. The strain A is homozygous for destructed endogenous both Ig heavy chain and the kappa light chain, and is a mouse line having the chromosome 14 fragment (SC20) which can be transmitted to offsprings. This line of mouse is described, for example, in the report by Tomizuka et al., (Tomizuka, et al., Proc Natl. Acad. Sci. USA., 97: 722-727, 2000). Also, the strain B is homozygous for destructed endogenous both Ig heavy chain and the kappa light chain and is a transgenic mouse line having the human Ig kappa chain trans gene (KCo5). This line of mouse is described, for example, in the report by Fishwild et al., (Nat. Biotechnol., 14; 845-851, 1996).

In the following experiments, used are individual mice, which are obtained by crossing a male strain A mouse and a female strain B mouse, or a male strain B mouse and a female strain A mouse, and in which human Ig heavy chain and kappa light chain are detected at the same time in the serum [Ishida & Lonberg, IBC's 11th Antibody Engineering, Abstract 2000]. Furthermore, the mice producing human antibody can be obtained from Kirin Beer Company by contracting.

Example 4

Preparation of Human Monoclonal Antibody Against Human FGF23

(1) Obtaining a Hybridoma Producing Human Monoclonal Antibody Against Human FGF23

Monoclonal antibodies used in the present Examples are prepared according to the general method described in, such as, "Introduction to monoclonal antibody experimental manipulation" by Tamio Ando et al., Published by Kodansha, 1991. Full length human FGF23 protein prepared in Example 2 was used as an immunogen, and the human antibody producing mice produced in Example 3 which produce human immunoglobulin were immunized.

First, to prepare human monoclonal antibody against FGF23, purified full length human FGF23 protein prepared in Example 2 was mixed with RIBI adjuvant (Corixa) and inoculated intraperitoneally to human antibody producing mice at a dose of 20 μg/mouse as the first immunization. Similar to the first immunization, the mixture of purified FGF23 and RIBI adjuvant was inoculated total 3 times at 2 weeks intervals. Five mice were used for immunization, blood samples were collected after the third immunization, and the presence of human IgG antibody against FGF23 in sera was confirmed by the enzyme labeled immunosorbent assay (ELISA) method as described below. The mouse was selected which showed the highest serum value by the ELISA using FGF23 fixed on the solid phase with anti-FGF23 protein mouse monoclonal antibody, 3CIE, which was disclosed in International Publication No. WO03/057733 Pamphlet (anti FGF23 antibody produced by the hybridoma deposited as FERM BP-7839) and was immunized by 20 μg of full length human FGF23 protein/mouse via tail vein administration 3 days before taking the spleen out as described below.

The spleen was surgically taken out of the immunized mice, immersed in 10 ml of the DMEM containing 350 mg/mL of sodium bicarbonate, 50 units/mL of penicillin, 50 μg/mL streptomycin and no serum (Invitrogen, called DMEM without serum, hereinafter) and crushed on a mesh (Cell strainer: Falcon)) using a spatula. The cell suspension which passed through the mesh was centrifuged to precipitate cells, and then the cells were washed twice with DMEM without serum and suspended in DMEM without serum to measure the cell number. While, myeloma cells, SP2/0 (ATCC No. CRL-1581) were cultured in DMEM (Invitrogen) containing 10% FCS (Sigma) (called DMEM with serum, hereinafter) at 37° C. under 5% carbon dioxide gas so that cell density does not exceed 1×106 cells/mL. These myeloma cells were similarly washed with DMEM without serum, suspended in the same medium and counted. Recovered spleen cell suspension and mouse myeloma cell suspension were mixed at the cell number ratio 5:1, centrifuged and the supernatant was completely removed. To this cell pellet, 1 mL of 50% (w/v) polyethylene glycol 1500 (Boehringer-Manheim) as a fusion agent was added slowly while stirring the pellet with a tip of a pipette, and then 1 mL of DMEM without serum that was pre-warmed at 37° C. was added slowly in 2 portions and further 7 mL of DMEM without serum was added. After centrifuging, the supernatant was removed and the fused cells thus obtained were subjected to screening by the limited dilution method as described below. The hybridoma selection was carried out by culturing in DMEM containing 10% FCS and IL-6 (10 ng/mL)(or 10% hybridoma cloning factor (called HCF, hereinafter): Biobase), and hypoxanthine (H), aminopterin (A) and thymidine (T) (called HAT, hereinafter: Sigma). Further, single clones were obtained by the limited dilution method using DMEM containing HT (Sigma), 10% FCS and 10% HCF. Culturing was conducted in 96 well microtiter plates (Becton, Dickinson). Selection of hybridoma clones producing anti-FGF23 human monoclonal antibody (screening) and characterization of human monoclonal antibody produced by respective hybridomas were conducted by the enzyme labeled immunosorbent assay (ELISA) as described below. As the results, many hybridomas were obtained which contained human immunoglobulin γ chain (hIgγ) and human immunoglobulin light chain κ, and produced human monoclonal antibody having the specific reactivity to human FGF23. Among a number of hybridomas obtained, 2 clones (C10 and C15) were particularly obtained as hybridomas producing an antibody which recognizes the FGF23 protein. Furthermore, in all the Examples described below including this Example, the hybridoma clones that produce the anti-FGF23 human monoclonal antibody of the present invention were designated using symbols. Still further, "antibody" affixed before or after these symbols indicates the antibody produced by the hybridoma or recombinant antibody produced by host cells carrying the antibody gene (full length or variable region) isolated from the hybridoma. Also, to the extent where the context clearly indicates, the name of the hybridoma clone may indicate the name of the antibody. The hybridoma clone C10 has been deposited at International Patent Organism Depositary (IPOD) National Institute of Advanced Industrial Science and Technology (AIST) Tsukuba Central 6, 1-1-1 Higashi, Tsukuba, Ibaraki, Japan on Feb. 2, 2007 (Deposition No.: FERM ABP-10772) (Label for ID: C10).

(2) Purification of C10 and C15 Antibody from the Culture Supernatant of the Hybridoma C10 and C15 hybridoma obtained in Example 4 was conditioned to eRDF medium (Kyokuto Seiyaku) containing bovine insulin (5 μg/ml, Invitrogen), human transferrin (5 μg/ml, Invitrogen), ethanoamine (0.01 mM, Sigma), sodium selenite (2.5×10-5 mM, Sigma), 1% Low IgG Fetal Bovine Serum (Hyclone). The hybridoma was cultured in a flask and the culture supernatant was recovered. The culture supernatant was affinity-purified using Protein G Fast Flow gel (GE Healthcare, Bioscience), PBS(−) as an absorption buffer and 0.1 M glycine buffer (pH 2.8) as an elution buffer. The eluted fraction was adjusted to about pH 7.2 by adding 1 M Tris (pH 9.0). The antibody solution thus prepared was replaced by PBS using a Sephadex G25 desalting column (NAP column; GE Healthcare Bioscience) and sterilized by filtration with a membrane filter MILLEX-GV with 0.22 μm pore size (Millipore) to obtain purified C10 and C15 antibody. The concentration of the purified antibody was calculated by measuring 280 nm absorption and by assuming 1 mg/mL as 1.4 OD.

Example 5

Obtaining the Antibody Gene Encoding C10 Antibody and Determination of the Sequence Thereof (1) Synthesis of cDNA of C10 Antibody To obtain the DNA fragment containing the variable regions of human antibody heavy chain and light chain which are expressed in C10 hybridoma, cloning by the 5' RACE method (5' rapid amplification of cDNA ends) was carried out using primers specific to the constant regions of heavy and light chain of human antibody. More particularly, the cloning was carried out using the BD SMART RACE cDNA Amplification Kit (Becton Dickinson Bioscience Clonetech) following the manufacturer's instruction.

RNA extraction reagent, ISOGEN (Nippon Gene), was added to C10 hybridoma and 15 μg of total RNA was purified as the material for cDNA synthesis according to the manufacturer's instruction. The 1st strand of cDNA was prepared using about 1 μg of each purified total RNA as a template. All the reagents and enzymes except RNA used were provided by the BD SMART RACE cDNA Amplification Kit.

In the 1st strand cDNA synthesis,

| Total RNA | 1 μg/3 μl |
|---|---|
| 5'CDS | 1 μl |
| SMART Oligo | 1 μl | the reaction mixture with the above composition was incubated at 70° C. fir 2 min, and then

| 5 × Buffer | 2 μl |
|---|---|
| DTT | 1 μl |
| dNTP mix | 1 μl |
| PowerScript Reverse Transcriptase | 1 μl | were added and incubated at 42° C. fir 1.5 h.

Further, 50 μl of Tricine-EDTA Buffer was added and then incubated at 72° C. for 7 min to obtain the 1st strand of cDNA.

(2) Amplification of the Heavy Chain Gene and the Light Chain Gene by PCR and Confirmation of the Nucleotide Sequences.

(2)-1; Amplification of the Heavy Chain Gene and the Light Chain Gene by PCR.

To amplify the cDNA of the gene encoding C10 antibody, following reaction mixture was prepared and subjected to PCR, using a PCR primer set of the 3' primer having the sequence specific to human antibody (the particular sequence is described later) and the 5' primer (Universal primer A mix) that hybridizes specifically to the sequence added to the 5' terminal of the cDNA synthesized by the BD SMART RACE cDNA Amplification Kit, and KOD-Plus-DNA polymerase (Toyobo) as PCR enzyme.

| sterile H2O | 28 μl |
|---|---|
| 1st strand cDNA | 2.5 μl |
| KOD-Plus- buffer (10X) | 5 μl |
| dNTP Mix (2 mM) | 5 μl |
| MgSO4 (25 mM) | 2 μl |
| KOD-Plus- (1 unit/μl) | 1 μl |
| Universal primer A mix (UPM) (10X) | 5 μl |
| Gene specific primers (GSP) (10 μM) | 1.5 μl |
| Total volume | 50 μl |

For the amplification of the heavy chain gene, the set of UPM primer in the SMART RACE cDNA Amplification Kit and IgG1p primer (SEQ ID NO: 5) was used, while for the amplification of the light chain gene, the set of UPM primer and hk-2 (SEQ ID NO: 6) primer was used.

IgG1p:
(SEQ ID NO: 5)
TCTTGTCCACCTTGGTGTTGCTGGGCTTGTG hk-2:
(SEQ ID NO: 6)
GTTGAAGCTCTTTGTGACGGGCGAGC

Also, the reaction condition used is as follows.

5 cycles of 94° C./30 sec and 72° C./3 min were repeated, 5 cycles of 94° C./30 sec, 70° C./30 sec and 72° C./3 min were repeated, and 25 cycles of 94° C./30 sec, 68° C./30 sec and 72° C./3 min were repeated.

Further, this reaction mixture 2 μl was diluted by adding 98 μl of Tricine-EDTA Buffer, and the second (nested) PCR was carried out using 5 μl of the diluted mixture as a template. The composition of the PCR reaction solution is as follows:

| sterile H2O | 30 μl |
|---|---|
| The first PCR reaction solution (50 fold dilution) | 5 μl |
| KOD-Plus- buffer (10X) | 5 μl |
| dNTP Mix (2 mM) | 5 μl |
| MgSO4 (25 mM) | 2 μl |
| KOD-Plus- (1 unit/μl) | 1 μl |
| Nested Universal primer A (NUP; 10 μM) | 1 μl |
| Gene specific primers (GSP) (10 μM) | 1 μl |
| Total volume | 50 μl |

As a primer set for the amplification of the heavy chain gene in the above reaction, NUP primer (in the SMART RACE cDNA Amplification Kit; Becton Dickinson Bioscience Clonetech) and hh2 primer (SEQ ID NO: 7) were used, and for the amplification of the light chain gene, UPM primer and hk-5 primer (SEQ ID NO: 8) were used. The reaction temperature condition was as follows: at 94° C. as the initial temperature for 1 min, then 20 cycles of 94° C./5 sec, 68° C./10 sec and 72° C./3 min were repeated. Finally heating at 72° C./7 min was carried out.

hh2:
(SEQ ID NO: 7)
GCTGGAGGGCACGGTCACCACGC hk-5:
(SEQ ID NO: 8)
AGGCACACAACAGAGGCAGTTCCAGATTTC (2)-2; Determination of the Nucleotide Sequence of the Antigen Gene The amplified heavy chain PCR fragment (hereinafter, referred to as HV[C]: consisting of the 5'-untranslated region-leader sequence, variable region (HV) and a part of constant region ([C]) of the H chain), and the amplified light chain PCR fragment (hereinafter, referred to as LV[C]: consisting of the 5'-untranslated region-leader sequence, variable region (LV) and a part of constant region ([C]) of the L chain) were recovered by ethanol precipitation, and then subjected to agarose gel electrophoresis. Recovered fragments were purified by a DNA purification kit using a membrane, QIAquick Gel Extraction Kit (Qiagen). The purified HV[C] amplified fragment or LV[C] amplified fragment was subcloned in PCR 4 Blunt-TOPO vector of Zero Blunt TOPO PCR Cloning Kit (Invitrogen) and the nucleotide sequence of the insert DNA was analyzed for plasmid DNA of the clone obtained. The primers used for DNA nucleotide sequence were M13-20FW (SEQ ID NO: 9) and M13RV (SEQ ID NO: 10).

M13-20FW:
(SEQ ID NO: 9)
GTAAAACGAC GGCCAGTG

M13RV:
(SEQ ID NO: 10)
CAGGAAACAGCTATGAC

DNA nucleotide sequence encoding the heavy chain variable region and light chain variable region, and amino acid sequence of heavy chain variable region and light chain variable region of C10 antibody are show below.

<C10 heavy chain nucleotide sequence> (from the ATG initiation codon to the DNA sequence encoding the carboxy terminal amino acid residues of the variable region) (SEQ ID NO: 11)

```
         10         20         30         40
ATGGACTGGA CCTGGAGGGT CTTCTGCTTG CTGGCTGTAG
         50         60         70         80
CTCCAGGTGC TCACTCCCAG GTGCAGCTGG TGCAGTCTGG
         90        100        110        120
GGCTGAGGTG AAGAAGCCTG GGGCCTCAGT GAAGGTTTCC
        130        140        150        160
TGCAAGGCAT CTGGATACAC CTTCACCAAC CACTATATGC
        170        180        190        200
ACTGGGTGCG ACAGGCCCCT GGACAAGGGC TTGAGTGGAT
        210        220        230        240
GGGAATAATC AACCCTATTA GTGGTAGCAC AAGTAACGCA
        250        260        270        280
CAGAAGTTCC AGGGCAGAGT CACCATGACC AGGGACACGT
        290        300        310        320
CCACGAGCAC AGTCTACATG GAGCTGAGCA GCCTGAGATC
        330        340        350        360
TGAGGACACG GCCGTGTATT ATTGTGCGAG AGATATTGTG
        370        380        390        400
GATGCTTTTG ATTTCTGGGG CCAAGGGACA ATGGTCACCG
        408
TCTCTTCA
```

<C10 heavy chain amino acid sequence> (to the leader sequence and variable region) (SEQ ID NO: 12) (Underlined amino acid residues represent the leader sequence as a secretion signal)

```
         10         20         30         40
MDWTWRVFCL LAVAPGAHSQ VQLVQSGAEV KKPGASVKVS
         50         60         70         80
CKASGYTFTN HYMHWVRQAP GQGLEWMGII NPISGSTSNA
         90        100        110        120
QKFQGRVTMT RDTSTSTVYM ELSSLRSEDT AVYYCARDIV
        130        136
DAFDFWGQGT MVTVSS
```

<C10 light chain nucleotide sequence> (from the ATG initiation codon to the DNA sequence encoding the carboxy terminal amino acid residues of the variable region) (SEQ ID NO: 13)

```
         10         20         30         40
ATGGACATGA GGGTCCCCGC TCAGCTCCTG GGGCTTCTGC
         50         60         70         80
TGCTCTGGCT CCCAGGTGCC AGATGTGCCA TCCAGTTGAC
         90        100        110        120
CCAGTCTCCA TCCTCCCTGT CTGCATCTGT AGGAGACAGA
        130        140        150        160
GTCACCATCA CTTGCCGGGC AAGTCAGGGC ATTAGCAGTG
        170        180        190        200
CTTTAGTCTG GTATCAGCAG AAACCAGGGA AAGCTCCTAA
        210        220        230        240
GCTCCTGATC TATGATGCCT CCAGTTTGGA AAGTGGGGTC
        250        260        270        280
CCATCAAGGT TCAGCGGCAG TGGATCTGGG ACAGATTTCA
        290        300        310        320
CTCTCACCAT CAGCAGCCTG CAGCCTGAAG ATTTTGCAAC
        330        340        350        360
TTATTACTGT CAACAGTTTA ATGATTACTT CACTTTCGGC
        370        380        384
CCTGGGACCA AAGTGGATAT CAAA
```

<C10 light chain amino acid sequence> (to the leader sequence and variable region) (SEQ ID NO: 14) (Underlined amino acid residues represent the leader sequence as a secretion signal)

```
         10         20         30         40
MDMRVPAQLL GLLLLWLPGA RCAIQLTQSP SSLSASVGDR
         50         60         70         80
VTITCRASQG ISSALVWYQQ KPGKAPKLLI YDASSLESGV
         90        100        110        120
PSRFSGSGSG TDFTLTISSL QPEDFATYYC QQFNDYFTFG
        128
PGTKVDIK
```

Further, in the gene sequence of C10 antibody subcloned in PCR 4 Blunt-TOPO vector, a part of the constant region of the human antibody sequence was cloned and the DNA nucleotide sequence of this region was also analyzed. The result indicated that the presence of the sequence encoding the amino acid residue 118 to 191 in the heavy chain constant region which is shown by the EU index by Kabat et al., was confirmed and was in complete agreement with the amino acid sequence of human IgG1, and thus it was determined that the subclass of C10 antibody was IgG1. In addition, the antibody gene encoding C15 antibody was obtained and the sequence thereof was determined by using the same method.

Example 6

Construction of Eecombinant C10 Antibody Expression Vector

Figure 1:
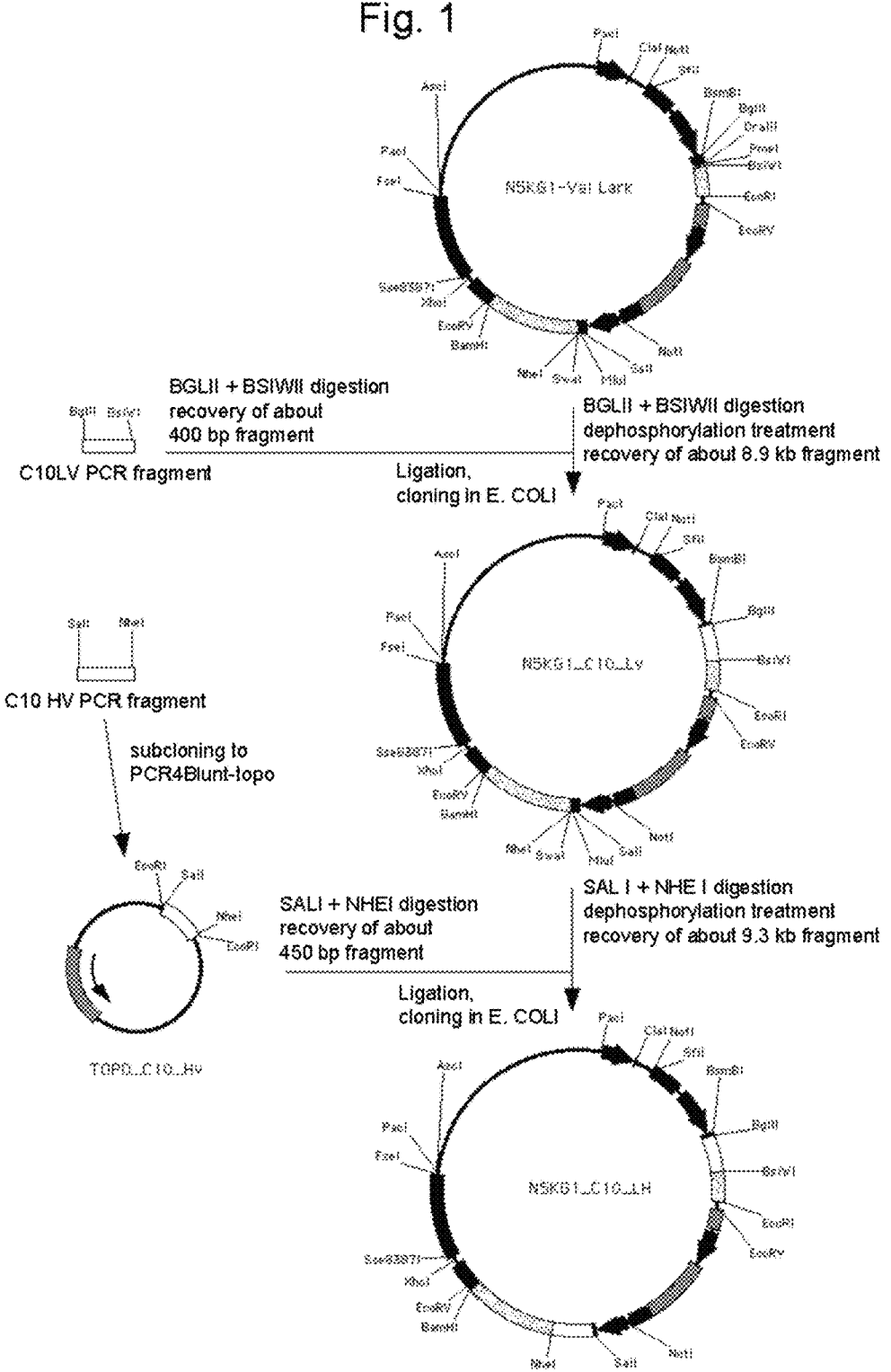
FIG. 1 is a schematic diagram of the construction steps of C10 expression vector.

Production of C10 expression vector (Process scheme is shown in FIG. 1)

Figure 2:
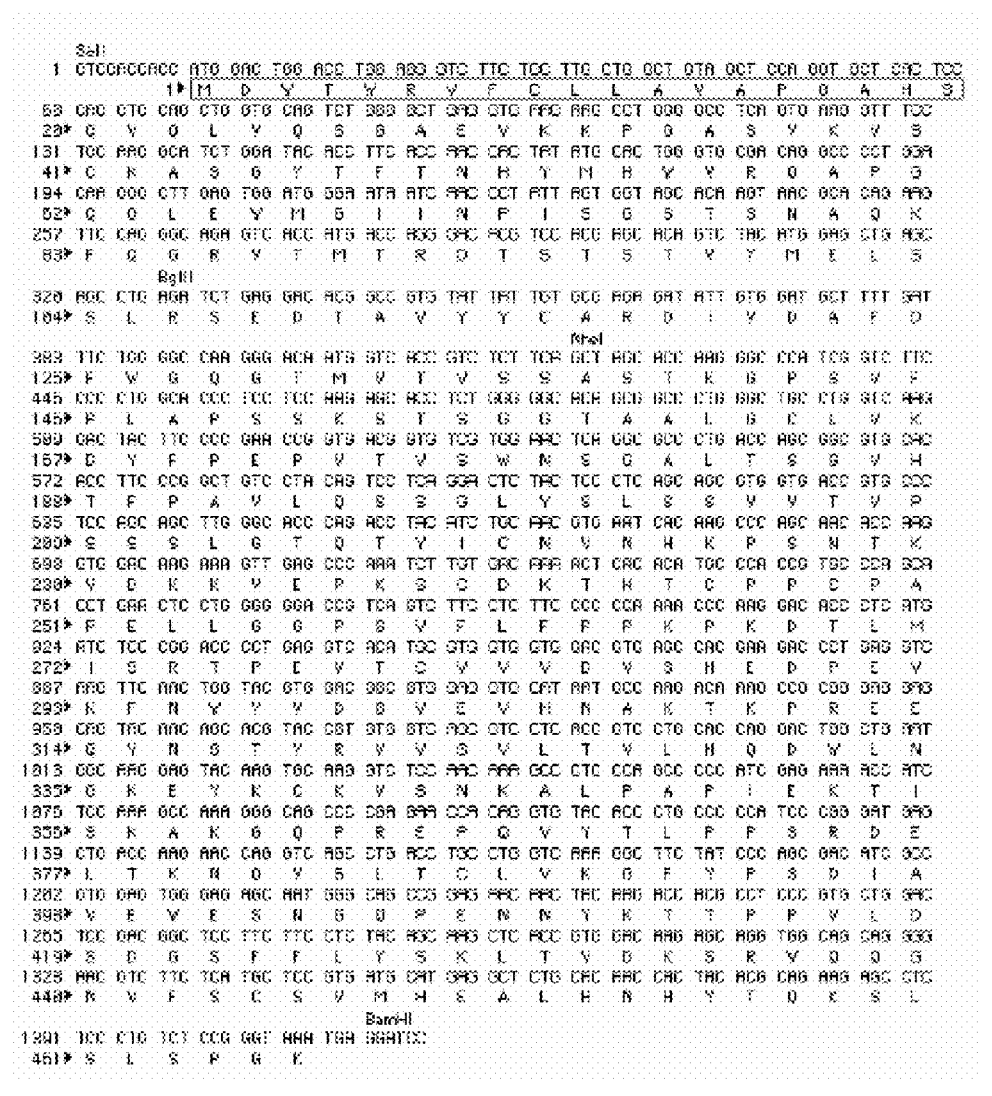

The DNA of LV (light chain leader sequence+variable region) of C10 antibody was amplified by PCR by KOD-Plus-DNA polymerase using obtained plasmid DNA containing LV[C] chain of C10 antibody as a template and primers C10_L5_Bgl (SEQ ID NO: 15) and C10_L3_Bsi (SEQ ID NO: 16) which were designed to add restriction enzyme sites (5' terminal BglII, 3' terminal BsiWI) for linkage to the ends. The reaction temperature condition was: after heating for 1 min at the starting temperature 94° C., a cycle of 94° C./5 sec and 68° C./45 sec was repeated 35 times and a final heating 72° C./7 min. The amplified DNA fragment was digested with restriction enzymes BglII and BsiWI and purified by recovering 400 by DNA from agarose gel electrophoresis. While the vector DNA, N5KG1-Val Lark vector (IDEC Pharmaceuticals, a modified vector of N5KG1 (U.S. Pat. No. 6,001,358)) was similarly digested with restriction enzymes BglII and BsiWI sequentially, subjected to dephosphorylation treatment with Alkaline Phosphatase (*E. coli* C75) (Takara Shuzo Co., Ltd.) and then recovered as a little smaller than about 9 kb DNA after purification by agarose gel electrophoresis and DNA purification kit. These 2 fragments were ligated with T4 DNA ligase and transfected to *E. coli* DH10B to obtain transformants. Plasmid DNA of the transformants, which contained the insert DNA, was subjected to DNA nucleotide sequence analysis, and plasmid DNA, N5KG1_C10_Lv, in which LV of C10 antibody was inserted in frame at 5' upstream of human antibody light chain constant region of N5KG1-Val Lark was obtained. Next, the HV (the leader sequence+ variable region of heavy chain) of C10 antibody was inserted to the plasmid vector in which LV was inserted (N5KG1_C10-_Lv). The HV was amplified by PCR using the plasmid DNA containing the HV[C] of C10 antibody subcloned in pCR4Blunt-TOPO vector as a template and the primers, C10_H5_Sal (SEQ ID NO: 17) and C10_H3_Nhe (SEQ ID NO: 18) designed to add restriction enzyme sites (SalI at the 5' terminal, NheI at 3' terminal) for linkage to the ends. The reaction temperature condition was: after heating for 1 min at the starting temperature 94° C., a cycle of 94° C./5 sec and 68° C./45 sec was repeated 35 times and a final heating 72° C./7 min. Purified HV amplified DNA fragment was subcloned in pCR4Blunt-TOPO vector, and the insert DNA of thus obtained clones of plasmid DNA analyzed by sequencing. The primers used for DNA sequencing were M13-20FW and M13RV described above. The inserted part of the subclones was analyzed by DNA sequencing, and the plasmid DNA (TOPO_C10_Hv), which had no difference with the template HV and the primer parts were also the same sequence as designed, was selected. This DNA was digested with restriction enzymes, SalI and NheI, subjected to agarose gel electrophoresis, and the DNA fragment which was about 420 by was recovered and purified, and was ligated using T4 DNA ligase to N5KG1_C10_Lv DNA (about 9 kb) which was similarly subjected to restriction enzyme treatment (SalI and NheI) and dephosphorylation. The ligation product was introduced into *E. coli* DH10B and the target plasmid DNA was selected from the transformants thus obtained. The antibody expressing plasmid DNA, N5KG1_C10_IH (clone #1) obtained in this way was mass produced and purified, and it was confirmed that no change was introduced during the cloning process in the DNA nucleotide sequence of the entire region of L chain and H chain and around the inserted site (FIGS. 2 and 3). Confirmation of the DNA sequence was carried out by using primers of SEQ ID NO: 19-25. Simplified map of C10 antibody expression vector is shown in FIG. 4. In addition, a recombinant C15 antibody expression vector was constructed by using the same method.

C10_L5_Bgl:
(SEQ ID NO: 15)
GAGAGAGAGATCTCTCACCATGGACATGAGGGTCCCCGCT

C10_L3_Bsi:
(SEQ ID NO: 16)
AGAGAGAGAGCGTACGTTTGATATCCACTTTGGTCCCAGGGC

C10_H5_Sal:
(SEQ ID NO: 17)
AGAGAGAGAGGTCGACCACCATGGACTGGACCTGGAGGGTCTTC

C10_H3_Nhe:
(SEQ ID NO: 18)
AGAGAGAGAGGCTAGCTGAAGAGACGGTGACCATTGTCCC hh-4:
(SEQ ID NO: 19)
GGTGCCAGGGGGAAGACCGATGG hh-1:
(SEQ ID NO: 20)
CCAAGGGCCCATCGGTCTTCCCCCTGGCAC

CMVH903F:
(SEQ ID NO: 21)
GACACCCTCATGATCTCCCGGACC

CMVHR1303:
(SEQ ID NO: 22)
TGTTCTCCGGCTGCCCATTGCTCT

SEQU4618:
(SEQ ID NO: 23)
TCTATATAAGCAGAGCTGGGTACGTCC hk-1:
(SEQ ID NO: 24)
TGGCTGCACCATCTGTCTTCATCTTC

SEQU1783:
(SEQ ID NO: 25)
GGTACGTGAACCGTCAGATCGCCTGGA

Example 7

Preparation of Recombinant C10 Antibody

C10 antibody expressing cells were produced by introducing the constructed C10 antibody expression vector to host cells. A strain of dihydrofolate reductase (DHFR) deletion mutant CHO DG44 cells (hereinafter, referred to as CHO cells, IDEC Pharmaceuticals), conditioned to a serum-free medium, EX-CELL325PF medium (JRH, containing 2 mM glutamine, 100 units/nil penicillin, 100 μg/ml streptomycin, hypoxanthine and thymidine (HT) supplement (1:100) (Invitrogen)) was used as host cells for expression. Introduction of the vector to the host cells was carried out by electroporation. The gene was introduced to 4×106 CHO cells by electroporation by linearizing about 2 μg of the C10 expression vector with a restriction enzyme AscI and using a BioRad Electroporator at 350 V, 500 μF, and then cells were seeded to 96 cell culture plates. After introducing the vector to the cells, G418 was added and the culture was continued. After confirming colonies, strains expressing antibody were selected. The selected CHO cell lines were cultured in EX-CELL-325 PF medium (containing 2 mM glutamine, 100 units/nil penicillin, 100 μg/nil streptomycin, hypoxanthine and thymidine (HT) supplement (1:100) (Invitrogen)) under 5% CO2. The culture supernatant was absorbed to a Mabselect Protein A column (GE Healthcare Bioscience), washed with PBS and eluted with 20 mM Na-citrate and 50 mM NaCl (pH 3.4) buffer. The eluate was neutralized to pH 7.0 with 50 mM sodium phosphate pH 7.0.

The conductivity was adjusted to 4.0 ms/cm or below by diluting about 1.5 fold with deionized water. Next, the sample was applied to a linked column of Q-Sepharose (Hitrap Q HP, GE Healthcare Bioscience) and SP-Sepharose (Hitrap SP FF, GE Healthcare Bioscience) for absorption, washed with 20 mM sodium phosphate buffer (pH 5.0) and then eluted with PBS(−). The antibody solution thus prepared was filter sterilized through a 0.22 μm pore size membrane filter, MILLEX-GV (Millipore). The concentration of purified C10 antibody was calculated by measuring 280 nm absorption and by assuming 1 mg/mL as 1.4 OD. In addition, a recombinant C15 antibody was prepared by using the same method.

Example 8

Construction of Cynomolgus Monkey FGF23 Protein Expression Vector (1) Construction of Cynomolgus Monkey FGF23 Protein Expression Vector To EDTA treated venous blood of cynomolgus monkey, 5% Dextran T-2000 (GE Healthcare Bioscience) suspended in PBS (−) was mixed at the ratio of 2:1 to precipitate red blood cells. Then, the supernatant was layered on top of a lymphocyte separation solution (Ficoll-Plaque) (GE Healthcare Bioscience) and centrifuged to obtain the lymphocyte fraction. Lymphocytes thus obtained were suspended in ISOGEN-LS (Nippon Gene), and total lymphocyte RNA of cynomolgus monkey was obtained according to the attached protocol. From this total lymphocyte RNA of cynomolgus monkey, the lymphocyte cDNA library of cynomolgus monkey was prepared using First Strand cDNA Synthesis Kit (Invitrogen) according to the attached protocol. cDNA encoding cynomolgus monkey FGF23 was amplified using the lymphocyte cDNA library of cynomolgus monkey as a template, monkey FGF23FW primer (SEQ ID NO: 26) and monkey FGF23RV primer (SEQ ID NO: 27), and KOD plus DNA polymerase (Toyobo), and incubating at 94° C. for 5 min, then carrying out 45 cycles of a PCR step of heating at 94° C. for 20 sec, at 55° C. for 30 sec and at 72° C. for 50 sec. The monkey FGF23FW primer anneals to a sequence present in the 5' upstream region of the nucleotide sequence encoding human FGF23 and adds the EcoRI restriction site to the 5' side of the FGF23 coding region in the amplified fragment. The monkey FGF23RV primer contains a sequence which anneals to the sequence containing the stop codon of the human FGF23 coding region, and the Not I restriction site. This amplified fragment was digested with EcoRI and NotI, and cloned by inserting at the EcoRI and NotI restriction sites of pEAK8/IRES/EGFP vector, which is an expression vector pEAK8 (Edge Biosystem) to which internal ribosome entry site (IRES) and enhanced green fluorescent protein (EGFP) are linked. The nucleotide sequence of thus obtained plasmid was determined to confirm that it encodes a cynomolgus monkey FGF23 protein. This vector was called pEAK8/IRES/EGFP/monkeyFGF23. The nucleotide sequence and amino acid sequence of cynomolgus monkey FGF23 obtained in the present Example are shown in SEQ ID NO: 28 and 29, respectively.

```
monkeyFGF23FW:
                                        (SEQ ID NO: 26)
GGAATTCCACCATGTTGGGGGCCCGCCTCAGGCT monkeyFGF23RV:
                                        (SEQ ID NO: 27)
ATTTGCGGCCGCTAGATGAACTTGGCGAAGGGGC Nucleotide sequence of cynomolgus monkey FGF23
                                        (SEQ ID NO: 28)
ATGTTGGGGGCCCGCCTCAGGCTCTGGGTCTGTGCCTTGTGCAGCGTCT

GCAGCATGAGCGTCATCAGAGCCTATCCCAATGCCTCCCCATTGCTCG

GCTCCAGCTGGGGTGGCCTGATCCACCTGTACACAGCCACAGCCAGGA

ACAGCTACCACCTGCAGATCCACAAGAATGGCCACGTGGATGGCGCAC

CCCATCAGACCATCTACAGTGCCCTGATGATCAGATCAGAGGATGCTG

GCTTTGTGGTGATTACAGGTGTGATGAGCAGAAGATACCTCTGCATGG

ATTTCGGAGGCAACATTTTTGGATCACACTATTTCAACCCGGAGAACTG

CAGGTTCCGACACTGGACGCTGGAGAACGGCTACGACGTCTACCACTC

TCCTCAGCATCACTTTCTGGTCAGTCTGGGCCGGGCGAAGAGGGCCTTC

CTGCCAGGCATGAACCCACCCCCCTACTCCCAGTTCCTGTCCCGGAGG

AACGAGATCCCCCTCATCCACTTCAACACCCCCAGACCACGGCGGCAC

ACCCGGAGCGCCGAGGACGACTCGGAGCGGGACCCCCTGAACGTGCT

GAAGCCCCGGGCCCGGATGACCCCGGCCCCGGCCTCCTGCTCACAGGA

GCTCCCGAGCGCCGAGGACAACAGCCCGGTGGCCAGCGACCCGTTAGG

GGTGGTCAGGGGCGGTCGGGTGAACACGCACGCTGGGGGAACGGGCC

CGGAAGCCTGCCGCCCCTTCGCCAAGTTCATCTAG

Amino acid sequence of cynomolgus monkey FGF23
                                        (SEQ ID NO: 29)
MLGARLRLWV CALCSVCSMS VIRAYPNASP LLGSSWGGLI

HLYTATARNS YHLQIHKNGH VDGAPHQTIY SALMIRSEDA

GFVVITGVMS RRYLCMDFGG NIFGSHYFNP ENCRFRHWTL

ENGYDVYHSP QHHFLVSLGR AKRAFLPGMN PPPYSQFLSR

RNEIPLIHFN TPRPRRHTRS AEDDSERDPL NVLKPRARMT

PAPASCSQEL PSAEDNSPVA SDPLGVVRGG RVNTHAGGTG

PEACRPFAKF I
```

(2) Preparation of Supernatant of Cynomolgus Monkey FGF23 Expressing Cells pEAK8/IRES/EGFP/monkey FGF23 was transiently transfected to PEAK rapid cells (Edge Biosystem) by the calcium phosphate method, and their culture supernatant was obtained.

Example 9

Investigation for Binding of C10 to Antibody Cynomolgus Monkey FGF23

The fact that C10 antibody binds not only to human FGF23 but also cynomolgus monkey FGF23 was investigated by the following method using sandwich ELISA. C10 antibody prepared in Example 4, 2C3B antibody and human IgG1 control antibody were diluted in 50 mM NaHCO3 solution to a concentration of 5 μg/ml and added to each well of 96 well microtiter plates for ELISA (Maxisorp (Registered Trade Name), Nunc), incubated at 4° C. for 12 hours. Thus, C10 antibody, 2C3B antibody and human IgG1 control antibody as a control were absorbed to microplates.

Figure 5A:
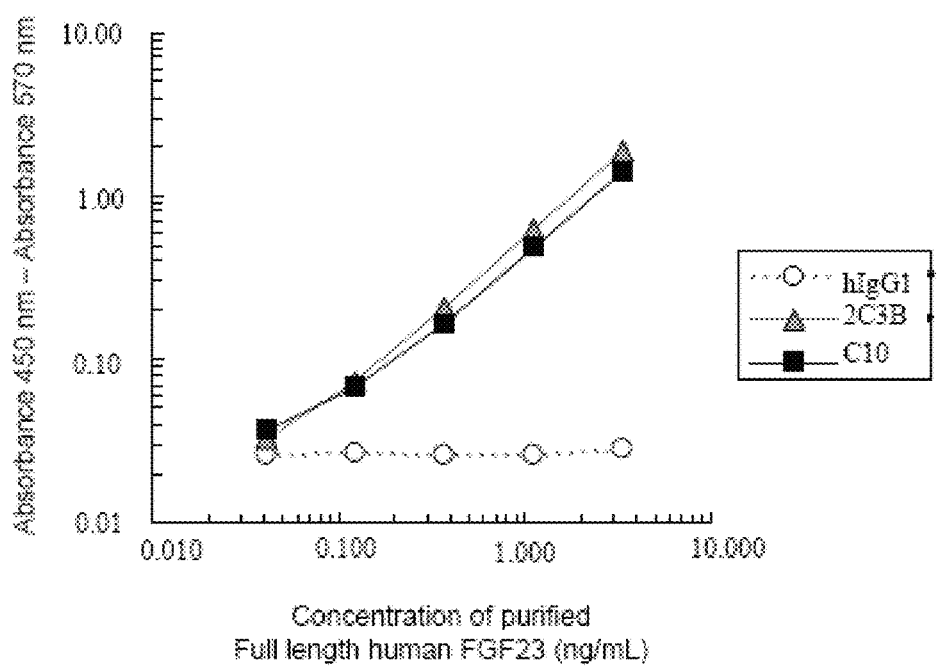
FIG. 5A shows the result of the measurement for detecting purified full length human FGF23 protein by the sandwich ELISA method using 2C3B antibody or C10 antibody as the immobilizes antibody, and 3C1E antibody as the detection antibody.
Figure 5B:
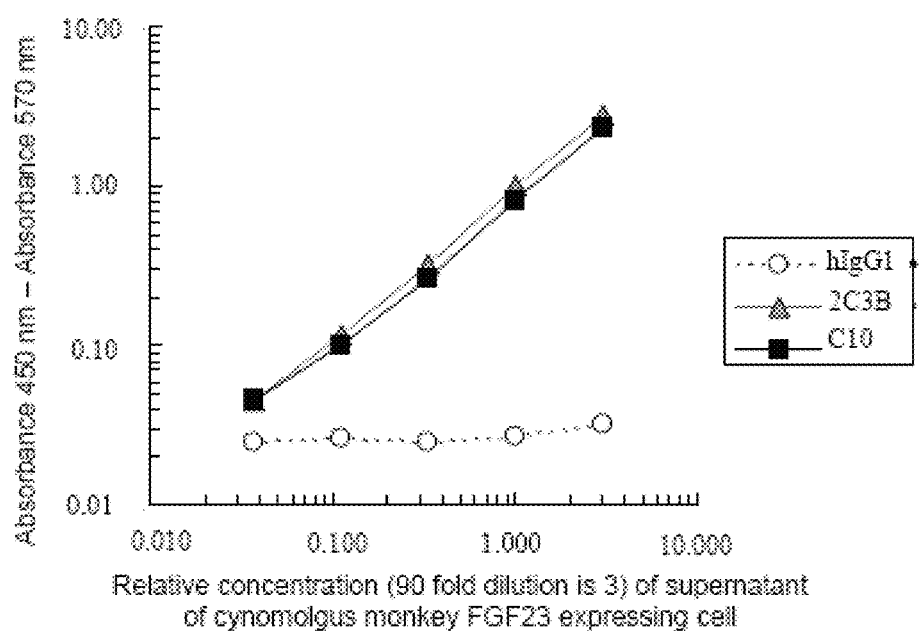
FIG. 5B shows the result of the measurement for detecting the culture supernatant of cynomolgus monkey FGF23 expressing cells by the sandwich ELISA method using 2C3B antibody or C10 antibody as the solid phase antibody, and 3C1E antibody as the detection antibody.

Next, these solutions were removed, and a blocking reagent (SuperBlock (Registered Trade mark) Blocking buffer, PIERCE) was added to each well, incubated at room temperature for 30 min and then each well was washed twice with Tris-buffered saline (T-TBS) containing 0.1% Tween20. To each well of the microtiter plate with anti-FGF23 antibodies were coated, full length human FGF23 protein purified in Example 2 or the expressing cell supernatant of cells expressing cynomolgus monkey FGF23 prepared in Example 8 was added after diluting to appropriate concentrations, reacted to antibody in solid phase for 2 hours, and then each well was washed twice with Tris-buffered saline (T-TBS) containing 0.1% Tween20. Next, biotin labeled 3C1E antibody at 3 μg/ml was added and incubated at room temperature for 1.5 hours to bind biotin labeled 3C1E antibody to human or cynomolgus monkey FGF23 bound to the antibody in solid phase. After washing with T-TBS, horseradish peroxidase labeled streptavidin (DAKO) diluted 5000 fold was reacted for 1 hour and washed 3 times with T-TBS. Next, a substrate buffer containing tetramethylbenzidine (DAKO) was added to each well and incubated at room temperature for 30 min. The reaction was stopped by addition of 0.5 M sulfuric acid to each well. Absorption at the wavelength of 450 nm with reference wavelength of 570 nm was measured using a microplate reader (MTP-300, Colona Electric Co.). Reactivity of human full length FGF23 protein and the culture supernatant of cynomolgus monkey FGF23 expressing cells were compared by diluting with factor of 3. The result is shown in FIG. 5A and B. As clearly shown in FIG. 5A, the reactivity of C10 antibody or 2C3B antibody in solid phase to human full length FGF23 protein is about the same. To serially diluted culture supernatant of cynomolgus monkey FGF23 expressing cells under the conditions, not much difference is observed between the reactivity of C10 antibody and 2C3B antibody (FIG. 5B). That is, C10 antibody, like 2C3B antibody, was proven to be able to bind to human and cynomolgus monkey FGF23.

Example 10

Comparison of the Effect of C10 Antibody and 2C3B Antibody on Normal Cynomolgus Monkey Blood Phosphorous Concentration and Blood 1α, 25 Dihydroxy Vitamin D Concentration FGF23 has activities of excreting phosphorous from the kidney, reducing serum phosphorous concentration as well as inhibiting vitamin D activating enzyme and reducing blood 1α, 25 dihydroxy vitamin D (hereinafter referred to as 1,25D) concentration (International Publication No. WO02/14504 Pamphlet). It has been demonstrated that administration of antibody, such as 2C3B antibody and the like, which has a suppressive effect, that is, neutralizing activity, on FGF23, to normal mice causes inhibition of endogenous FGF23 action and an increase of serum phosphorous concentration and serum 1,25D concentration (International Publication No. WO03/057733 Pamphlet). Thus, it has been strongly suggested that antibody having neutralizing activity on FGF23 has therapeutic effect on human diseases including tumor-induced osteomalachia, XLH and the like which are caused by excessive FGF23. Therefore, C10 antibody obtained in the present invention was investigated for FGF23 neutralizing activity in vivo. In particular, since its pharmacological effect on human is expected, the neutralizing effect was measured in monkeys, which are evolutionally more closely related to humans compared to species such as rodents, by using the suppression of the function of endogenous FGF23, increase of serum phosphorous concentration and increase of serum 1,25D concentration as indexes. Experiments were conducted using a mouse antibody, 2C3B antibody, as a comparative control for C10 antibody.

Figure 6:
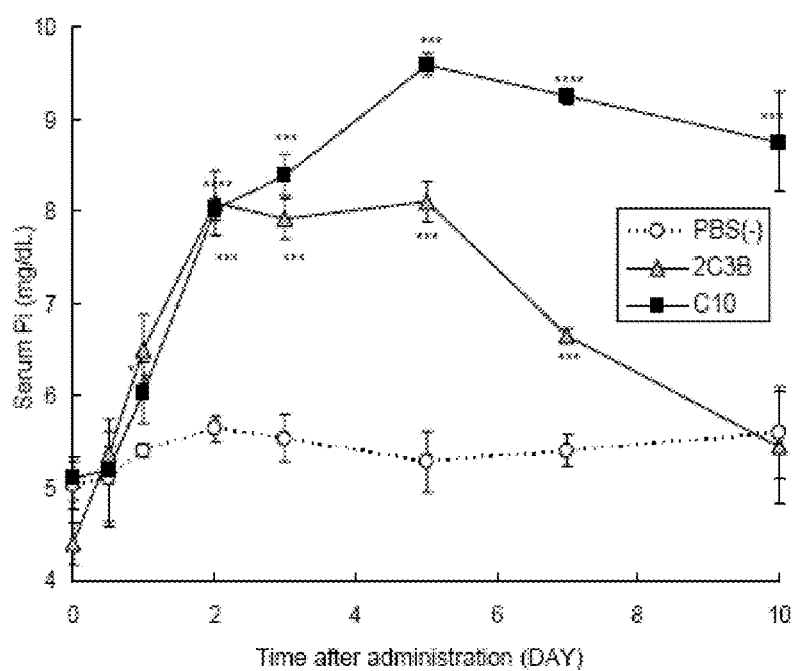
FIG. 6 is a graph showing chronological measurements of serum phosphorous concentration in cynomolgus monkeys administered with solvent, 2C3B antibody or C10 antibody. Measured values are shown in average +/− standard error. Further, when significant difference test between the solvent administered group and the test groups was conducted at the same date using Student-test, values found to be significant difference ($p<0.05$) are marked with * on the graph.
Figure 7:
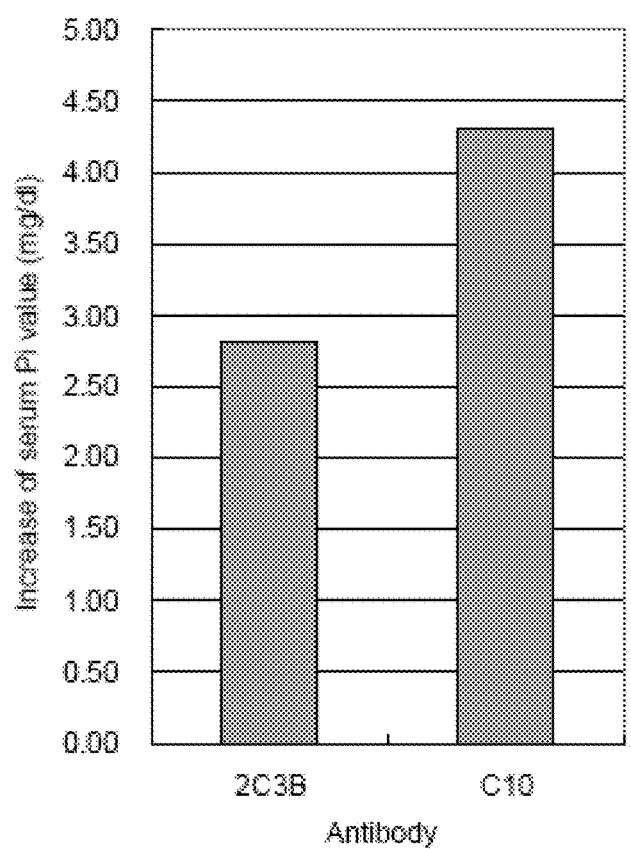
FIG. 7 is a graph showing an increase in the serum phosphorous concentration of cynomolgus monkeys 5 days after 2C3B antibody or C10 antibody administration, based on the serum phosphorous concentration of cynomolgus monkey 5 days after the administration of the solvent as the standard.
Figure 8:
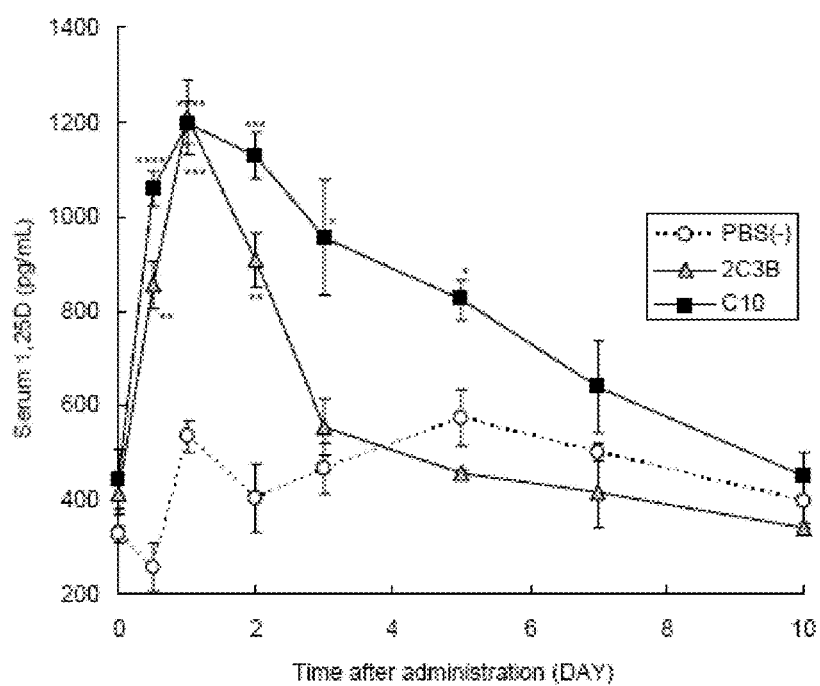
FIG. 8 is a graph showing chronological measurements of serum 1,25D concentration in cynomolgus monkeys administered with solvent, 2C3B antibody or C10 antibody. Measured values are shown in average +/− standard error. Further, when significant difference test between the solvent administered group and the test groups was conducted at the same date using Student-test, values found to be significant difference (p<0.05) are marked with * on the graph.

Effect of C10 antibody and 2C3B antibody on the increase of serum phosphorous concentration was compared in untreated normal cynomolgus monkeys by the following method. C10 antibody produced in Example 4 was used. Experimental animals used were female cynomolgus monkeys of 2-3 years old and body weight 2-4 kg. 3 animals were used in each group of the solvent administration and 2C3B antibody administration, and 4 animals were used in the C10 administration group. C10 and 2C3B antibodies were prepared in PBS (−) at a concentration of 3 mg/ml and used as an administration solution. The solvent, PBS (−), was used as a negative control. C10 and 2C3B antibodies were administered once from the brachial cephalic vein at a flow rate of 1 ml/min and amount of 3 mg/kg and 1 ml/kg. Serum phosphorous concentration was measured using L type Wako inorganic phosphorous reagent (Wako Pure Chemical Industries) and a Hitachi Clinical Analyzer Model 7180 (Hitachi, Ltd.). Serum 1,25D concentration was measured using 1, 25 (OH)2D RIA Kit [TFB] (Immunodiagnostic System). Measurements were carried out at day 0.5, 1, 2, 3, 5, 7, 10, 14, 21, 28, 35, 42, and 49 after the administration of antibody. Data were shown in average +/− standard error. FIG. 6 shows the transition of serum phosphorous concentration in periodically collected blood samples up to 10 days after the administration of each antibody. In the PBS (−) administered group, the serum phosphorous concentration was almost constant during the test period, while in the C10 antibody and 2C3B antibody administered groups a clear increase of the serum phosphorous concentration was observed when compared with before the administration and PBS (−) administered group. The day when the highest serum phosphorous concentration was observed in both C10 antibody administered group and 2C3B antibody administered group was 5 days after the administration of the antibodies. At this time point, the serum phosphorous concentration in PBS(−) group, 2C3B antibody group and C10 antibody group was 5.28 mg/dl, 8.10 mg/dl and 9.59 mg/dl, respectively. Comparing the serum phosphorous concentration of 2C3B antibody group and the C10 antibody group at 5 days after the administration of antibody with the serum phosphorous concentration of the PBS (−), the increase in the 2C3B antibody group was 2.82 mg/dl, while that of C10 antibody group was 4.31 mg, suggesting that C10 antibody induced about 1.5 times or higher increase in the serum phosphorous concentration compared to the 2C3B antibody (FIG. 7). Thus the increase effect in the serum phosphorous concentration in C10 antibody administered group is markedly higher compared to that in the 2C3B antibody administered group. Further, at 10 days after the administration the serum phosphorous concentration in the 2C3B antibody administered group was at the same level as that in PBS (−) group, while the serum phosphorous concentration in the C10 administered group (8.76 mg/dl) was still maintaining higher level than the highest level (8.10 mg/dl) in the 2C3B antibody administered group (FIG. 6). Further, the increased serum phosphorous concentration by C10 antibody is sustained far longer than that by 2C3B antibody. The duration, in which the significant difference of the serum phosphate concentration from the PBS (−) group was observed, was 7 days for the 2C3B group, while it was surprisingly 35 days, about 5 times longer, in the C10 antibody group. Similarly, for 1,25D concentration, after the administration C10 antibody demonstrated a marked increase and elongation of the sustained increased duration compared to 2C3B antibody (FIG. 8). These results demonstrate that in cynomolgus monkeys C10 antibody have more powerful increasing activity for serum phosphorous concentration and serum 1,25D concentration, that is, having more powerful FGF23 neutralizing activity. The current treatment for hypophosphatemic rickets in XLH at this time requires a large dose of multiple administrations of phosphorous and vitamin D formulations per day to barely maintain the normal range of the phosphorous concentration. There are reports of poor compliance of patients due to the plurality of administrations to take. The fact that in the single administration of C10 antibody in the present study, a sustained raising activity on serum phosphorous concentration and serum 1,25D concentration was observed suggests that C10 antibody has possibly a marked advantage as a therapeutic drug for hypophosphatemia over conventional therapy.

Example 11

Figure 9:
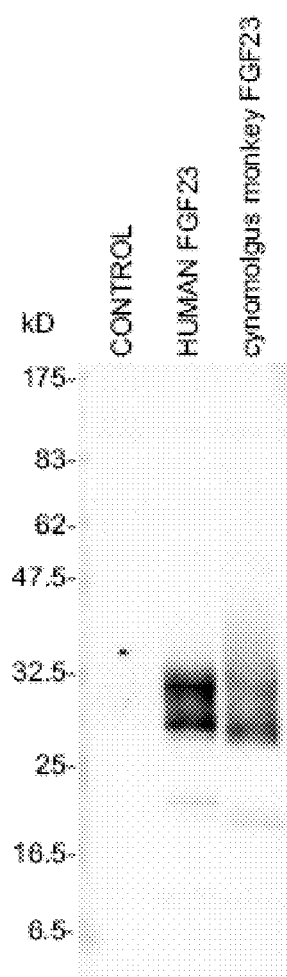
FIG. 9 is a picture showing the detection of the culture supernatant of the cells with no forced expression (control) and the culture supernatant of the human and cynomolgus monkey FGF23 expression cells by C15 antibody using the Western blotting method.

Confirmation of Reactivity of C15 Antibody to Human and Cynomolgus Monkey FGF23 pEAK8/IRES/EGFP/hFGF23 prepared in Example 1 or pEAK8/IRES/EGFP/monkey FGF23 prepared in Example 8 was transiently transfected into PEAK rapid cells (Edge Biosystem) by the calcium phosphate method. Each culture supernatant was collected 3 days after introduction. Western blotting of the collected culture supernatant was performed using C15 antibody prepared in Example 13 as a primary antibody (FIG. 9). As a result, C15 was shown to bind to cynomolgus monkey FGF23, similarly to human FGF23.

Example 12

Comparison of the Effect of C10 Antibody and C15 Antibody on Blood Phosphorous Concentration and Blood 1α, 25 Dihydroxy Vitamin D Concentration in Normal Cynomolgus Monkeys Example 11 demonstrated that C15 antibody has binding activity with human and cynomolgus monkey FGF23 recombinant proteins as does C10 antibody. Subsequently, FGF23 neutralizing activity of C10 antibody and C15 antibody in vivo was compared by administering the antibodies to normal cynomolgus monkeys. The neutralizing activity on cynomolgus monkey endogenous FGF23 was evaluated by using the increase in serum phosphorous concentration as an index. The C10 antibody and C15 antibody produced in Example 7 were used. Normal cynomolgus monkeys of 2-3 years old and body weight 2-3 kg were used as experimental animals. 2 male animals and 1 female animal, totaling 3, were used in each group. The dilution medium used was PBS (-). C10 antibody was prepared at a concentration of 1 mg/ml and 3 mg/ml, and C15 antibody was prepared at a concentration of 3 mg/ml. The antibodies were administered once from the saphenous vein in a volume of 1 mL/kg at a flow rate of about 1 ml/min to achieve a dose of 1 mg/kg and 3 mg/kg for C10 antibody and a dose of 3 mg/kg for C15 antibody. Serum phosphorous concentration was measured using L type Wako inorganic phosphorous reagent (Wako Pure Chemical Industries) and a Hitachi Clinical Analyzer Model 7180 (Hitachi, Ltd.). Blood samples were taken before the administration of antibody, and at day 1, 3, 5, 7, 10, 14, 21 and 28 after the administration of antibody. Measurements of serum phosphorous concentration were conducted for all the blood sampling points. In the C10 antibody 1 mg/kg group, the C10 antibody 3 mg/kg group and the C15 antibody 3 mg/kg group, serum phosphorous concentrations before dosing were 5.37, 5.70 and 5.58 mg/dL, respectively, and there was no difference between groups. In all cynomolgus monkeys, the increase in serum phosphorous concentration was observed after the administration. Thus, not only C10 antibody but also C15 antibody were shown to have neutralizing activity on cynomolgus monkey endogenous FGF23. In the C10 antibody 1 mg/kg group, the C10 antibody 3 mg/kg group and the C15 antibody 3 mg/kg group, the serum phosphorous concentration 3 days after the administration was 9.03, 9.10 and 8.64 mg/dL, respectively. At this time point, the serum phosphorous concentration in the C10 antibody 1 mg/kg group and the C15 antibody 3 mg/kg group reached highest level. On the other hand, the serum phosphorous concentration in the C10 antibody 3 mg/kg group further increased and reached the highest level 5 days after the administration, and the level was 9.75 mg/dL. In the C10 antibody 1 mg/kg group, the C10 antibody 3 mg/kg group and the C15 antibody 3 mg/kg group, the maximum differences of serum phosphorous concentration between before and after administration were 3.67, 4.65 and 3.06 mg/dL, respectively. From this result, the effect of C10 antibody on the increase in serum phosphorous concentration was shown to be higher compared to that of C15 antibody at the same dose of 3 mg/kg. In addition, surprisingly, C10 antibody at a dose of 1 mg/kg increased the serum phosphorous concentration more than C15 antibody at a dose of 3 mg/kg. Next, the duration of serum phosphorus increase over the pre-dosing level was compared. As a result, the duration of phosphorus increment in the C10 antibody 1 mg/kg group, the C10 antibody 3 mg/kg group and the C15 antibody 3 mg/kg group was 14, 28 and 7 days, respectively. From this result, C10 antibody was shown to have a sustained raising activity of serum phosphorous concentration compared to that of C15 antibody at the same dose of 3 mg/kg. In addition, surprisingly, serum phosphorous concentration increased higher at peak and sustained high level much longer by C10 antibody at a dose of 1 mg/kg than by C15 antibody at a dose of 3 mg/kg. The above results demonstrate that in cynomolgus monkeys C10 antibody has more powerful increasing activity for serum phosphorous concentration and sustaining activity for serum phosphorous concentration compared to those of C15 antibody simultaneously obtained with C10 antibody. That is, C10 antibody has significantly powerful neutralizing activity on cynomolgus monkey FGF23 compared to C15 antibody.

Example 13

Preparation of Human FGF23 DNA Fragment (Signal Sequence-Free)

A reaction solution was prepared by KOD-plus-DNA polymerase (Toyobo), following the manufacturer's instruction. Fifty pmol of FGF23(-SP) FW primer (SEQ ID NO: 34) and FGF23(-SP) RV primer (SEQ ID NO: 35), and human FGF23-cDNA (756 by from the initiation codon to the stop codon, SEQ ID NO: 36) as the template were added up to 50 μl of the reaction solution. After incubating the mixture at 94° C. for 3 min, it was subjected to 30 cycles of a PCR step of heating at 98° C. for 15 sec, at 63° C. for 15 sec and at 68° C. for 2 min 30 sec. The mixture was then incubated at 72° C. for 3 min. The obtained 684 bp amplified fragment was separated and collected on a 0.8% gel. The amplified fragment was recovered from the collected gel by QIAquick Gel Extraction Kit (Qiagen), following the manufacturer's instruction. The collected PCR amplified fragment was digested with FseI (New England Biolabs Japan), and the enzyme-treated fragment was recovered by QIAquick PCR Purification Kit (Qiagen), following the manufacturer's instruction. As a result, a partial DNA fragment corresponding to the mature form region without the signal sequence of human FGF23 was obtained.

```
FGF23(-SP) FW:
                                        (SEQ ID NO: 34)
TATCCCAATGCCTCCCCACTGCTCGGCTCCAGCTG

FGF23(-SP) RV:
            (SEQ ID NO: 35, including the FseI site)
TTGGCCGGCCCTAGATGAACTTGGCGAAGGGGCGGCAGCCTTCCG
```

The nucleotide sequence of human FGF23 (nucleotides in the signal sequence region are underlined, and nucleotides in the mature form region excluding the signal sequence region from the full length are surrounded by a rectangular line.) (SEQ ID NO: 36)

ATGTTGGGGGCCCGCCTCAGGCTCTGGGTCTGTGCCTTGTGCAGCGTCTG

CAGCATGAGCGTCCTCAGAGCC|TATCCCAATGCCTCCCCACTGCTCGGCT

CCAGCTGGGGTGGCCTGATCCACCTGTACACAGCCACAGCCAGGAACAGC

TACCACCTGCAGATCCACAAGAATGGCCATGTGGATGGCGCACCCCATCA

GACCATCTACAGTGCCCTGATGATCAGATCAGAGGATGCTGGCTTTGTGG

TGATTACAGGTGTGATGAGCAGAAGATACCTCTGCATGGATTTCAGAGGC

AACATTTTTGGATCACACTATTTCGACCCGGAGAACTGCAGGTTCCAACA

CCAGACGCTGGAAAACGGGTACGACGTCTACCACTCTCCTCAGTATCACT

TCCTGGTCAGTCTGGGCCGGGCGAAGAGAGCCTTCCTGCCAGGCATGAAC

CCACCCCCGTACTCCCAGTTCCTGTCCCGGAGGAACGAGATCCCCCTAAT

TCACTTCAACACCCCCATACCACGGCGGCACACCCGGAGCGCCGAGGACG

ACTCGGAGCGGGACCCCCTGAACGTGCTGAAGCCCCGGGCCCGGATGACC

CCGGCCCCGGCCTCCTGTTCACAGGAGCTCCCGAGCGCCGAGGACAACAG

CCCGATGGCCAGTGACCCATTAGGGGTGGTCAGGGGCGGTCGAGTGAACA

CGCACGCTGGGGGAACGGGCCCGGAAGGCTGCCGCCCCTTCGCCAAGTTC

ATCTAG

The amino acid sequence of human FGF23 based on SEQ ID NO: 36 as the standard (amino acid residues in the signal sequence region are underlined, and amino acid residues in the mature form region excluding the signal sequence region from the full length are surrounded by a rectangular line.) (SEQ ID NO: 37)

MLGARLRLWVCALCSVCSMSVLRA|YPNASPLLGSSWGGLIHLYTATARNS

YHLQIHKNGHVDGAPHQTIYSALMIRSEDAGFVVITGVMSRRYLCMDFRG

NIFGSHYFDPENCRFQHQTLENGYDVYHSPQYHFLVSLGRAKRAFLPGMN

PPPYSQFLSRRNEIPLIHFNTPIPRRHTRSAEDDSERDPLNVLKPRARMT

PAPASCSQELPSAEDNSPMASDPLGVVRGGRVNTHAGGTGPEGCRPFAKF

I

Example 14

Figure 10:
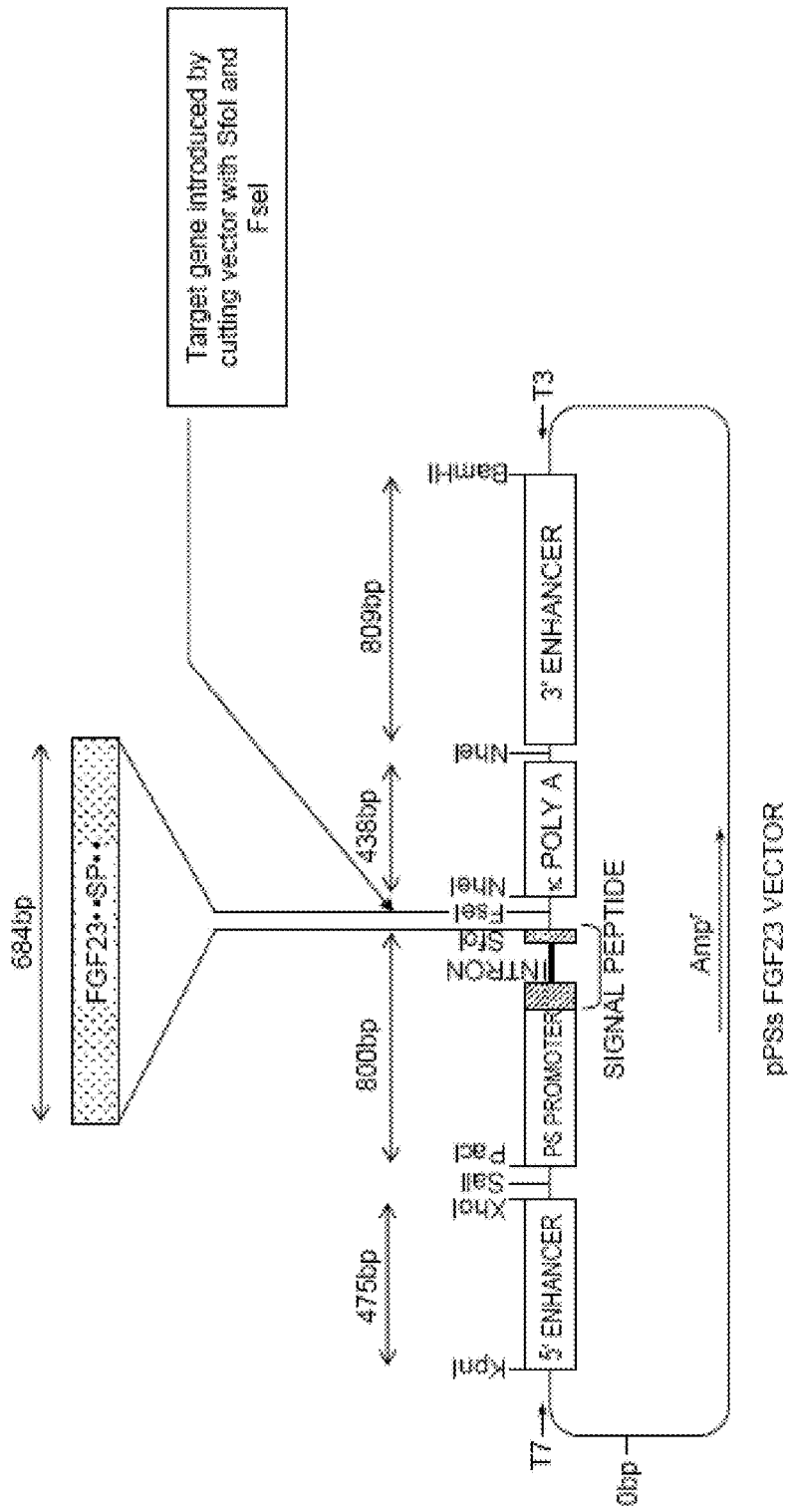
FIG. 10 shows the structure of pPSs FGF23 vector.

Construction of pPSs FGF23 Vector pPSs5.5 described in Example 1-8 of WO2006/78072 was digested with SfoI and FseI, and its terminals were subjected to dephosphorylation treatment with Alkaline Phosphatase derived from E. coli. A DNA fragment including human FGF23 prepared in Example 13 was inserted to the vector. The vector was then introduced into DH5α, and DNA was prepared from the obtained transformants. The nucleotide sequence of the ligated region was confirmed to obtain pPSs FGF23 vector (FIG. 10).

Example 15

Figure 11:
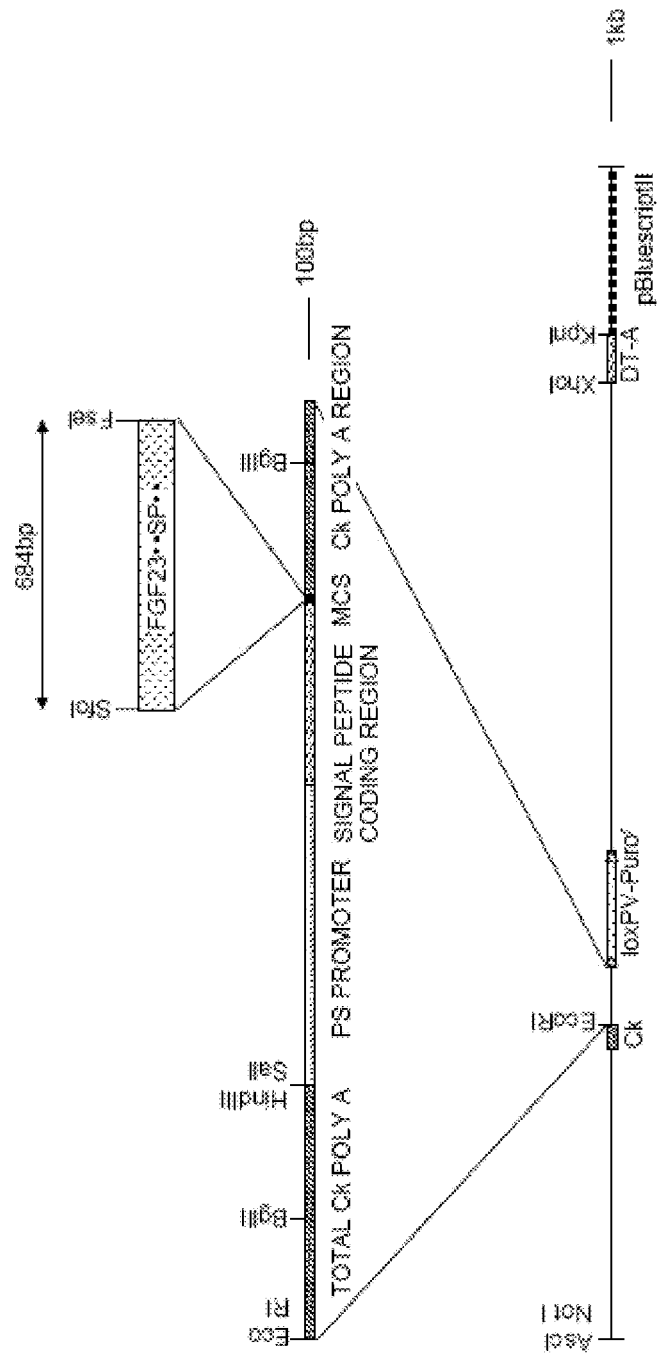
FIG. 11 shows the structure of pUS FGF23 KI vector.

Construction of pUS FGF23 KI Vector pCk 1oxPVΔP described in Example 43-1 of WO2006/78072 was digested with SalI and FseI, and the terminals were subjected to dephosphorylation treatment with Alkaline Phosphatase derived from E. coli C75. After inserting a fragment of about 1.5 kb, wherein the fragment was separated and collected on a 0.8% agarose gel after digesting pPSs FGF23 vector prepared in the above Example 14 with SalI and FseI, the vector was then introduced into E. coliXL10-Gold Ultracompetent Cells (STRATAGENE). DNA was prepared from the obtained transformants. The nucleotide sequence of the ligated region was confirmed to obtain pUS FGF23 KI vector (FIG. 11).

The polynucleotide sequence from the initiation codon to the stop codon of pUS FGF23 KI vector human FGF23 expression unit (985 bp containing mouse Igκ (signal sequence including an intron region substituted to FGF23 signal sequence (the underlined part in SEQ ID NO: 38) and FGF23 mature form sequence in its downstream, SEQ ID NO: 38) and the amino acid sequence encoded by the cDNA (247 amino acids, the underlined part represents mouse Igκ signal sequence, SEQ ID NO: 39) are shown in the following. Sequence information of mouse Igκ signal sequence including an intron region was based on MUSIGKVR1 obtained from GenBank (Accession No. K02159), and the upstream genome sequence thereof was obtained from the UCSC mouse genome database.

```
SEQ ID NO: 38:
ATGGAGACAGACACACTCCTGTTATGGGTACTGCTGCTCTGGGTTCCAGG

TGAGAGTGCAGAGAAGTGTTGGATGCAACCTCTGTGGCCATTATGATACT
```

-continued
CCATGCCTCTCTGTTCTTGATCACTATAATTAGGGCATTTGTCACTGGTT

TTAAGTTTCCCCAGTCCCCTGAATTTTCCATTTTCTCAGAGTGATGTCCA

AAATTATTCTTAAAAATTTAAATAAAAAGGTCCTCTGCTGTGAAGGCTTT

TATACATATATAACAATAATCTTTGTGTTTATCATTCCAGGTTCCACTGG

CTATCCCAATGCCTCCCCACTGCTCGGCTCCAGCTGGGGTGGCCTGATCC

ACCTGTACACAGCCACAGCCAGGAACAGCTACCACCTGCAGATCCACAAG

AATGGCCATGTGGATGGCGCACCCCATCAGACCATCTACAGTGCCCTGAT

GATCAGATCAGAGGATGCTGGCTTTGTGGTGATTACAGGTGTGATGAGCA

GAAGATACCTCTGCATGGATTTCAGAGGCAACATTTTTGGATCACACTAT

TTCGACCCGGAGAACTGCAGGTTCCAACACCAGACGCTGGAAAACGGGTA

CGACGTCTACCACTCTCCTCAGTATCACTTCCTGGTCAGTCTGGGCCGGG

CGAAGAGAGCCTTCCTGCCAGGCATGAACCCACCCCCGTACTCCCAGTTC

CTGTCCCGGAGGAACGAGATCCCCCTAATTCACTTCAACACCCCCATACC

ACGGCGGCACACCCGGAGCGCCGAGGACGACTCGGAGCGGGACCCCCTGA

ACGTGCTGAAGCCCCGGGCCCGGATGACCCCGGCCCCGGCCTCCTGTTCA

CAGGAGCTCCCGAGCGCCGAGGACAACAGCCCGATGGCCAGTGACCCATT

AGGGGTGGTCAGGGGCGGTCGAGTGAACACGCACGCTGGGGGAACGGGCC

CGGAAGGCTGCCGCCCCTTCGCCAAGTTCATCTAG

SEQ ID NO: 39
METDTLLLWVLLLWVPGSTGYPNASPLLGSSWGGLIHLYTATARNSYHLQ

IHKNGHVDGAPHQTIYSALMIRSEDAGFVVITGVMSRRYLCMDFRGNIFG

SHYFDPENCRFQHQTLENGYDVYHSPQYHFLVSLGRAKRAFLPGMNPPPY

SQFLSRRNEIPLIHFNTPIPRRHTRSAEDDSERDPLNVLKPRARMTPAPA

SCSQELPSAEDNSPMASDPLGVVRGGRVNTHAGGTGPEGCRPFAKFI

Example 16

Preparation of pUS FGF23 KI Vector for Electroporation

60 μg of pUS FGF23 KI vector was digested at 37° C. for 5 hours using spermidine-added (1 mM pH7.0, Sigma Aldrich Japan) buffer (Roche Diagnostics, H buffer for restriction enzyme) and NotI (Takara Bio, Inc.). After phenol/chloroform extraction, 2.5 volumes of 100% ethanol and 0.1 volume of 3 M sodium acetate were added, and the mixture was kept at −20° C. for 16 hours. The vector linearized with NotI was collected by centrifugation and sterilized by adding 70% ethanol thereto. 70% ethanol was removed and air drying was performed for 1 hour in a clean bench. An HBS solution was added to form a 0.5 μg/μL DNA solution, and the solution was kept at room temperature for 1 hour to prepare pUS FGF23 KI vector for electroporation.

Example 17

Obtaining a PL FGF23 Mouse ES Cell Line Using pUS FGF23 KI Vector and an RS Element Targeting Mouse ES Cell Line To obtain a PL FGF23 mouse ES cell line, wherein human FGF23-cDNA was inserted by homologous recombination into downstream of an immunoglobulin κ light chain gene, according to the method shown in Example 16, pUS FGF23 KI vector linearized with the restriction enzyme NotI was introduced to RS element targeting mouse ES cells according to the established method (Shinichi Aizawa, "Biotechnology Manual Series 8, Gene Targeting," Yodosha, 1995). RS element targeting mouse ES cells were obtained by the method described in Example 10 of WO2006/78072.

The method for culturing RS element targeting mouse ES cells was in accordance with the described method (Shinichi Aizawa, the aforementioned document), and G418 resistant primary cells in culture (purchased from Invitrogen) treated with mitomycin C (Sigma Aldrich Japan) were used as feeder cells. First, the RS element targeting mouse ES cells were grown and were treated by trypsin, and suspended in HBS to a density of 3×107 cells/ml. 0.5 ml of the cell suspension was mixed with 10 μg of vector DNA. Electroporation (Capacitance: 960 μF, voltage: 250 V, room temperature) was then performed using Gene Pulser Cuvette (electrode distance: 0.4 cm, Bio Rad Laboratories). The electroporated cells were suspended in 10 ml of ES culture medium (Shinichi Aizawa, the aforementioned document), and then the cells were seeded to a plastic Petri dish for 100 mm tissue culture (Falcon, Becton Dickinson), wherein feeder cells were previously seeded. After 36 hours, the culture medium was substituted with ES culture medium containing 0.8 μg/ml puromycin (Sigma Aldrich Japan). Colonies which appeared 7 days after were picked up, and each was grown to confluence in a 24 well plate. Two thirds thereof were suspended in 0.2 ml of a stock medium (FBS+10% DMSO, Sigma Aldrich Japan) and the resulting suspension was kept at −80° C. The remaining one third was seeded to a 12 well gelatin coated plate. The cells were cultured for 2 days, and genomic DNA was prepared from 106 to 107 cells using Puregene DNA Isolation Kits (Qiagen). The resulting genomic DNA of puromycin resistant RS element targeting mouse ES cells was digested with the restriction enzyme EcoRI (Takara Bio, Inc.) and separated by agarose gel electrophoresis. Subsequently, Southern blotting was performed to detect homologous recombinants by using as the probe Ck 3'probe which was the DNA fragment of the 3' terminal of Ig light chain Jκ-Cκ (genomic DNA (XhoI to EcoRI, about 1.4 kb, WO00/10383, FIG. 5) used in the invention described in WO00/10383 (see Example 48). A band (15.1 kb) was detected due to EcoRI digestion in the wild type RS element targeting mouse ES cells. A new band (12.8 kb) is expected to appear below the band in addition to the band (FIG. 12) in a homologous recombinant, and the new band was detected in the puromycin resistant strain. That is, these clones were proven to be having human FGF23-cDNA inserted into downstream of the immunoglobulin κ (chain gene in one of the alleles.

Example 18

Obtaining a US FGF23 Mouse ES Cell Line by Deleting the Drug Resistance Genes from a PL FGF23 Mouse ES Cell Line To obtain a US FGF23 gene introduced mouse ES cell line, wherein 2 kinds of drug resistance genes (Puror, Neor) were deleted, from a PL FGF23 mouse ES cell line, pCA-GGS-Cre vector (Sunaga et al., Mol Reprod Dev., 46: 109-113, 1997) was introduced to PL FGF23 mouse ES cells according to the established method (Shinichi Aizawa, "Biotechnology Manual Series 8, Gene Targeting," Yodosha, 1995).

Figure 12:
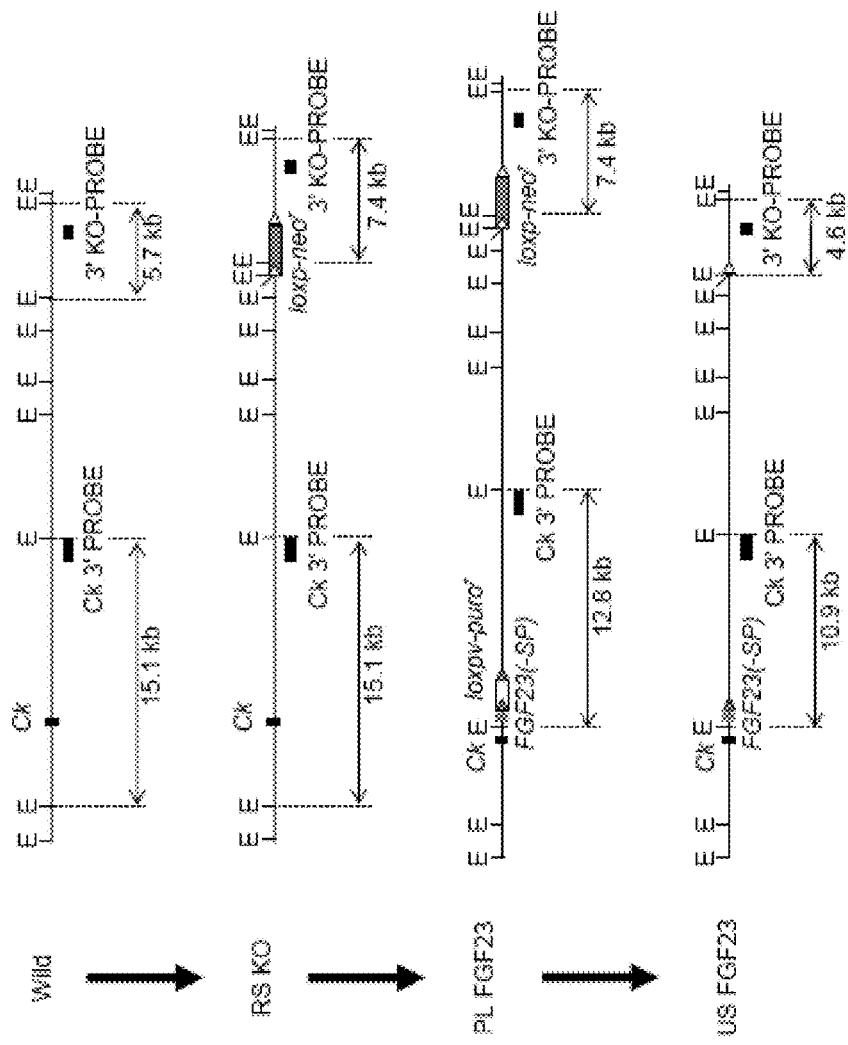
FIG. 12 represents an allele structure in which the drug resistance gene (loxp-neor) is targeted, an allele structure in which human FGF23 (−SP)+drug resistance gene (loxpv-puror) is targeted by using pUS hFGF23 KI vector, an allele structure in which the drug resistance genes (loxp-neor, loxpv-puror) are deleted, and the position of Southern analysis probe. Terms used in the figures are described in detail as follows.

The method for culturing PL FGF23 mouse ES cells was in accordance with the described method (Shinichi Aizawa, the aforementioned document), and G418 resistant primary cells in culture (purchased from Invitrogen) treated with mitomycin C (Sigma Aldrich Japan) were used as feeder cells. First, PL FGF23 mouse ES cells were grown and were treated with trypsin, and suspended in HBS to a density of 3×107 cells/ml. 0.5 ml of the cell suspension was mixed with 10 μg of vector DNA. Electroporation (Capacitance: 960 μF, voltage: 250 V, room temperature) was then performed using a Gene Pulser Cuvette (electrode distance: 0.4 cm, Bio Rad Laboratories). The electroporated cells were suspended in 10 ml of ES culture medium (Shinichi Aizawa, the aforementioned document), and then 2.5 ml of the suspension was seeded to a plastic Petri dish for 60 mm tissue culture (Falcon, Becton Dickinson), wherein feeder cells were previously seeded. After 30 hours, 1000 cells of the ES cells were seeded to a plastic Petri dish for 100 mm tissue culture (Falcon, Becton Dickinson), wherein feeder cells were previously seeded. Colonies which appeared 6 days after were picked up, and each was grown to confluence in a 24 well plate. Two thirds thereof were suspended in 0.2 ml of a stock medium (FBS+10% DMSO, Sigma Aldrich Japan) and the resulting suspension was kept at –80° C. The remaining one third was seeded to a 12 well gelatin coated plate. The cells were cultured for 2 days, and genomic DNA was prepared from 106 to 107 cells using Puregene DNA Isolation Kits (Qiagen). The resulting genomic DNA of mouse ES cells was digested with the restriction enzyme EcoRI (Takara Bio, Inc.) and separated by agarose gel electrophoresis. Subsequently, Southern blotting was performed to detect an ES cell line, wherein only the Puror gene between loxPV sequences was deleted, by using as the probe Ck 3'probe which was the DNA fragment of the 3' terminal of Ig light chain Jκ-Cκ genomic DNA (XhoI to EcoRI, about 1.4 kb, WO00/10383, FIG. 5) used in the invention described in WO00/10383 (see Example 48). Two bands (15.1 kb and 12.8 kb) were detected due to EcoRI digestion in the ES cells retaining the Puror gene, and two bands (15.1 kb and 10.9 kb) were detected due to EcoRI digestion in the ES cell line, wherein only the Puror gene was deleted (FIG. 12). In addition, by using the Southern blotting membrane obtained in the procedure similar to the above, and 3'KO-probe prepared by the method shown in Example 9 of WO2006/78072 as the probe, the ES cell line, wherein the only the Neor gene between loxP sequences was deleted, was detected. Two bands (7.4 K and 5.7 K) were detected due to EcoRI digestion in the ES cells retaining the Neor gene, and two bands (5.7 K and 4.6 K) were detected due to EcoRI digestion in the ES cell line, wherein only the Neor gene was deleted (FIG. 12). From these results, the US FGF23 mouse ES cell line, wherein 2 kinds of the drug resistance genes (Puror, Neor) were deleted simultaneously, was obtained from the PL FGF23 mouse ES cell line.

Example 19

Preparation of a US FGF23 KI Chimeric Mouse Using a US FGF23 Mouse ES Cell Line and a Host Embryo Derived from a B Lymphocyte Deficient Mouse Strain In a homozygous knockout for the immunoglobulin μ chain gene, functional B lymphocytes are deficient and antibodies are not produced (Kitamura et al., Nature, 350: 423-426, 1991). Embryos obtained by cross-breeding the above individual homozygous male and female grown in a clean environment were used as the hosts for preparing chimeric mice in the present Example. In such case, the majority of functional B lymphocytes in a chimeric mouse were derived from the injected ES cells. In the present Example, an individual immunoglobulin μ chain gene knockout mouse described in a report by Tomizuka et al. (Proc. Natl. Acad. Sci. USA, 97: 722-7, 2000), which was backcrossed to the MCH (ICR) strain (CLEA Japan, Inc.) 3 times or more, was used for host embryo preparation.

The US FGF23 mouse ES cell line obtained in the above Example 18, wherein the insertion of human FGF23-cDNA downstream of an immunoglobulin κ chain gene was confirmed, was started from a frozen stock, and the cells were injected to a 8-cell stage embryo obtained by cross-breeding individual male and female mice of the above immunoglobulin μ chain gene knockout homozygotes, with 8-10 cells per embryo. After overnight culture in ES culture medium (Shinichi Aizawa, "Biotechnology Manual Series 8, Gene Targeting," Yodosha, 1995), the embryos were developed into blastocysts. The injection embryos were then transplanted to the uterus in an adopted parent MCH (ICR) mouse (CLEA Japan, Inc.) 2.5 days after pseudopregnancy treatment, with about 10 injection embryos per one side of the uterus, respectively. As a result of transplanting the injection embryos prepared by using a US FGF23 mouse ES cell line prepared in Example 18, chimeric offspring mice were born. An individual chimera is determined by the coat color, in which whether or not the ES cell-derived wild type color (dark brown) can be recognized in the host embryo-derived white color. Among the chimeric offspring mice born, individual mice obviously having parts in the wild type color in the coat color, that is, having recognizable contribution of the ES cells, were obtained. From these results, the US FGF23 mouse ES cell line, wherein human FGF23-cDNA is inserted into downstream of an immunoglobulin κ chain gene, was shown to maintain chimeric forming ability. That is, the cell line has the ability to differentiate into normal tissues of an individual mouse. In addition, the US FGF23 KI chimeric mouse, as will be described later in Example 21, has a high blood FGF23 concentration, and could be used as an animal model of disease exhibiting findings similar to hypophosphatemic rickets.

Example 20

Preparation of Control Chimeric Mouse

A chimeric mouse, in which functional genes including the human FGF23-cDNA prepared according to the method described in Example 11 of WO2006/78072 are not inserted, was used as an individual control chimeric mouse (WT mouse) in the experiment administering C10 antibody to US FGF23 KI chimeric mouse in the following Example 21.

Example 21

Verification of the Effect of C10 Antibody on Improvement in Pathology Using a US FGF23 KI Chimeric Mouse Examples 10 and 12 demonstrated that C10 antibody significantly suppresses the effect of endogenous FGF23 and elevates the serum phosphorous concentration and serum 1,25D concentration thereof compared to 2C3B antibody and C15 antibody in normal cynomolgus monkey. It has been strongly suggested that antibody having neutralizing activity on human FGF23 has therapeutic effect on human diseases such as tumor-induced osteomalacia, hypophosphatemic rickets including XLH and the like, and osteomalacia which are caused by excessive FGF23. Therefore, the C10 antibody obtained in the present invention was investigated for the effect on improvement in pathology caused by excessive human FGF23. For the trial of this therapeutic effect of C10 antibody, experiments were conducted using a US FGF23 KI chimeric mouse (referred to as an "hFGF23KI mouse" hereinafter) prepared in Example 19. 12 hFGF23 KI mice were used as disease-model animals and 6 normal control mice (WT mice, prepared in Example 20) of the same weeks of age were used as the comparative controls. At 7 weeks of age, serum of hFGF23 KI mice was collected to measure the serum concentration of FGF23 (FGF-23 ELISA KIT, Kainos Laboratories, Inc.) and phosphorus, respectively. Compared to the WT mice, serum FGF23 concentration was significantly increased in hFGF23 KI mice (WT mice; n=6, 163 pg/mL, hFGF23KI mice; n=12, 1467 pg/mL). From this result, it was suggested that the introduction of the human FGF23 gene to the hFGF23 KI mouse was precisely performed and that, in addition, excessive exogenous human FGF23 was present in the hFGF23 KI mouse blood. In addition, compared to the WT mice, in hFGF23 KI mice, a significant reduction in the serum phosphorous concentration was shown (WT mice; n=6, 5.82 mg/dL, hFGF23KI mice; n=12, 2.62 mg/dL). It was also suggested that hypophosphatemia was induced due to excessive human FGF23 action in hFGF23 KI mice. At this time point, 12 hFGF23 KI mice were divided into the following 2 groups of 6 mice each, having an equal FGF23 concentration: the C10 antibody administered group and the control IgG1 administered group (FIG. 13). Next, since 8 weeks of age, repeated intravenous administration of C10 antibody or purified human IgG1 (control antibody) for isotype control was conducted at a dose of 30 mg/kg and frequency of once a week five times. Blood samples were taken before the first administration and 3 days after the administration, and the serum was obtained. Appendicular grip strength was measured 24 hours after the fourth administration using a Saitoh-GRIP STRENGTH METER (MK-380S, Muromachi Kikai Co., Ltd.). Appendicular grip strength was evaluated by using as an index the maximum force (grip strength) exerted by a mouse, wherein the mouse was placed on a measurement grid, to let the mouse grip the grid, and then the mouse was pulled by the tail horizontally by our hand until the animal released the grid for being unable to bear the withdrawing force. Bones were evaluated 24 hours after the fifth administration. The collected femur and tibia from mice euthanized by blood drawing from the heart under anesthesia were fixed in 70% ethanol. Serum phosphorous concentration was measured at the before first administration, 3 days after the first administration and 24 hours after the fifth administration. Undecalcified femur was embedded in resin, and stained with Villanueva-Goldner for histological evaluation. Bone mineral content in tibia was measured through the ashing process.

As a result, significantly low serum phosphorus concentration was observed in the hFGF23KI mouse control antibody administered group at the time of grouping and 24 hours after fifth administration compared to the WT mouse control antibody administered group, which means continuous hypophosphatemic conditions (FIG. 14). On the other hand, it was observed that the serum phosphorous concentration at 3 days after administration was increased in hFGF23KI mouse C10 antibody administered group to the same level as that in the WT mouse control antibody administered group (FIG. 14). In addition, the serum phosphorous concentration after the fifth administration in the hFGF23KI mouse C10 antibody administered group was also the same level as that in the WT mouse control antibody administered group, which means the effect of C10 antibody for the increment of serum phosphorus concentration was maintained even after five times of administration (FIG. 15).

As a case of hypophosphatemic patients, skeletal muscle weakness has been reported (Baker and Worthley, Crit Care Resusc., 4: 307-315, 2000). In the present study, hFGF23KI mice had been expected the muscle weakness because of the hypophosphatemia. Consequently, appendicular grip strength was measured by the above method as an index of muscle weakness, and compared among groups. As a result, the grip strength of the hFGF23KI mouse control antibody administered group was shown to be significantly low compared to that of the WT mouse control antibody administered group, and muscle weakness was observed in this disease model (FIG. 16). In contrast, significant improvement of grip strength was observed in the hFGF23KI mouse C10 antibody administered group (FIG. 16).

Next, under-calcified femoral tissues were stained by Villanueva-Goldner method for histological observation. As a result, a large amount of osteoid (shown in red in FIG. 17) was observed in the bone in the hFGF23KI mouse control antibody administered group compared to that in WT mouse control antibody administered group, suggesting that calcification defect was induced in that group. This is widely known as a characteristic symptom of rickets. In contrast, in the hFGF23KI mice received C10 antibody treatment, reduction of the area occupied with osteoid was observed, and predicted that osteoid was replaced with calcified bones (shown in green in FIG. 17). From this result, it was suggested that C10 antibody improves bone calcification reduced by excessive FGF23. Consequently, the amount of minerals contained in tibia was measured by calcification, and compared between each group. The amount of minerals contained in tibia in the hFGF23KI mouse control antibody administered group was significantly reduced compared to the WT mouse control antibody administered group (FIG. 18). In contrast, in the hFGF23KI mouse C10 antibody administered group, improvement in the amount of minerals was confirmed (FIG. 18). From the above results, it was confirmed that, in hFGF23KI mice, C10 antibody administration neutralizes the effect of excessively acting human FGF23 in vivo, and improves various symptoms of hypophosphatemic rickets such as hypophosphatemia, muscle weakness, bone calcification disorder and the like. That is, C10 antibody was shown to be an effective therapeutic agent for various human diseases involving FGF23.

INDUSTRIAL APPLICABILITY

The C10 antibody of the present invention which is an antibody against FGF23 has high activity to raise serum phosphate concentrations in vivo in a sustained manner and/or to raise serum 1,25D concentrations in a sustained manner as compared to known antibodies against FGF23. The present invention can be used with dramatic effects as an agent for prevention or treatment of diseases which are caused by excessive action of FGF23 or for diseases which may be improved in the pathology by controlling the action of FGF23.

What is claimed is:

1. A method for treating a hypophosphatemic disease characterized by elevated FGF23 concentrations compared to that observed in healthy subjects, comprising administering an antibody or functional fragment thereof to a subject in need thereof, wherein the antibody or functional fragment thereof binds to FGF23 and comprises:
   (a) a heavy chain comprising a CDR1 sequence of SEQ ID NO: 40, a CDR2 sequence of SEQ ID NO: 41, and a CDR3 sequence of SEQ ID NO: 42; and
   (b) a light chain comprising a CDR1 sequence of SEQ ID NO: 43, a CDR2 sequence of SEQ ID NO: 44, and a CDR3 sequence of SEQ ID NO: 45.

2. The method of claim 1, wherein the disease is selected from the group consisting of tumor-induced osteomalacia, ADHR, XLH, fibrous dysplasia, and McCune-Albright syndrome.

3. A method for increasing serum phosphorous concentration in a subject suffering from a hypophosphatemic disease characterized by elevated FGF23 concentrations compared to that observed in healthy subjects, comprising administering an antibody or functional fragment thereof to the subject, wherein the antibody or functional fragment thereof binds to FGF23 and comprises:
   (a) a heavy chain comprising a CDR1 sequence of SEQ ID NO: 40, a CDR2 sequence of SEQ ID NO: 41, and a CDR3 sequence of SEQ ID NO: 42; and
   (b) a light chain comprising a CDR1 sequence of SEQ ID NO: 43, a CDR2 sequence of SEQ ID NO: 44, and a CDR3 sequence of SEQ ID NO: 45.

4. The method of claim 3, wherein the disease is selected from the group consisting of tumor-induced osteomalacia, ADHR, XLH, fibrous dysplasia, and McCune-Albright syndrome.

* * * * *

UNITED STATES PATENT AND TRADEMARK OFFICE
CERTIFICATE OF CORRECTION

| | |
|---|---|
| PATENT NO. | : 10,202,446 B2 |
| APPLICATION NO. | : 15/040103 |
| DATED | : February 12, 2019 |
| INVENTOR(S) | : Yamazaki et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 141 days.

Signed and Sealed this
Twenty-seventh Day of August, 2019

Andrei Iancu
*Director of the United States Patent and Trademark Office*

SEQUENCE LISTING

<160> NUMBER OF SEQ ID NOS: 45

<210> SEQ ID NO 1
<211> LENGTH: 30
<212> TYPE: DNA
<213> ORGANISM: Artificial
<220> FEATURE:
<223> OTHER INFORMATION: Synthetic

<400> SEQUENCE: 1
ccggaattca gccactcaga gcagggcacg                                              30

<210> SEQ ID NO 2
<211> LENGTH: 52
<212> TYPE: DNA
<213> ORGANISM: Artificial
<220> FEATURE:
<223> OTHER INFORMATION: Synthetic

<400> SEQUENCE: 2
ataagaatgc ggccgctcaa tggtgatggt gatgatggat gaacttggcg aa                     52

<210> SEQ ID NO 3
<211> LENGTH: 34
<212> TYPE: DNA
<213> ORGANISM: Artificial
<220> FEATURE:
<223> OTHER INFORMATION: Synthetic

<400> SEQUENCE: 3
ataagaatgc ggccgctcag atgaacttgg cgaa                                         34

<210> SEQ ID NO 4
<211> LENGTH: 251
<212> TYPE: PRT
<213> ORGANISM: Homo sapiens

<400> SEQUENCE: 4

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile
                245                 250

<210> SEQ ID NO 5
<211> LENGTH: 31
<212> TYPE: DNA
<213> ORGANISM: Artificial
<220> FEATURE:
<223> OTHER INFORMATION: Synthetic

<400> SEQUENCE: 5
tcttgtccac cttggtgttg ctgggcttgt g                              31

<210> SEQ ID NO 6
<211> LENGTH: 26
<212> TYPE: DNA
<213> ORGANISM: Artificial
<220> FEATURE:
<223> OTHER INFORMATION: Synthetic

<400> SEQUENCE: 6
gttgaagctc tttgtgacgg gcgagc                                    26

<210> SEQ ID NO 7
<211> LENGTH: 23
<212> TYPE: DNA
<213> ORGANISM: Artificial
<220> FEATURE:
<223> OTHER INFORMATION: Synthetic

<400> SEQUENCE: 7
gctggagggc acggtcacca cgc                                       23

<210> SEQ ID NO 8
<211> LENGTH: 30
<212> TYPE: DNA
<213> ORGANISM: Artificial
<220> FEATURE:
<223> OTHER INFORMATION: Synthetic

<400> SEQUENCE: 8
aggcacacaa cagaggcagt tccagatttc                                30

<210> SEQ ID NO 9
<211> LENGTH: 18
<212> TYPE: DNA
<213> ORGANISM: Artificial
<220> FEATURE:
<223> OTHER INFORMATION: Synthetic

<400> SEQUENCE: 9
gtaaaacgac ggccagtg                                             18

<210> SEQ ID NO 10
<211> LENGTH: 17
<212> TYPE: DNA

-continued

<213> ORGANISM: Artificial
<220> FEATURE:
<223> OTHER INFORMATION: Synthetic

<400> SEQUENCE: 10
caggaaacag ctatgac                                                  17

<210> SEQ ID NO 11
<211> LENGTH: 408
<212> TYPE: DNA
<213> ORGANISM: Artificial
<220> FEATURE:
<223> OTHER INFORMATION: Synthetic

<400> SEQUENCE: 11
atggactgga cctggagggt cttctgcttg ctggctgtag ctccaggtgc tcactcccag    60
gtgcagctgg tgcagtctgg ggctgaggtg aagaagcctg ggcctcagt gaaggtttcc   120 tgcaaggcat ctggatacac cttcaccaac cactatatgc actgggtgcg acaggcccct   180
ggacaagggc ttgagtggat gggaataatc aaccctatta gtggtagcac aagtaacgca   240
cagaagttcc agggcagagt caccatgacc agggacacgt ccacgagcac agtctacatg   300
gagctgagca gcctgagatc tgaggacacg gccgtgtatt attgtgcgag agatattgtg   360
gatgcttttg atttctgggg ccaagggaca atggtcaccg tctcttca               408

<210> SEQ ID NO 12
<211> LENGTH: 136
<212> TYPE: PRT
<213> ORGANISM: Artificial
<220> FEATURE:
<223> OTHER INFORMATION: Synthetic

<400> SEQUENCE: 12

Met Asp Trp Thr Trp Arg Val Phe Cys Leu Leu Ala Val Ala Pro Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn His Tyr Met His Trp Val Arg Gln Ala Pro Gly Gln Gly Leu
    50                  55                  60

Glu Trp Met Gly Ile Ile Asn Pro Ile Ser Gly Ser Thr Ser Asn Ala
65                  70                  75                  80

Gln Lys Phe Gln Gly Arg Val Thr Met Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Asp Ile Val Asp Ala Phe Asp Phe Trp Gly Gln
        115                 120                 125

Gly Thr Met Val Thr Val Ser Ser
    130                 135

<210> SEQ ID NO 13
<211> LENGTH: 384
<212> TYPE: DNA
<213> ORGANISM: Artificial
<220> FEATURE:
<223> OTHER INFORMATION: Synthetic

<400> SEQUENCE: 13

```
atggacatga gggtccccgc tcagctcctg gggcttctgc tgctctggct cccaggtgcc    60
agatgtgcca tccagttgac ccagtctcca tcctccctgt ctgcatctgt aggagacaga   120
gtcaccatca cttgccgggc aagtcagggc attagcagtg ctttagtctg gtatcagcag   180
aaaccaggga aagctcctaa gctcctgatc tatgatgcct ccagtttgga aagtggggtc   240
ccatcaaggt tcagcggcag tggatctggg acagatttca ctctcaccat cagcagcctg   300
cagcctgaag attttgcaac ttattactgt caacagttta tgattacttc actttcggc    360 cctgggacca aagtggatat caaa                                          384
```

```
<210> SEQ ID NO 14
<211> LENGTH: 128
<212> TYPE: PRT
<213> ORGANISM: Artificial
<220> FEATURE:
<223> OTHER INFORMATION: Synthetic

<400> SEQUENCE: 14
```

Met Asp Met Arg Val Pro Ala Gln Leu Leu Gly Leu Leu Leu Leu Trp
1               5                   10                  15

Leu Pro Gly Ala Arg Cys Ala Ile Gln Leu Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Ser Ser Ala Leu Val Trp Tyr Gln Gln Lys Pro Gly Lys
    50                  55                  60

Ala Pro Lys Leu Leu Ile Tyr Asp Ala Ser Ser Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Phe Asn Asp Tyr Phe Thr Phe Gly Pro Gly Thr Lys Val Asp Ile Lys
        115                 120                 125

```
<210> SEQ ID NO 15
<211> LENGTH: 41
<212> TYPE: DNA
<213> ORGANISM: Artificial
<220> FEATURE:
<223> OTHER INFORMATION: Synthetic

<400> SEQUENCE: 15
agagagagag atctctcacc atggacatga gggtccccgc t                        41

<210> SEQ ID NO 16
<211> LENGTH: 42
<212> TYPE: DNA
<213> ORGANISM: Artificial
<220> FEATURE:
<223> OTHER INFORMATION: Synthetic

<400> SEQUENCE: 16
agagagagag cgtacgtttg atatccactt tggtcccagg gc                       42

<210> SEQ ID NO 17
<211> LENGTH: 44
<212> TYPE: DNA
<213> ORGANISM: Artificial
<220> FEATURE:
<223> OTHER INFORMATION: Synthetic
```

<400> SEQUENCE: 17
agagagagag gtcgaccacc atggactgga cctggagggt cttc                44

<210> SEQ ID NO 18
<211> LENGTH: 40
<212> TYPE: DNA
<213> ORGANISM: Artificial
<220> FEATURE:
<223> OTHER INFORMATION: Synthetic

<400> SEQUENCE: 18
agagagagag gctagctgaa gagacggtga ccattgtccc                     40

<210> SEQ ID NO 19
<211> LENGTH: 23
<212> TYPE: DNA
<213> ORGANISM: Artificial
<220> FEATURE:
<223> OTHER INFORMATION: Synthetic

<400> SEQUENCE: 19
ggtgccaggg ggaagaccga tgg                                       23

<210> SEQ ID NO 20
<211> LENGTH: 30
<212> TYPE: DNA
<213> ORGANISM: Artificial
<220> FEATURE:
<223> OTHER INFORMATION: Synthetic

<400> SEQUENCE: 20
ccaagggccc atcggtcttc ccctggcac                                 30

<210> SEQ ID NO 21
<211> LENGTH: 24
<212> TYPE: DNA
<213> ORGANISM: Artificial
<220> FEATURE:
<223> OTHER INFORMATION: Synthetic

<400> SEQUENCE: 21
gacaccctca tgatctcccg gacc                                      24

<210> SEQ ID NO 22
<211> LENGTH: 24
<212> TYPE: DNA
<213> ORGANISM: Artificial
<220> FEATURE:
<223> OTHER INFORMATION: Synthetic

<400> SEQUENCE: 22
tgttctccgg ctgcccattg ctct                                      24

<210> SEQ ID NO 23
<211> LENGTH: 27
<212> TYPE: DNA
<213> ORGANISM: Artificial
<220> FEATURE:
<223> OTHER INFORMATION: Synthetic

<400> SEQUENCE: 23
tctatataag cagagctggg tacgtcc                                   27

<210> SEQ ID NO 24

```
<211> LENGTH: 26
<212> TYPE: DNA
<213> ORGANISM: Artificial
<220> FEATURE:
<223> OTHER INFORMATION: Synthetic

<400> SEQUENCE: 24
tggctgcacc atctgtcttc atcttc                                            26

<210> SEQ ID NO 25
<211> LENGTH: 27
<212> TYPE: DNA
<213> ORGANISM: Artificial
<220> FEATURE:
<223> OTHER INFORMATION: Synthetic

<400> SEQUENCE: 25
ggtacgtgaa ccgtcagatc gcctgga                                           27

<210> SEQ ID NO 26
<211> LENGTH: 35
<212> TYPE: DNA
<213> ORGANISM: Artificial
<220> FEATURE:
<223> OTHER INFORMATION: Synthetic

<400> SEQUENCE: 26
cggaattcca ccatgttggg ggcccgcctc aggct                                  35

<210> SEQ ID NO 27
<211> LENGTH: 34
<212> TYPE: DNA
<213> ORGANISM: Artificial
<220> FEATURE:
<223> OTHER INFORMATION: Synthetic

<400> SEQUENCE: 27
atttgcggcc gctagatgaa cttggcgaag gggc                                   34

<210> SEQ ID NO 28
<211> LENGTH: 756
<212> TYPE: DNA
<213> ORGANISM: Macaca fascicularis

<400> SEQUENCE: 28
atgttggggg cccgcctcag gctctgggtc tgtgccttgt gcagcgtctg cagcatgagc       60
gtcatcagag cctatcccaa tgcctcccca ttgctcggct ccagctgggg tggcctgatc      120
cacctgtaca cagccacagc caggaacagc taccacctgc agatccacaa gaatggccac      180
gtggatggcg cacccatca gaccatctac agtgccctga tgatcagatc agaggatgct      240
ggctttgtgg tgattacagg tgtgatgagc agaagatacc tctgcatgga tttcggaggc      300
aacatttttg gatcacacta tttcaacccg gagaactgca ggttccgaca ctggacgctg      360
gagaacggct acgacgtcta ccactctcct cagcatcact ttctggtcag tctgggccgg      420
gcgaagaggg ccttcctgcc aggcatgaac ccacccccct actcccagtt cctgtcccgg      480
aggaacgaga tccccctcat ccacttcaac accccagac acggcggca cccggagc        540
gccgaggacg actcggagcg ggaccccctg aacgtgctga gccccgggc ccggatgacc      600
ccggccccgg cctcctgctc acaggagctc ccgagcgccg aggacaacag cccggtggcc      660
agcgaccgt aggggtggt cagggcggt cgggtgaaca cgcacgctgg gggaacgggc      720
ccggaagcct gccgcccctt cgccaagttc atctag                                756
```

<210> SEQ ID NO 29
<211> LENGTH: 251
<212> TYPE: PRT
<213> ORGANISM: Macaca fascicularis

<400> SEQUENCE: 29

Met Leu Gly Ala Arg Leu Arg Leu Trp Val Cys Ala Leu Cys Ser Val
1               5                   10                  15

Cys Ser Met Ser Val Ile Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Gly Gly Asn Ile Phe Gly Ser His Tyr Phe Asn Pro Glu Asn
            100                 105                 110

Cys Arg Phe Arg His Trp Thr Leu Glu Asn Gly Tyr Asp Val Tyr His
        115                 120                 125

Ser Pro Gln His His Phe Leu Val Ser Leu Gly Arg Ala Lys Arg Ala
    130                 135                 140

Phe Leu Pro Gly Met Asn Pro Pro Tyr Ser Gln Phe Leu Ser Arg Arg
145                 150                 155                 160

Arg Asn Glu Ile Pro Leu Ile His Phe Asn Thr Pro Arg Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Val Ala Ser Asp Pro Leu
    210                 215                 220

Gly Val Val Arg Gly Gly Arg Val Asn Thr His Ala Gly Gly Thr Gly
225                 230                 235                 240

Pro Glu Ala Cys Arg Pro Phe Ala Lys Phe Ile
                245                 250

<210> SEQ ID NO 30
<211> LENGTH: 1417
<212> TYPE: DNA
<213> ORGANISM: Artificial
<220> FEATURE:
<223> OTHER INFORMATION: Synthetic

<400> SEQUENCE: 30
gtcgaccacc atggactgga cctggagggt cttctgcttg ctggctgtag ctccaggtgc      60
tcactcccag gtgcagctgg tgcagtctgg ggctgaggtg aagaagcctg gggcctcagt     120
gaaggtttcc tgcaaggcat ctggatacac cttcaccaac cactatatgc actgggtgcg     180
acaggcccct ggacaagggc ttgagtggat gggaataatc aaccctatta gtggtagcac     240
aagtaacgca cagaagttcc agggcagagt caccatgacc agggacacgt ccacgagcac     300
agtctacatg gagctgagca gcctgagatc tgaggacacg gccgtgtatt attgtgcgag     360

```
agatattgtg gatgcttttg atttctgggg ccaagggaca atggtcaccg tctcttcagc    420
tagcaccaag ggcccatcgg tcttccccct ggcaccctcc tccaagagca cctctggggg    480
cacagcggcc ctgggctgcc tggtcaagga ctacttcccc gaaccggtga cggtgtcgtg    540
gaactcaggc gccctgacca gcggcgtgca ccttcccg gctgtcctac agtcctcagg      600
actctactcc ctcagcagcg tggtgaccgt gccctccagc agcttgggca cccagaccta    660
catctgcaac gtgaatcaca agcccagcaa caccaaggtg gacaagaaag ttgagcccaa    720
atcttgtgac aaaactcaca catgcccacc gtgcccagca cctgaactcc tggggggacc    780
gtcagtcttc ctcttccccc caaaacccaa ggacaccctc atgatctccc ggacccctga    840
ggtcacatgc gtggtggtgg acgtgagcca cgaagaccct gaggtcaagt tcaactggta    900
cgtggacggc gtggaggtgc ataatgccaa gacaaagccg cgggaggagc agtacaacag    960
cacgtaccgt gtggtcagcg tcctcaccgt cctgcaccag gactggctga atggcaagga    1020
gtacaagtgc aaggtctcca acaaagccct cccagcccccc atcgagaaaa ccatctccaa    1080
agccaaaggg cagccccgag aaccacaggt gtacaccctg cccccatccc gggatgagct    1140
gaccaagaac caggtcagcc tgacctgcct ggtcaaaggc ttctatccca gcgacatcgc    1200
cgtggagtgg gagagcaatg ggcagccgga gaacaactac aagaccacgc ctcccgtgct    1260
ggactccgac ggctccttct tcctctacag caagctcacc gtggacaaga gcaggtggca    1320
gcaggggaac gtcttctcat gctccgtgat gcatgaggct ctgcacaacc actacacgca    1380
gaagagcctc tccctgtctc cgggtaaatg aggatcc                            1417
```

<210> SEQ ID NO 31
<211> LENGTH: 466
<212> TYPE: PRT
<213> ORGANISM: Artificial
<220> FEATURE:
<223> OTHER INFORMATION: Synthetic

<400> SEQUENCE: 31

```
Met Asp Trp Thr Trp Arg Val Phe Cys Leu Leu Ala Val Ala Pro Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Asn His Tyr Met His Trp Val Arg Gln Ala Pro Gly Gln Gly Leu
        50                  55                  60

Glu Trp Met Gly Ile Ile Asn Pro Ile Ser Gly Ser Thr Ser Asn Ala
65                  70                  75                  80

Gln Lys Phe Gln Gly Arg Val Thr Met Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Asp Ile Val Asp Ala Phe Asp Phe Trp Gly Gln
        115                 120                 125

Gly Thr Met Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175
```

```
Trp Asn Ser Gly Ala Leu Thr Ser Gly Val His Thr Phe Pro Ala Val
            180                 185                 190
Leu Gln Ser Ser Gly Leu Tyr Ser Leu Ser Ser Val Val Thr Val Pro
        195                 200                 205
Ser Ser Ser Leu Gly Thr Gln Thr Tyr Ile Cys Asn Val Asn His Lys
    210                 215                 220
Pro Ser Asn Thr Lys Val Asp Lys Lys Val Glu Pro Lys Ser Cys Asp
225                 230                 235                 240
Lys Thr His Thr Cys Pro Pro Cys Pro Ala Pro Glu Leu Leu Gly Gly
                245                 250                 255
Pro Ser Val Phe Leu Phe Pro Pro Lys Pro Lys Asp Thr Leu Met Ile
            260                 265                 270
Ser Arg Thr Pro Glu Val Thr Cys Val Val Val Asp Val Ser His Glu
        275                 280                 285
Asp Pro Glu Val Lys Phe Asn Trp Tyr Val Asp Gly Val Glu Val His
    290                 295                 300
Asn Ala Lys Thr Lys Pro Arg Glu Glu Gln Tyr Asn Ser Thr Tyr Arg
305                 310                 315                 320
Val Val Ser Val Leu Thr Val Leu His Gln Asp Trp Leu Asn Gly Lys
                325                 330                 335
Glu Tyr Lys Cys Lys Val Ser Asn Lys Ala Leu Pro Ala Pro Ile Glu
            340                 345                 350
Lys Thr Ile Ser Lys Ala Lys Gly Gln Pro Arg Glu Pro Gln Val Tyr
        355                 360                 365
Thr Leu Pro Pro Ser Arg Asp Glu Leu Thr Lys Asn Gln Val Ser Leu
    370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Val
                405                 410                 415
Leu Asp Ser Asp Gly Ser Phe Phe Leu Tyr Ser Lys Leu Thr Val Asp
            420                 425                 430
Lys Ser Arg Trp Gln Gln Gly Asn Val Phe Ser Cys Ser Val Met His
        435                 440                 445
Glu Ala Leu His Asn His Tyr Thr Gln Lys Ser Leu Ser Leu Ser Pro
    450                 455                 460
Gly Lys
465

<210> SEQ ID NO 32
<211> LENGTH: 724
<212> TYPE: DNA
<213> ORGANISM: Artificial
<220> FEATURE:
<223> OTHER INFORMATION: Synthetic

<400> SEQUENCE: 32
agatctctca ccatggacat gagggtcccc gctcagctcc tggggcttct gctgctctgg      60
ctcccaggtg ccagatgtgc catccagttg acccagtctc catcctccct gtctgcatct     120
gtaggagaca gagtcaccat cacttgccgg gcaagtcagg gcattagcag tgctttagtc     180
tggtatcagc agaaaccagg gaaagctcct aagctcctga tctatgatgc ctccagtttg     240
gaaagtgggg tcccatcaag gttcagcggc agtggatctg ggacagattt cactctcacc     300
atcagcagcc tgcagcctga agattttgca acttattact gtcaacagtt taatgattac     360
```

```
ttcactttcg gccctgggac caaagtggat atcaaacgta cggtggctgc accatctgtc    420
ttcatcttcc cgccatctga tgagcagttg aaatctggaa ctgcctctgt tgtgtgcctg    480
ctgaataact tctatcccag agaggccaaa gtacagtgga aggtggataa cgccctccaa    540
tcgggtaact cccaggagag tgtcacagag caggacagca aggacagcac ctacagcctc    600
agcagcaccc tgacgctgag caaagcagac tacgagaaac acaaagtcta cgcctgcgaa    660
gtcacccatc agggcctgag ctcgcccgtc acaaagagct tcaacagggg agagtgttga    720
attc                                                                 724
```

<210> SEQ ID NO 33
<211> LENGTH: 235
<212> TYPE: PRT
<213> ORGANISM: Artificial
<220> FEATURE:
<223> OTHER INFORMATION: Synthetic

<400> SEQUENCE: 33

```
Met Asp Met Arg Val Pro Ala Gln Leu Leu Gly Leu Leu Leu Leu Trp
1               5                   10                  15

Leu Pro Gly Ala Arg Cys Ala Ile Gln Leu Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Ser Ser Ala Leu Val Trp Tyr Gln Gln Lys Pro Gly Lys
    50                  55                  60

Ala Pro Lys Leu Leu Ile Tyr Asp Ala Ser Ser Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Phe Asn Asp Tyr Phe Thr Phe Gly Pro Gly Thr Lys Val Asp Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 34
<211> LENGTH: 35
<212> TYPE: DNA
<213> ORGANISM: Homo sapiens

<400> SEQUENCE: 34

```
tatcccaatg cctcccact gctcggctcc agctg                                 35
```

<210> SEQ ID NO 35
<211> LENGTH: 45
<212> TYPE: DNA
<213> ORGANISM: Homo sapiens

<400> SEQUENCE: 35
ttggccggcc ctagatgaac ttggcgaagg ggcggcagcc ttccg    45

<210> SEQ ID NO 36
<211> LENGTH: 756
<212> TYPE: DNA
<213> ORGANISM: Homo sapiens

<400> SEQUENCE: 36
atgttggggg cccgcctcag gctctgggtc tgtgccttgt gcagcgtctg cagcatgagc    60
gtcctcagag cctatcccaa tgcctcccca ctgctcggct ccagctgggg tggcctgatc   120
cacctgtaca cagccacagc caggaacagc taccacctgc agatcccaaa gaatggccat   180
gtggatggcg cacccatca gaccatctac agtgccctga tgatcagatc agaggatgct   240
ggctttgtgg tgattacagg tgtgatgagc agaagatacc tctgcatgga tttcagaggc   300
aacatttttg gatcacacta tttcgacccg agaactgca ggttccaaca ccagacgctg   360
gaaaacgggt acgacgtcta ccactctcct cagtatcact tcctggtcag tctgggccgg   420
gcgaagagag ccttcctgcc aggcatgaac ccaccccgt actcccagtt cctgtcccgg   480
aggaacgaga tccccctaat tcacttcaac accccatac acggcggca caccccggagc   540
gccgaggacg actcggagcg ggaccccctg aacgtgctga gccccgggc ccggatgacc   600
ccggccccgg cctcctgttc acaggagctc ccgagcgccg aggacaacag cccgatggcc   660
agtgacccat taggggtggt cagggcggt cgagtgaaca cgcacgctgg gggaacgggc   720
ccggaaggct gccgccccctt cgccaagttc atctag                             756

<210> SEQ ID NO 37
<211> LENGTH: 251
<212> TYPE: PRT
<213> ORGANISM: Homo sapiens

<400> SEQUENCE: 37

Met Leu Gly Ala Arg Leu Arg Leu Trp Val Cys Ala Leu Cys Ser Val
1               5                   10                  15
Cys Ser Met Ser Val Leu Arg Ala Tyr Pro Asn Ala Ser Pro Leu Leu
                20                  25                  30
Gly Ser Ser Trp Gly Gly Leu Ile His Leu Tyr Thr Ala Thr Ala Arg
            35                  40                  45
Asn Ser Tyr His Leu Gln Ile His Lys Asn Gly His Val Asp Gly Ala
        50                  55                  60
Pro His Gln Thr Ile Tyr Ser Ala Leu Met Ile Arg Ser Glu Asp Ala
65                  70                  75                  80
Gly Phe Val Val Ile Thr Gly Val Met Ser Arg Arg Tyr Leu Cys Met
                85                  90                  95
Asp Phe Arg Gly Asn Ile Phe Gly Ser His Tyr Phe Asp Pro Glu Asn
            100                 105                 110
Cys Arg Phe Gln His Gln Thr Leu Glu Asn Gly Tyr Asp Val Tyr His
        115                 120                 125
Ser Pro Gln Tyr His Phe Leu Val Ser Leu Gly Arg Ala Lys Arg Ala
        130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
            165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile
                245                 250

<210> SEQ ID NO 38
<211> LENGTH: 985
<212> TYPE: DNA
<213> ORGANISM: Mus musculus

<400> SEQUENCE: 38

| | | |
|---|---|---|
| atggagacag acacactcct gttatgggta ctgctgctct gggttccagg tgagagtgca | 60 |
| gagaagtgtt ggatgcaacc tctgtggcca ttatgatact ccatgcctct ctgttcttga | 120 |
| tcactataat tagggcattt gtcactggtt ttaagtttcc ccagtcccct gaattttcca | 180 |
| ttttctcaga gtgatgtcca aaattattct taaaaattta ataaaaagg tcctctgctg | 240 |
| tgaaggcttt tatacatata taacaataat ctttgtgttt atcattccag gttccactgg | 300 |
| ctatcccaat gcctcccac tgctcggctc cagctggggt ggcctgatcc acctgtacac | 360 |
| agccacagcc aggaacagct accacctgca gatccacaag aatggccatg tggatggcgc | 420 |
| accccatcag accatctaca gtgccctgat gatcagatca gaggatgctg ctttgtggt | 480 |
| gattacaggt gtgatgagca aagataccct ctgcatggat ttcagaggca acatttttgg | 540 |
| atcacactat ttcgacccgg agaactgcag gttccaacac cagacgctgg aaaacgggta | 600 |
| cgacgtctac cactctcctc agtatcactt cctggtcagt ctgggccggg cgaagagagc | 660 |
| cttcctgcca ggcatgaacc caccccgta ctcccagttc ctgtcccgga ggaacgagat | 720 |
| cccccctaatt cacttcaaca cccccatacc acggcggcac acccgagcg ccaggacga | 780 |
| ctcggagcgg gaccccctga cgtgctgaa gccccgggcc ggatgacccc ggccccggc | 840 |
| ctcctgttca caggagctcc cgagcgccga ggacaacagc ccgatggcca gtgacccatt | 900 |
| aggggtggtc aggggcggtc gagtgaacac gcacgctggg ggaacgggcc cggaaggctg | 960 |
| ccgcccttc gccaagttca tctag | 985 |

<210> SEQ ID NO 39
<211> LENGTH: 247
<212> TYPE: PRT
<213> ORGANISM: Mus musculus

<400> SEQUENCE: 39

Met Glu Thr Asp Thr Leu Leu Leu Trp Val Leu Leu Leu Trp Val Pro
1               5                   10                  15

Gly Ser Thr Gly Tyr Pro Asn Ala Ser Pro Leu Leu Gly Ser Ser Trp
                20                  25                  30

Gly Gly Leu Ile His Leu Tyr Thr Ala Thr Ala Arg Asn Ser Tyr His
            35                  40                  45

Leu Gln Ile His Lys Asn Gly His Val Asp Gly Ala Pro His Gln Thr
             50                  55                  60

Ile Tyr Ser Ala Leu Met Ile Arg Ser Glu Asp Ala Gly Phe Val Val
 65                  70                  75                  80

Ile Thr Gly Val Met Ser Arg Arg Tyr Leu Cys Met Asp Phe Arg Gly
                 85                  90                  95

Asn Ile Phe Gly Ser His Tyr Phe Asp Pro Glu Asn Cys Arg Phe Gln
                100                 105                 110

His Gln Thr Leu Glu Asn Gly Tyr Asp Val Tyr His Ser Pro Gln Tyr
            115                 120                 125

His Phe Leu Val Ser Leu Gly Arg Ala Lys Arg Ala Phe Leu Pro Gly
        130                 135                 140

Met Asn Pro Pro Pro Tyr Ser Gln Phe Leu Ser Arg Arg Asn Glu Ile
145                 150                 155                 160

Pro Leu Ile His Phe Asn Thr Pro Ile Pro Arg Arg His Thr Arg Ser
                165                 170                 175

Ala Glu Asp Asp Ser Glu Arg Asp Pro Leu Asn Val Leu Lys Pro Arg
            180                 185                 190

Ala Arg Met Thr Pro Ala Pro Ala Ser Cys Ser Gln Glu Leu Pro Ser
        195                 200                 205

Ala Glu Asp Asn Ser Pro Met Ala Ser Asp Pro Leu Gly Val Val Arg
    210                 215                 220

Gly Gly Arg Val Asn Thr His Ala Gly Gly Thr Gly Pro Glu Gly Cys
225                 230                 235                 240

Arg Pro Phe Ala Lys Phe Ile
                245

<210> SEQ ID NO 40
<211> LENGTH: 5
<212> TYPE: PRT
<213> ORGANISM: Artificial
<220> FEATURE:
<223> OTHER INFORMATION: Synthetic

<400> SEQUENCE: 40

Asn His Tyr Met His
1               5

<210> SEQ ID NO 41
<211> LENGTH: 17
<212> TYPE: PRT
<213> ORGANISM: Artificial
<220> FEATURE:
<223> OTHER INFORMATION: Synthetic

<400> SEQUENCE: 41

Ile Ile Asn Pro Ile Ser Gly Ser Thr Ser Asn Ala Gln Lys Phe Gln
1               5                   10                  15

Gly

<210> SEQ ID NO 42
<211> LENGTH: 8
<212> TYPE: PRT
<213> ORGANISM: Artificial
<220> FEATURE:
<223> OTHER INFORMATION: Synthetic

<400> SEQUENCE: 42

Asp Ile Val Asp Ala Phe Asp Phe

```
<210> SEQ ID NO 43
<211> LENGTH: 11
<212> TYPE: PRT
<213> ORGANISM: Artificial
<220> FEATURE:
<223> OTHER INFORMATION: Synthetic

<400> SEQUENCE: 43

Arg Ala Ser Gln Gly Ile Ser Ser Ala Leu Val
1               5                   10

<210> SEQ ID NO 44
<211> LENGTH: 7
<212> TYPE: PRT
<213> ORGANISM: Artificial
<220> FEATURE:
<223> OTHER INFORMATION: Synthetic

<400> SEQUENCE: 44

Asp Ala Ser Ser Leu Glu Ser
1               5

<210> SEQ ID NO 45
<211> LENGTH: 8
<212> TYPE: PRT
<213> ORGANISM: Artificial
<220> FEATURE:
<223> OTHER INFORMATION: Synthetic

<400> SEQUENCE: 45

Gln Gln Phe Asn Asp Tyr Phe Thr
1               5
```